United States Patent
Sauve et al.

(10) Patent No.: US 9,790,252 B2
(45) Date of Patent: *Oct. 17, 2017

(54) 2-FLUORINATED RIBOSES AND ARABINOSES AND METHODS OF USE AND SYNTHESIS

(75) Inventors: Anthony A. Sauve, New Rochelle, NY (US); Yana Cen, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 887 days.

This patent is subject to a terminal disclaimer.

(21) Appl. No.: 13/381,587

(22) PCT Filed: Jul. 1, 2010

(86) PCT No.: PCT/US2010/040816
§ 371 (c)(1),
(2), (4) Date: Dec. 29, 2011

(87) PCT Pub. No.: WO2011/003018
PCT Pub. Date: Jan. 6, 2011

(65) Prior Publication Data
US 2012/0108535 A1  May 3, 2012

Related U.S. Application Data

(60) Provisional application No. 61/222,424, filed on Jul. 1, 2009.

(51) Int. Cl.
| | | |
|---|---|---|
| A61K 31/706 | (2006.01) |
| C07H 23/00 | (2006.01) |
| C07H 19/048 | (2006.01) |
| C07H 19/056 | (2006.01) |
| C07H 19/06 | (2006.01) |
| C07H 19/073 | (2006.01) |
| C07H 19/12 | (2006.01) |
| C07H 19/16 | (2006.01) |
| C07H 19/173 | (2006.01) |
| C07H 19/19 | (2006.01) |

(52) U.S. Cl.
CPC .......... *C07H 23/00* (2013.01); *C07H 19/048* (2013.01); *C07H 19/056* (2013.01); *C07H 19/06* (2013.01); *C07H 19/073* (2013.01); *C07H 19/12* (2013.01); *C07H 19/16* (2013.01); *C07H 19/173* (2013.01); *C07H 19/19* (2013.01)

(58) Field of Classification Search
CPC .... C07H 19/048; C07H 19/056; C07H 19/06; C07H 19/073; C07H 23/00; C07H 19/16; C07H 19/173; C07H 19/19; C07H 19/12
USPC .................... 514/43, 52; 536/22.1
See application file for complete search history.

(56) References Cited

U.S. PATENT DOCUMENTS

| | | | |
|---|---|---|---|
| 4,751,221 A | 6/1988 | Watanabe et al. |
| 5,384,310 A | 1/1995 | Montgomery et al. |
| 5,744,597 A | 4/1998 | Chou et al. |
| 2005/0187384 A1 | 8/2005 | Sznaidman |
| 2008/0194803 A1* | 8/2008 | Sinclair et al. ............. 536/23.2 |

OTHER PUBLICATIONS

Handlon et al. (J. Am. Chem. Soc. 1994, 116, 12087-12088).*
Anderson et al., "Potential Anticancer Agents. VII. Synthesis and Ammonolysis of Methyl 2,3-Anhydro-Dribofuranoside," *J. Am. Chem. Soc*, 80, 5247-5252 (1958).
Ashley et al., "Inactivation of the Ribonucleoside Triphosphate Reductase from Lactobacillus leichmannii by 2'-Chloro-2'-deoxyuridine 5'-Triphosphate: A 3'-2' Hydrogen Transfer during the Formation of 3'-Keto-2'-deoxyuridine 5'-Triphosphate," *J. Biochemistry*, 27, 7841-7845 (1988).
Bauta et al., "A New Process for Antineoplastic Agent Clofarabine," Org. Proc R&D 2004, 8, 889-896.
Bonate, "Discovery and development of clofarabine: a nucleoside analogue for treating cancer," *Nat. Rev. Drug Discov.*, 2006, 5, 855-863.
Cen et al., "Diastereocontrolled Electrophilic Fluorinations of 2-Deoxyribonolactone: Syntheses of All Corresponding 2-Deoxy-2-fluorolactones and 20-Deoxy-20-fluoro-NAD⁺s," *The Journal of Organic Chemistry*, 2009, 74(16): 5779-5789.
Chou et al., "Stereospecific Synthesis of 2-Deoxy-2,2-difluororibonolactone and Its Use in the Preparation. of 2'-Deoxy-2',2'-difluoro-β-$_D$-ribofuranosyl Pyrimidine Nucleosides: The Key Role of Selective Crystallization," *Synthesis* 1992, 6, 565-570.
Clark et al., "Design, Synthesis, and Antiviral Activity of 2'-Deoxy-2'-fluoro-2'-C-methylcytidine, a Potent Inhibitor of Hepatitis C Virus Replication," *J. Med. Chem.*, 2005, 48, 5504-5508.
Codingtonet al., "Nucleosides. XVIII. Synthesis of 2'-Fluorothymidine, 2'Fluorodeoxyuridine, and Other 2'Holageno-2'-Deoxy Nucleosides," *J. Org. Chem.*, 1964, 29, 558-564.
Damrauer et al., "Effect of Substituents on the Gas-Phase Acidity of Silanols," *J. Am. Chem. Soc.*, 1991, 113, 4431-4435.

(Continued)

*Primary Examiner* — Shaojia Anna Jiang
*Assistant Examiner* — Michael C Henry
(74) *Attorney, Agent, or Firm* — Leydig, Voit & Mayer, Ltd.

(57) ABSTRACT

Disclosed are halogenated 2-deoxy-lactone, 2'-deoxy-nucleosides, and derivatives thereof, for example, a compound of formula (I). Also disclosed are a composition comprising a pharmaceutically acceptable carrier and at least one compound or salt of the invention, and a method of treating a disorder is selected from the group consisting of an abnormal cellular proliferation, a viral infection, and an autoimmune disorder.

9 Claims, 52 Drawing Sheets

(56) References Cited

OTHER PUBLICATIONS

Dax et al., "Synthesis of deoxyfluoro sugars from carbohydrate precursors," *J. Carbohydr. Res.*, 2000, 327, 47-86.
Dehoux et al., "Stereoselective Preparation of Protected Thymine Polyoxin C and Approaches Towards Synthesis of Its C2'-Modified Analogues," *Eur. J. Org. Chem.*, 2001, 6, 1105-1113.
Eli Lilly, Eli Lilly 2007 Annual Report, 2007.
Enders et al., "Diastereoselective Electrophilic Fluorination of Enantiopure α-Silylketones Using N-Fluoro-benzosulfonimide: Regio- and Enantioselective Synthesis of α-Fluoroketones," *Synthesis*, 2001, 15, 2307-2319.
Enders et al., "Regio- and Enantioselective Synthesis of α-Fluoroketones by Electrophilic Fluorination of α-Silylketone Enolates with N-Fluorobenzo-sulfonimide," *Angew. Chem. Int. Ed.*, 1997, 36, 2362-2364.
Fernandez et al., "Synthesis of 2-Deoxy-3,5-di-O-benzoyl-2,2-difluoro-D-ribose from D-Giucose and D-Mannose. A Formal Synthesis of Gemcitabine," *Tetrahedron*, 1998, 54, 3523-3532.
Ferrandina et al., "Phase III Trial of Gemcitabine Compared With Pegylated Liposomal Doxorubicin in Progressive or Recurrent Ovarian Cancer," *J. Clin. Oncol.*, 2008, 26, 890-896.
Fox et al., "Nucleosides. XII. Direct Synthesis of 2'-Deoxycytidine and its α-Anomer," *J. Am. Chem. Soc.*, 1961, 83, 4066-4070.
Ge et al., "Synthesis of 2-Deoxy-2-halo-L-ascorbic Acids," *J. Org. Chem.*, 1997, 62, 3340-3343.
Genzyme, Genzyme 2007 Annual Report 2007.
Gruen et al., "2'Halo-ATP and -GTP analogues: Rational phasing tools for protein crystallography," *Protein Sci.* 1999, 8, 2524-2528.
Hagmann, W., "The Many Roles for Fluorine in Medicinal Chemistry," *J. Med. Chem.*, 2008, 51, 4359-4369.
Haigis et al., "SIRT4 Inhibits Glutamate Dehydrogenase and Opposes the Effects of Calorie Restriction in Pancreatic β Cells," *Cell*, 2006, 126, 941-954.
Hakme et al., "The expanding field of poly(ADP-ribosyl)ation reactions," *EMBO Rep.*, 2008, 9 1094-1100.
Handlon et al., "2'-Ribose Substituent Effects on the Chemical and Enzymatic Hydrolysis of NAD$^+$," *J. Am. Chem. Soc.*, 1994, 116, 12087-12088.
Harris et al., "2'-Deoxy-2'-halonucleotides as Alternate Substrates and Mechanism-Based Inactivators of *Lactobacillus leichmannii* Ribonucleotide Reductase," *Biochemistry*, 1987, 26, 1895-1902.
Harris et al., "Mechanism of Inactivation of *Escherichia coli* and Lactobacillus leichmannii Ribonucleotide Reductases by 2'-Chloro-2'-deoxynucleotides: Evidence for Generation of 2-Methylene-3(2H)-furanone," *Biochemistry*, 1984, 23, 5214-5225.
International Preliminary Report on Patentability and Written Opinion from the International Bureau in International Patent Application No. PCT/US2010/040816, mailed on Mar. 28, 2011.
Jackson et al., "Mechanism of Nicotinamide Inhibition and Transglycosidation by Sir2 Histone/Protein Deacetylases*," *J. Biol. Chem.*, 2003, 278, 50985-50998.
Jiang et al., "An Improved Preparation Process for Gemcitabine," *Org. Process Res. Dev.*, 2008, 12 (5), pp. 888-891.
Kirk, K, "Fluorination in Medicinal Chemistry: Methods, Strategies, and Recent Developments," *Org. Process Res. Dev.*, 2008, 12, 305-321.
Larsen et al., "Stereoselective C-Glycosylation Reactions of Ribose Derivatives: Electronic Effects of Five-Membered Ring Oxocarbenium Ions," *J. Am. Chem. Soc.*, 2005, 127, 10879-10884.
Liu et al., "Structural Basis for Enzymatic Evolution from a Dedicated ADP-ribosyl Cyclase to a Multifunctional NAD Hydrolase," *Chem. Biol.*, 2008, 15, 1068-1078.
Ma et al., "Update 1 of: Asymmetric Fluorination, Trifluoromethylation, and Perfluoroalkylation Reactions," *Chem. Rev.*, 2008, 108, PR1-PR43.

McAtee et al., "A Completely Diastereoselective Electrophilic Fluorination of a Chiral, Noncarbohydrate Sugar Ring Precursor: Application to the Synthesis of Several Novel 2'-Fluoronucleosides," *J. Org. Chem.*, 1998, 63, 2161-2167.
Mikhailopulo et al., "Oxidation-Reduction Sequence for the Synthesis of Peracylated Fluorodeoxypentofuranosides," *Nucleosides Nucleotides*, 1995, 14, 383-384.
Montgomery et al., "Synthesis and Biologic Activity of 2'-Fluoro-2-halo Derivatives of 9-β-$_D$-Arabinofuranosyladenine," *J Med. Chem.*, 1992, 35, 397-401.
Natalini et al., "Nicotinamide Mononucleotide Adenylyltransferase. Molecular and Enzymatic Properties of the Homogeneous Enzyme from Baker's Yeast," *Biochemistry*, 1986, 25, 3725-3729.
Nicolaou et al., "Adventures in Crbohydrate Chemistry: New Synthetic Technologies, Chemical Synthesis, Molecular Design, and Chemical Biology," *Angew. Chem. Int. Ed.*, 2001, 40, 1576-1624.
O'Hagan, D., "Understanding organofluorine chemistry. An introduction to the C—F bond," *Chem. Soc. Rev.*, 2008, 37(2), 308-319.
Pankiewicz, K., "Fluorinated nucleosides," *Carbohydr. Res.*, 2000, 327, 87-105.
Porter et al., "Identification of the Active Site Nucleophile in Nucleoside 2-Deoxyribosyltransferase as Glutamic Acid 98," *J. Biol. Chem.*, 1995, 270, 15551-15556.
Reichman et al., "A Practical Synthesis of 2-Deoxy-2-Fluoro-$_D$-Arabinofuranose Derviatives," *Carbohydr. Res.*, 1975, 42, 233-240.
Sauve et al., "A Covalent Intermediate in CD38 Is Responsible for ADP-Ribosylation and Cyclization Reactions," *J. Am. Chem. Soc.*, 2000, 122, 7855-7859.
Sauve et al., "The Biochemistry of Sirtuins," *Annu. Rev. Biochem.* 2006, 75, 435-465.
Silvestris et al., "Role of gemcitabine in metastic breast cáncer patients: A short review," *Breast*, 2008, 17, 220-226.
Sleath et al., "Pyridine Coenzyme Analogues. 3. Synthesis of Three NAD$^+$ Analogues Containing a 2'-Deoxy-2'-substituted Nicotinamide Arabinofuranosyl Moeity," *J. Org. Chem.*, 1991, 56, 3608-3613.
Smith et al., "Mechanisms and Molecular Probes of Sirtuins," *Chem. Biol.*, 2008, 15, 1002-1013.
Tewson et al., "New Approaches to the Synthesis of 3-Deoxy-3-fluoro-$_D$-glucose," *J. Org. Chem.*, 1978, 43, 1090-1092.
Tripp et al., "Reaction of Methylsilanols with Hydrated Silica Surfaces: The Hydrolysis of Trichloro-, Dichloro-, and Monocloromthelsilanes and the Effects of Curing," *Langmuir*, 1995, 11, 149-155.
Van Moorsel et al., "Gemcitabine: Furture Prospects of Single-Agent and Combination Studies," *Oncologist* 1997, 2, 127-134.
Vocadlo et al., "Catalysis by hen egg-shite lysozyme proceeds via a covalent intermiediate," *Nature*, 2001, 412, 835-838.
Vocadlo et al., "The chemical synthesis of 2-deoxy-2-fluorodisaccharide probes of the hen egg white lysozyme mechanism," *Carbohydr. Res.*, 2005, 340, 379-388.
Vulfovich et al., "Novel advances in pancreatic cancer treatment," *Expert Rev. Anticancer Ther.*, 2008, 8, 993-1002.
Watts et al., "2'F-Arabinonucleic acids (2'F-ANA)—History, properties, and new frontiers," *Can. J. Chem.*, 2008, 86, 641-656.
Welch et al., "Ester Enolate Claisen Rearrangements of Allyl α-Fluoroacetates and α-Fluoropropanoates," *J. Org. Chem.*, 1991, 56, 353-359.
Williams et al., "Glycosyl fluorides in enzymatic reactions," *Carbohydr. Res.*, 2000, 327, 27-46.
Wright et al., "Nucleosides. LX.[1a.] Fluorocarbohydrates. XXII.[1b.] Synthesis of 2-Deoxy-2-fluoro-$_D$-arabinoes and 9-(2-Deoxy-2-fluoro-α- and -β-$_D$-arabinofuranosyl)adenines," *J. Org. Chem.*, 1969, 34, 2632-2636.
Zechel et al., "Dissection of nucleophilic and acid-base catalysis in glycosidases," *Curr. Opin. Chem. Biol.*, 2001, 5, 643-649.

* cited by examiner

FIG. 55
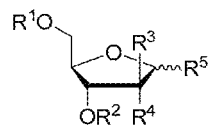
$R^1$ = ADP   $R^2$ = H   $R^3$ = F   $R^4$ = H
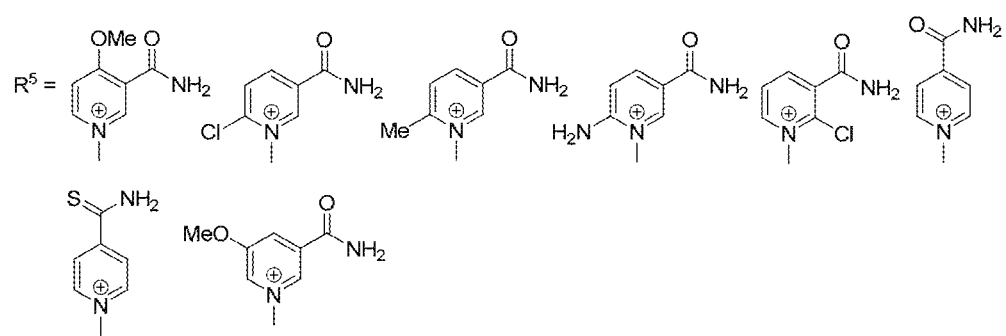

FIG. 56
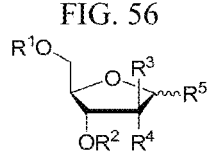
$R^1$ = ADP  $R^2$ = H  $R^3$ = H  $R^4$ = F
$R^5$ =
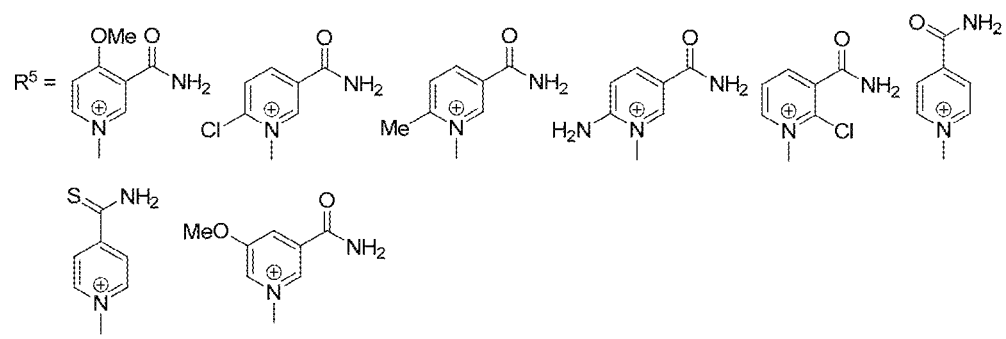

2-FLUORINATED RIBOSES AND ARABINOSES AND METHODS OF USE AND SYNTHESIS

CROSS-REFERENCE TO RELATED APPLICATIONS

This patent application is the U.S. national phase of International Patent Application PCT/US2010/040816, filed Jul. 1, 2010, which claims the benefit of U.S. Provisional Patent Application No. 61/222,424, filed Jul. 1, 2009, which are incorporated by reference in their entireties.

BACKGROUND OF THE INVENTION

The efficient introduction of fluorine atoms into bioactive organic molecules has attracted considerable attention in recent years owing to the unique properties of the fluorine substituent. (Refs. 1-4) The selective replacement of hydrogen or oxygen with fluorine can change a compound's biological activity, metabolic stability, chemical stability, lipophilicity, acidity and dipole properties with modest change in steric bulk. (Refs 2-4) A broad class of particularly relevant compounds are the fluorinated carbohydrates (Refs. 1, 5, 6) and nucleosides. (Refs. 1, 3, 4) Selective fluorination in the sugar moiety of glycosides or nucleosides has proven useful to numerous investigations of enzyme mechanism where either sugars or nucleosides are substrates. (Refs. 6-14) Some of these compounds are potent drugs. For example, gemcitabine (Gemzar, Eli Lilly, 2'-deoxy-2',2'-difluorocytidine) is used clinically to treat numerous cancers including ovarian (Ref. 15), pancreatic (Ref. 16), and breast (Ref. 17) cancers, with sales in excess of 1.6 billion dollars per year (Ref. 18). Of the mono-substituted 2'-fluoro-nucleosides, clofarabine (Clorar, Genzyme, 2-Chloro-2'-deoxy-2'-fluoro-arabino-adenosine), has been approved for pediatric patients with relapsed or refractory acute lymphocytic leukemia (Ref. 19) and annual sales now exceed 100 million dollars (Ref. 20).

Previous studies have demonstrated that 2'-deoxy-2'-fluoro-arabino-nicotinamide-mononucleotide is a potent mechanism-based inhibitor (apparent $K_i$=61 nM) of the signaling enzyme cell developmental protein 38 (CD38) (Refs. 10, 12). The 2'-fluoro-NAD$^+$s and related compounds are likely to be valuable for the study of sirtuin enzyme mechanism (Refs. 11, 21), and for studying the chemical properties of poly-ADP-ribosylpolymerases (Ref. 22). Fluorinated NAD$^+$s could be useful for identifying ADP-ribosyltransfer sites on proteins as well. For example, it has been demonstrated that the 2'-deoxy-2'-fluoro-arabino-furanosyl modification is suitably robust for MS/MS approaches used to characterize amino acid post-translational modifications (Ref. 10). ADP-ribosylation sites are poorly surveyed within the proteome and yet these modifications are of heightened interest as they are implicated in important biological effects (Refs. 22-24). The synthesis of 2'-deoxy-2'-fluoro-arabino-NAD$^+$ was previously described (Ref. 25), but syntheses of 2'-deoxy-2'-fluoro-ribo-NAD$^+$ and 2'-deoxy-2',2'-difluoro-NAD$^+$ or their nucleoside precursors have not appeared in the literature. The difluoro derivatives in particular are useful, based upon their chemical stability and altered electronic properties.

Methods to synthesize the 2-deoxy-2-fluoro-D-furanose precursors to 2'-fluorinated nucleosides have not experienced substantial recent innovation (Refs. 1, 3, 26) despite the fact that unmet need for these compounds has only increased in recent years. The synthetic methods currently available vary in efficiency and all depend on routes relying on different initial precursors to the respective final products. For example, the best method to make a protected 2-deoxy-2-fluoro-arabino-furanose requires only 2 steps from a protected ribose in 58% overall yield (Refs. 25, 27, 28, 29). On the other hand, 2-deoxy-2-fluoro-ribofuranose has no concise or efficient synthesis (Ref. 30) and still requires 6 steps from arabinose (Ref. 31). Alternatively, 2-deoxy-2-fluoro-ribofuranose can be obtained via a 10-step non-diastereoselective method in 11% overall yield (Refs. 32-34). An efficient but non-diastereoselective route has been established for the synthesis of protected 2-deoxy-2,2-difluoro ribonofuranose in 5 steps via coupling of ethyl-bromodifluoroacetate and isopropylidene glyceraldehyde. The route is not diastereoselective and depends upon crystallization of the preferred isomer (Ref. 35). This procedure was developed by Eli Lilly for commercial synthesis of gemcitabine. 2-Deoxy-2,2-difluororibofuranose can also be obtained stereoselectively from glucose or mannose (Ref 36), but that method involves 8 steps and very low overall yield (<15%).

In view of the foregoing, there is a desire to provide novel halogenated 2-deoxy nucleosides and method for the synthesis thereof.

BRIEF SUMMARY OF THE INVENTION

The invention provides a compound of formula (I):

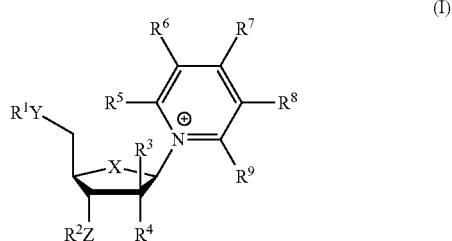

wherein $R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

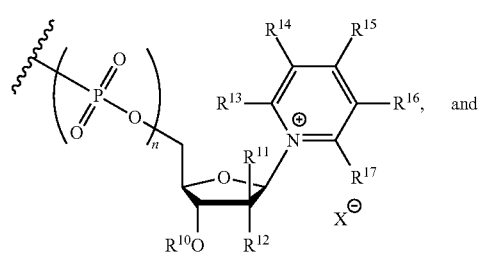

-continued

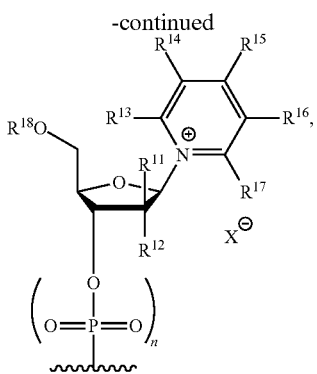

R² is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

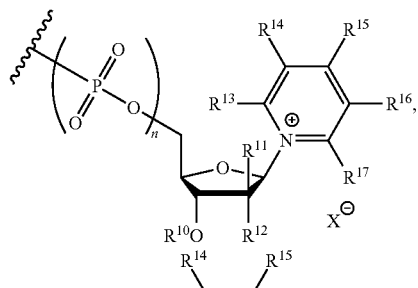

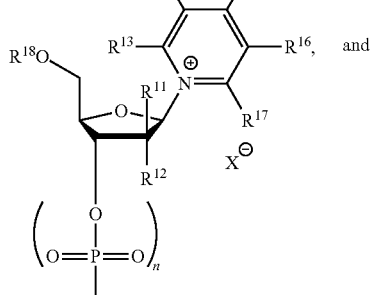

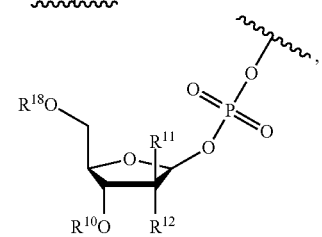

X, X', Y, Y', Z, and Z' are independently selected from the group consisting of O, S, Se, NH, and $CHR^{23}$, $R^3$ and $R^4$ are independently selected from the group consisting of hydrogen, F, Cl, Br, and I, with the proviso that $R^3$ and $R^4$ are not both hydrogen, n is 1 or 2, $R^8$ is selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, each of $R^5$, $R^6$, $R^7$, $R^9$, $R^{13}$, $R^{14}$, $R^{15}$, and $R^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, F, Cl, Br, and I, $R^{23}$ is selected from the group consisting of hydrogen, alkyl, alkoxy, alkenyl, alkenyloxy, alkynyl, alkynyloxy, aryl, heteroaryl, cycloalkyl, and heterocycloalkyl, and X⁻ is an anion, with the provisos that when $R^1$ is hydrogen, phosphate, or diphosphate, $R^2$, $R^5$, $R^6$, $R^7$, and $R^9$ are hydrogen and $R^8$ is $CONH_2$, $R^3$ is not fluoro and $R^4$ is not hydrogen, and when $R^1$, $R^2$, $R^5$, $R^6$, $R^7$, and $R^9$ are hydrogen and $R^8$ is $CONH_2$, $R^3$ is not hydrogen and $R^4$ is not fluoro, or a pharmaceutically acceptable salt thereof.

The invention also provides a method of synthesizing the compound of formula (II):

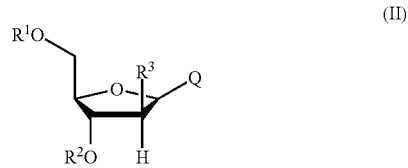

(II)

wherein Q and Q' are independently selected from the group consisting of $C_6$-$C_{10}$ aryl, $C_5$-$C_{10}$ heteroaryl, $C_5$-$C_{10}$ heterobicycloaryl, $C_5$-$C_{10}$ heterocyclyl, $C_5$-$C_{10}$ heterobicyclyl, each optionally substituted by 1, 2, 3, 4, or 5 substituents selected from the group consisting of halo, =O, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_6$-$C_{10}$ aryl, heteroaryl, $C_1$-$C_6$ haloalkyl, $C_1$-$C_6$ dihaloalkyl, $C_1$-$C_6$ trihaloalkyl, $—NO_2$, —OH, $—OR^{23}$, —SH, $—SR^{23}$, $—SOR^{23}$, $—SO_2R^{23}$, $—COR^{23}$, —COOH, $—COOR^{23}$, $—CONH_2$, $—CONHR^{23}$, $—CONHR^{23}R^{24}$, and

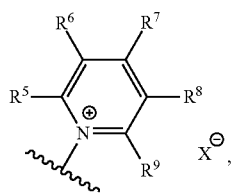

$R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

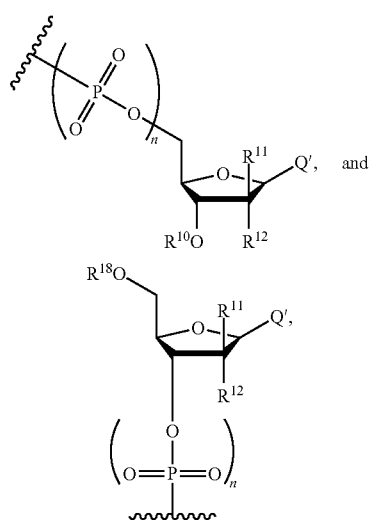

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

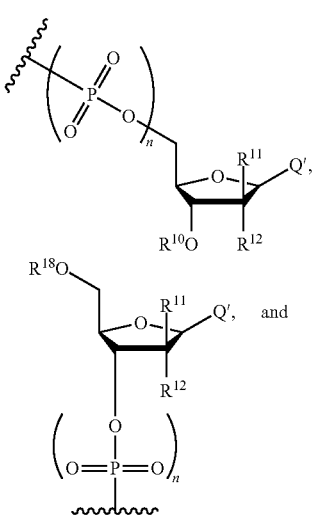

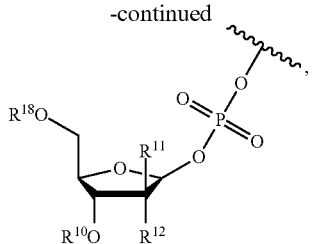

$R^3$ is F or Cl, n is 1 or 2, $R^8$ is selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, $R^5$, $R^6$, $R^7$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, hydroxy, F, Cl, Br, and I, $R^{23}$ and $R^{24}$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_3$-$C_8$ cycloalkenyl, and $X^-$ is an anion, comprising the steps of:

(i) providing a compound of formula (III):

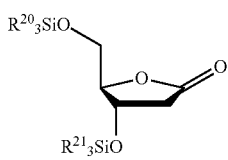

(III)

wherein each $R^{20}$ and $R^{21}$ are independently selected from the group consisting of $C_1$-$C_6$ alkyl and $C_6$-$C_{10}$ aryl, (ii) treating the compound of formula (III) with a base and a fluorinating or a chlorinating agent to provide a compound of formula (IV):

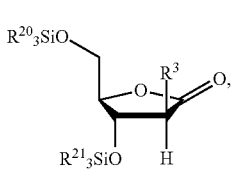

(IV)

(iii) treating the compound of formula (IV) with a reducing agent to provide a compound of formula (V):

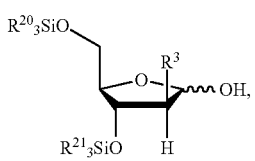

(V)

and (iv) converting the compound of formula (V) into the compound of formula (II).

The invention additionally provides a method of synthesizing the compound of formula (VI):

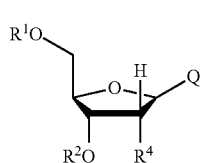

(VI)

wherein Q and Q' are independently selected from the group consisting of $C_6$-$C_{10}$ aryl, $C_5$-$C_{10}$ heteroaryl, $C_5$-$C_{10}$ heterobicycloaryl, $C_5$-$C_{10}$ heterocyclyl, $C_5$-$C_{10}$ heterobicyclyl, each optionally substituted by 1, 2, 3, 4, or 5 substituents selected from the group consisting of halo, =O, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_6$-$C_{10}$ aryl, heteroaryl, $C_1$-$C_6$ haloalkyl, $C_1$-$C_6$ dihaloalkyl, $C_1$-$C_6$ trihaloalkyl, —$NO_2$, —OH, —$OR^{23}$, —SH, —$SR^{23}$, —$SOR^{23}$, —$SO_2R^{23}$, —$COR^{23}$, —COOH, —$COOR^{23}$, —$CONH_2$, —$CONHR^{23}$, —$CONHR^{23}R^{24}$, and

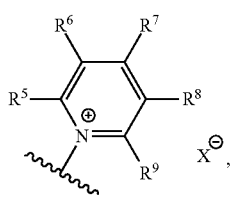

$R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

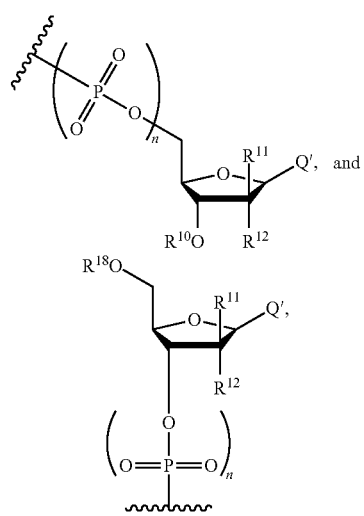

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

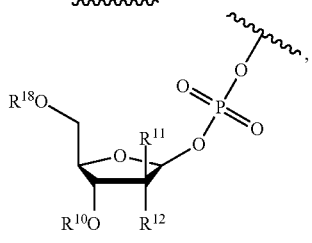

$R^4$ is F or Cl, n is 1 or 2, $R^8$ is selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, $R^5$, $R^6$, $R^7$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, hydroxy, F, Cl, Br, and I, $R^{23}$ and $R^{24}$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_3$-$C_8$ cycloalkenyl, and $X^-$ is an anion, comprising the steps of:

(i) providing a compound of formula (III):

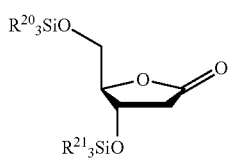

(III)

wherein each $R^{20}$ and $R^{21}$ are independently selected from the group consisting of $C_1$-$C_6$ alkyl and $C_6$-$C_{10}$ aryl, (ii) treating the compound of formula (III) with a base and a silylating agent to provide a compound of formula (VII):

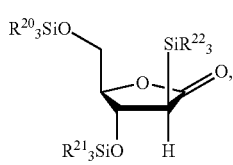

(VII)

wherein each $R^{22}$ is independently selected from the group consisting of $C_1$-$C_6$ alkyl and $C_6$-$C_{10}$ aryl, (iii) treating the compound of formula (VII) with a base and a fluorinating or a chlorinating agent to provide a compound of formula (VIII):

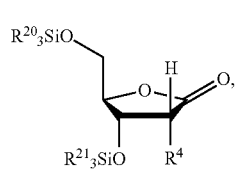

(VIII)

(iv) treating the compound of formula (VIII) with a reducing agent to provide a compound of formula (IX):

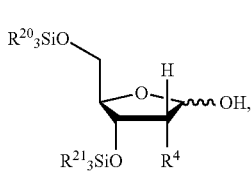

(IX)

and (v) converting the compound of formula (IX) into the compound of formula (VI).

The invention further provides a method of synthesizing the compound of formula (X):

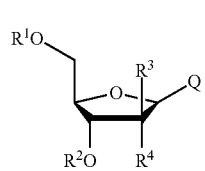

(X)

wherein Q and Q' are independently selected from the group consisting of $C_6$-$C_{10}$ aryl, $C_5$-$C_{10}$ heteroaryl, $C_5$-$C_{10}$ heterobicycloaryl, $C_5$-$C_{10}$ heterocyclyl, $C_5$-$C_{10}$ heterobicyclyl, each optionally substituted by 1, 2, 3, 4, or 5 substituents selected from the group consisting of halo, =O, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_6$-$C_{10}$ aryl, heteroaryl, $C_1$-$C_6$ haloalkyl, $C_1$-$C_6$ dihaloalkyl, $C_1$-$C_6$ trihaloalkyl, $-NO_2$, $-OH$, $-OR^{23}$, $-SH$, $-SR^{23}$, $-SOR^{23}$, $-SO_2R^{23}$, $-COR^{23}$, $-COOH$, $-COOR^{23}$, $-CONH_2$, $-CONHR^{23}$, $-CONHR^{23}R^{24}$, and

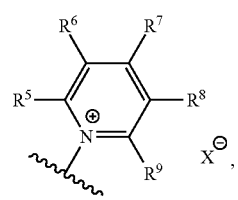

$R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

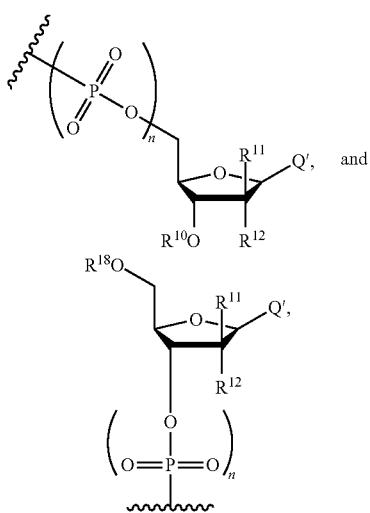

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

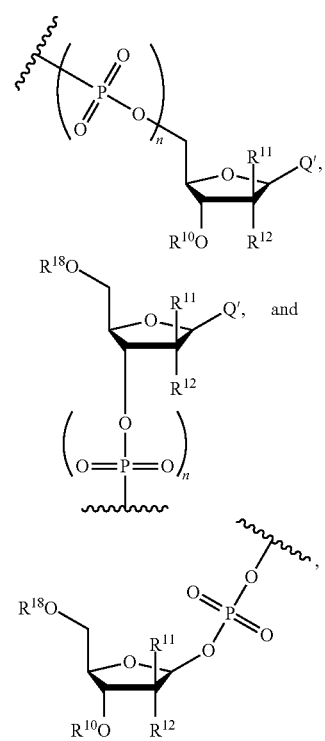

$R^3$ and $R^4$ are independently F or Cl, n is 1 or 2, $R^8$ is selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, $R^5$, $R^6$, $R^7$, and $R^9$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, hydroxy, F, Cl, Br, and I, $R^{23}$ and $R^{24}$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_3$-$C_8$ cycloalkenyl, and $X^-$ is an anion, comprising the steps of:

(i) providing a compound of formula (IV):

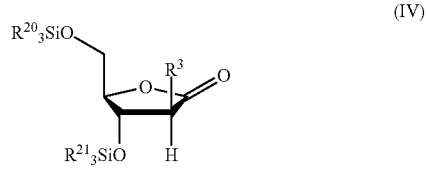

wherein each $R^{20}$ and $R^{21}$ are independently selected from the group consisting of $C_1$-$C_6$ alkyl and $C_6$-$C_{10}$ aryl and wherein $R^3$ is F or Cl, (ii) treating the compound of formula (IV) with a base and a fluorinating or a chlorinating agent to provide a compound of formula (XI):

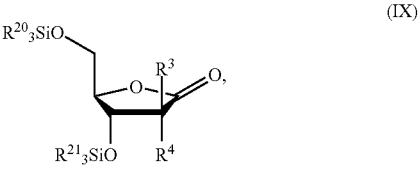

(iii) treating the compound of formula (XI) with a reducing agent to provide a compound of formula (XII):

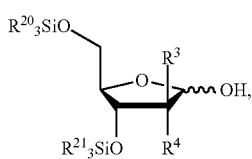

(XII)

and (iv) converting the compound of formula (XII) into the compound of formula X.

BRIEF DESCRIPTION OF THE SEVERAL VIEWS OF THE DRAWING(S)

Figure 17:
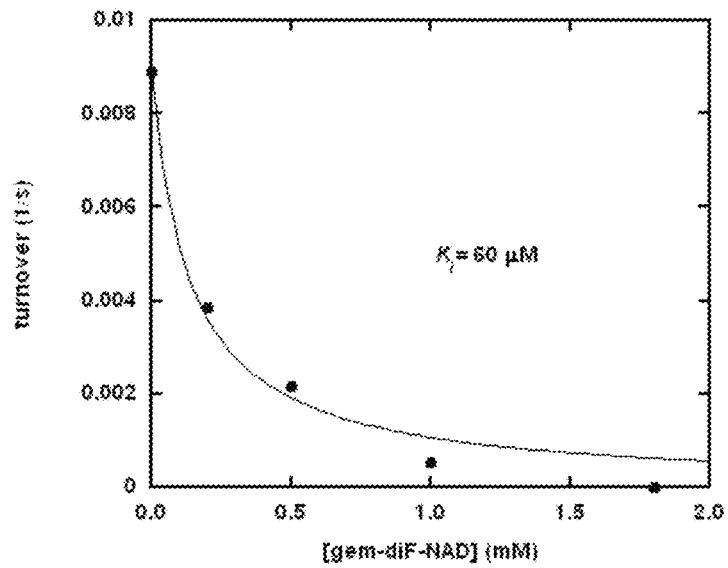

FIG. 17 inhibition of SirT1 activity by gem-diF-NAD.

Figure 18:
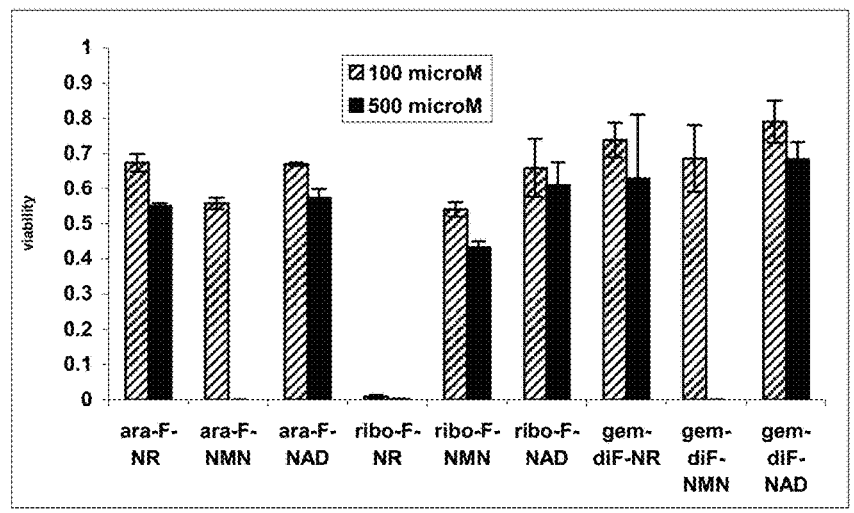

FIG. 18 illustrates toxicity of 2'-deoxy-2'-fluoro-nucleosides and nucleotides on HEK293 cells.

Figure 19:
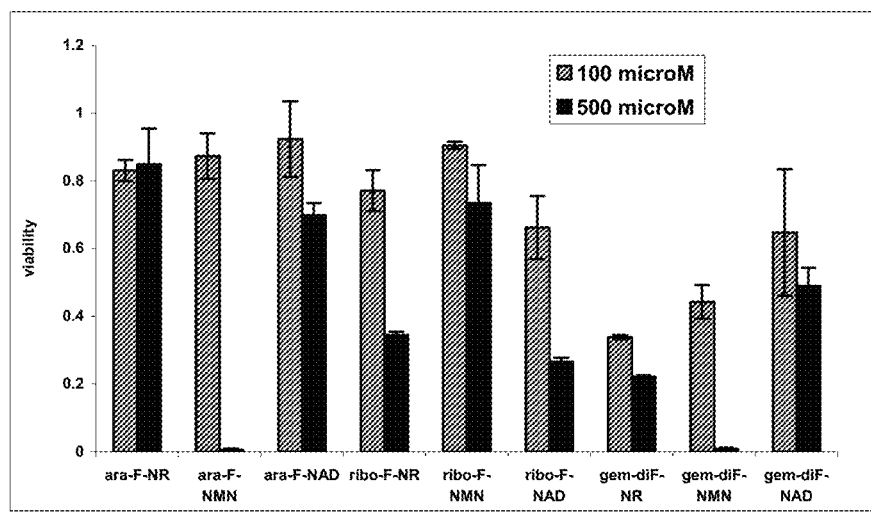

FIG. 19 illustrates toxicity of 2'-deoxy-2'-fluoro-nucleosides and nucleotides on Neuro2A cells.

Figure 20:
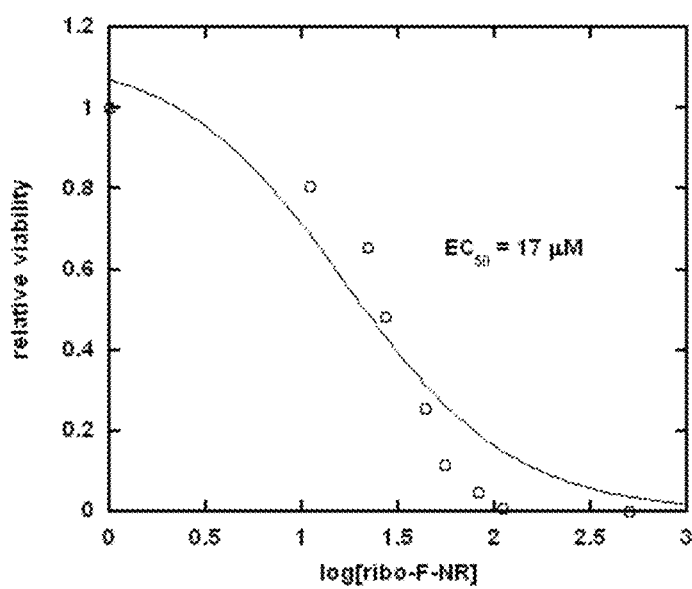

FIG. 20 illustrates RIbo-F-NR dose response in HEK293 cells.

Figure 21:
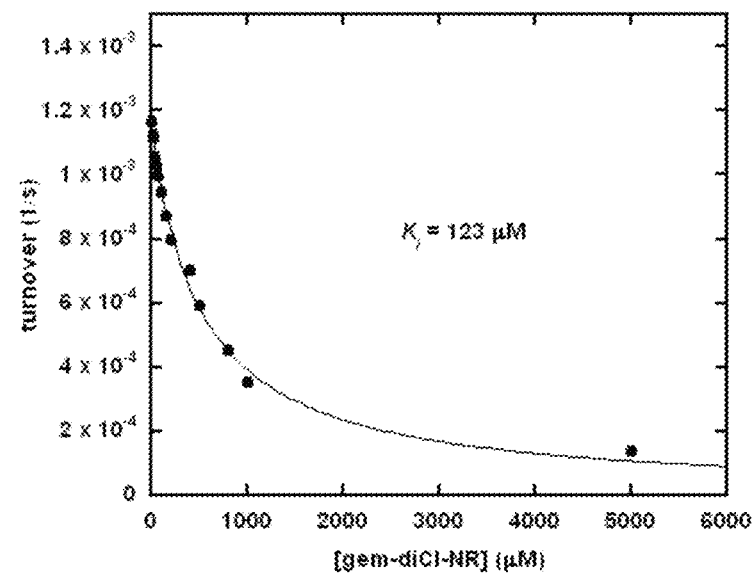

FIG. 21 illustrates gem-diCl-NR inhibition of SirT3.

Figure 22:
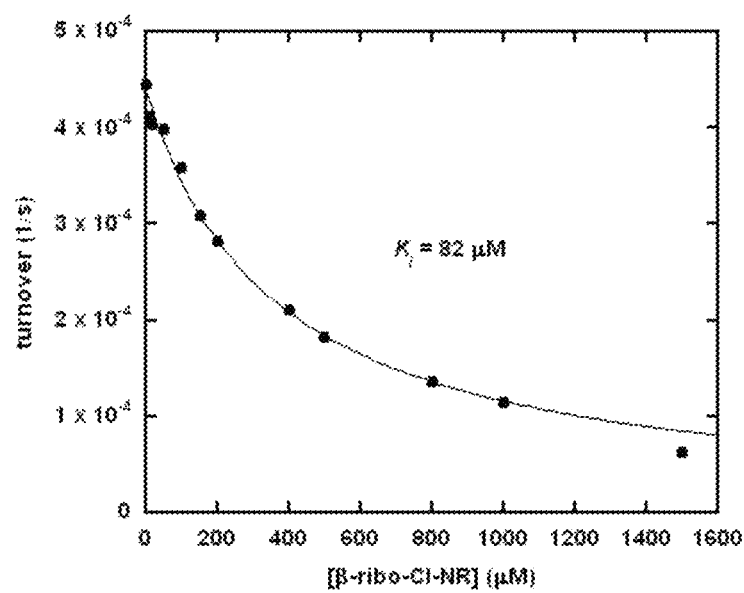

FIG. 22 illustrates β-ribo-Cl-NR inhibition of SirT3.

Figure 23:
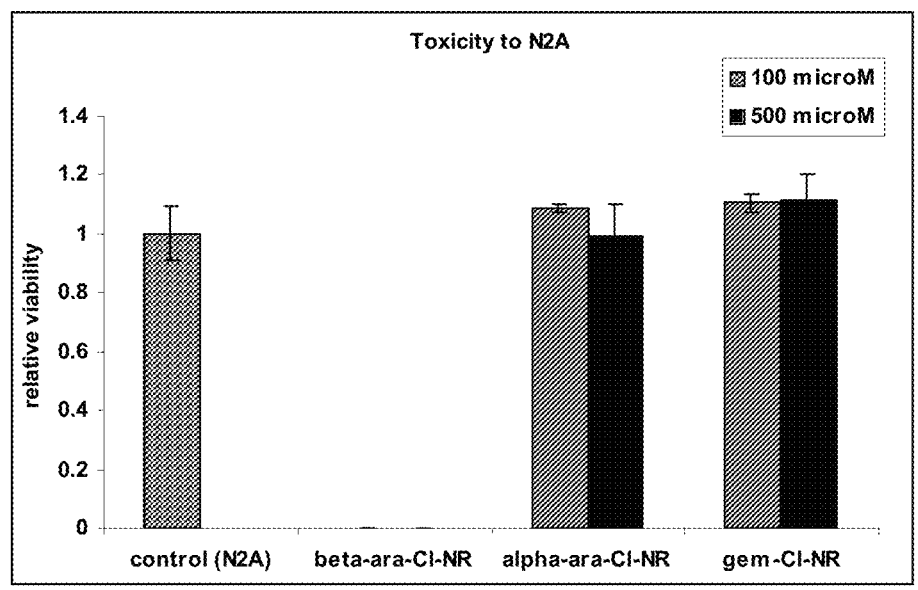

FIG. 23 illustrates toxicity of 2'-deoxy-2'-fluoro-nucleosides to Neuro2A cells.

Figure 24:
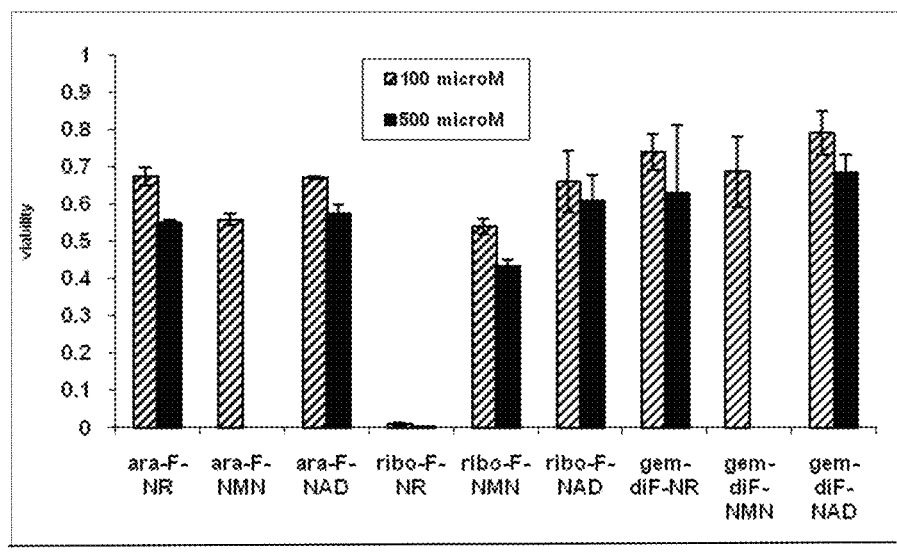

FIG. 24 illustrates toxicity of 2'-deoxy-2'-fluoro-nucleosides to HEK293 cells.

Figure 25:
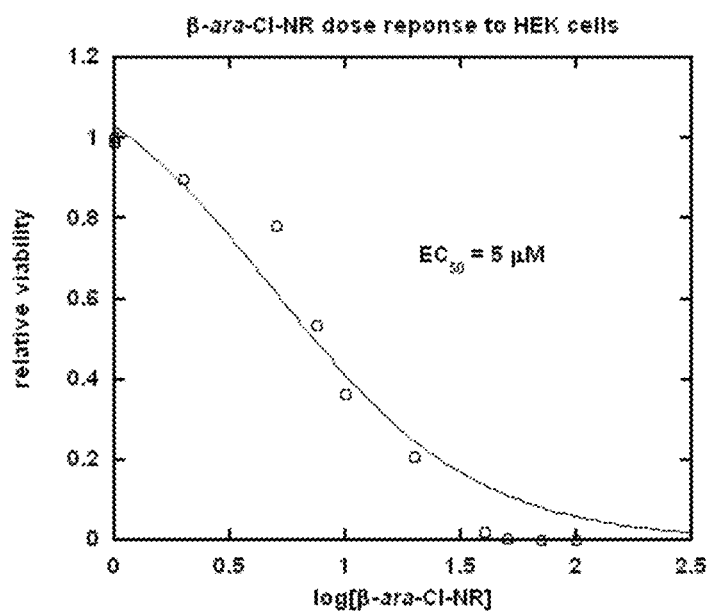

FIG. 25 illustrates β-ara-Cl-NR dose response to HEK293 cells.

Figure 26:
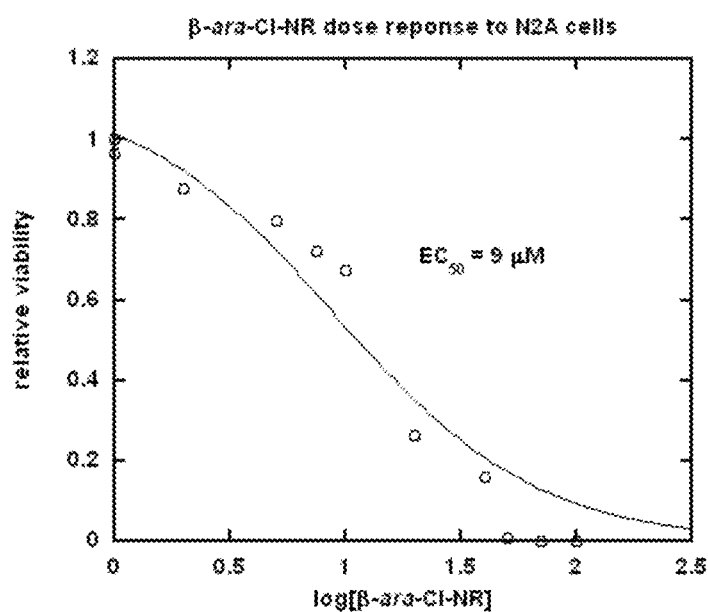

FIG. 26 illustrates β-ara-Cl-NR dose response to Neuro2A cells.

Figure 27:
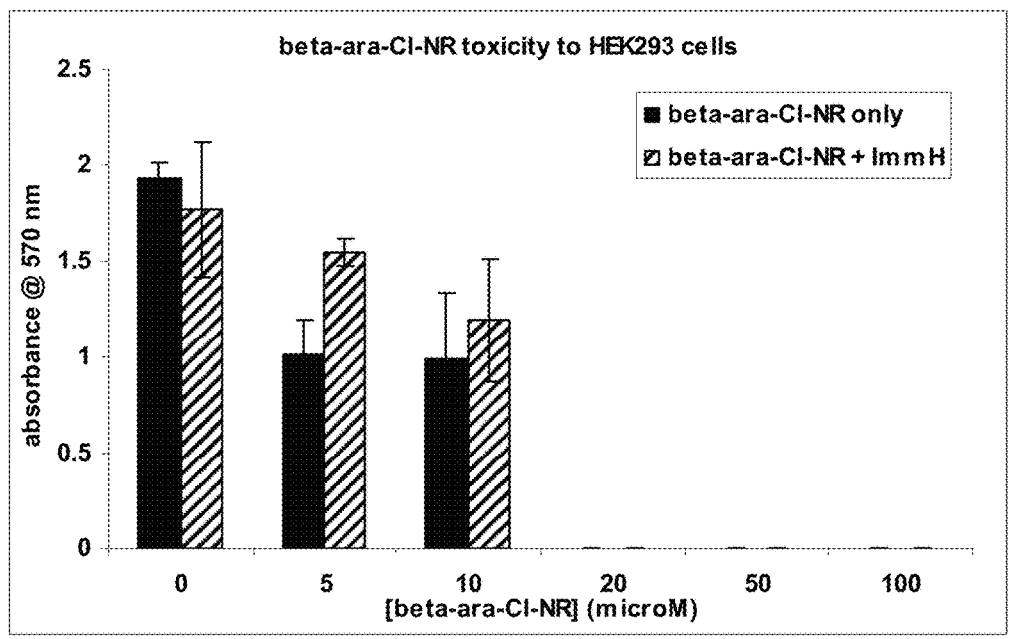

FIG. 27 illustrates β-ara-Cl-NR dose response to HEK293 cells with and without Immucillin-H.

Figure 28:
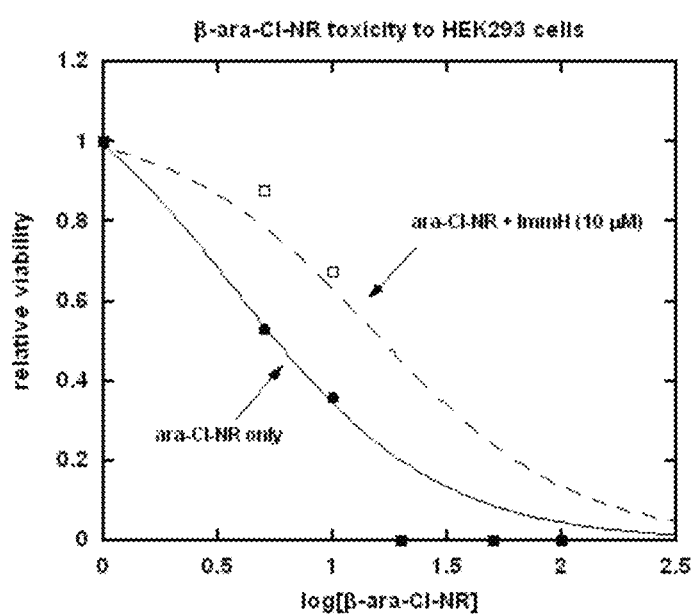

FIG. 28 illustrates β-ara-Cl-NR dose response to HEK293 cells with and without Immucillin-H.

Figure 29:
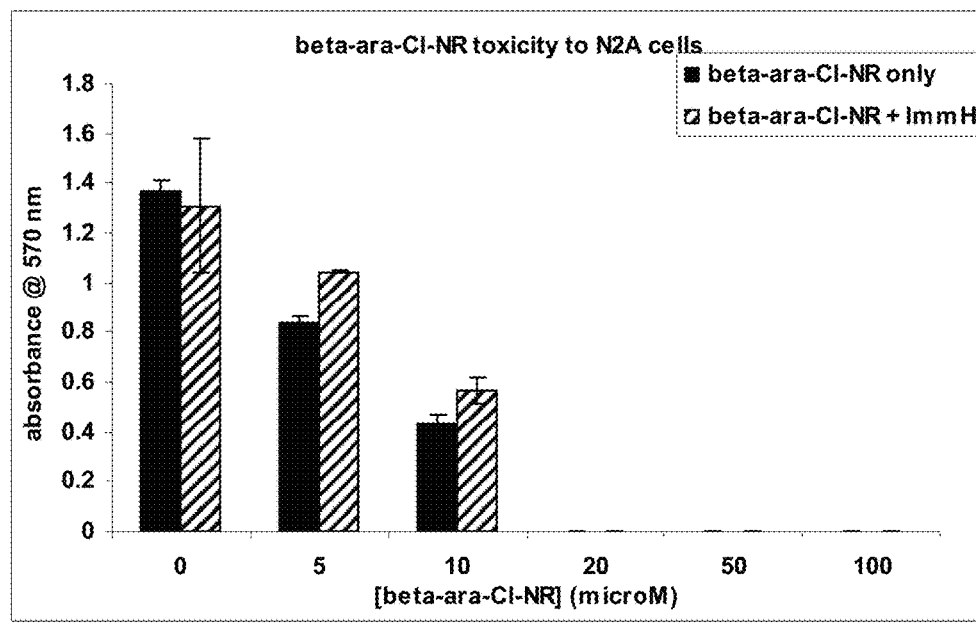

FIG. 29 illustrates β-ara-Cl-NR dose response to Neuro2A cells with and without Immucillin-H.

Figure 30:
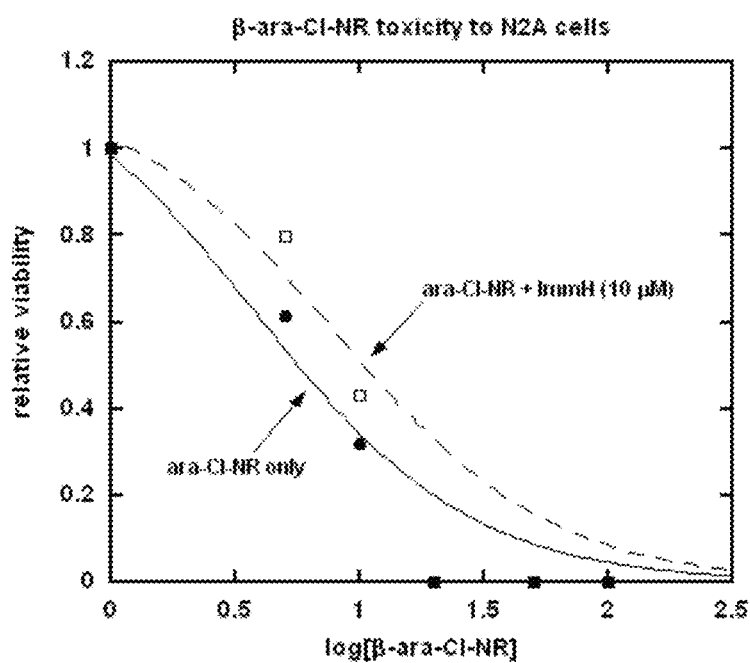

FIG. 30 illustrates β-ara-Cl-NR dose response to Neuro2A cells with and without Immucillin-H.

Figure 31:
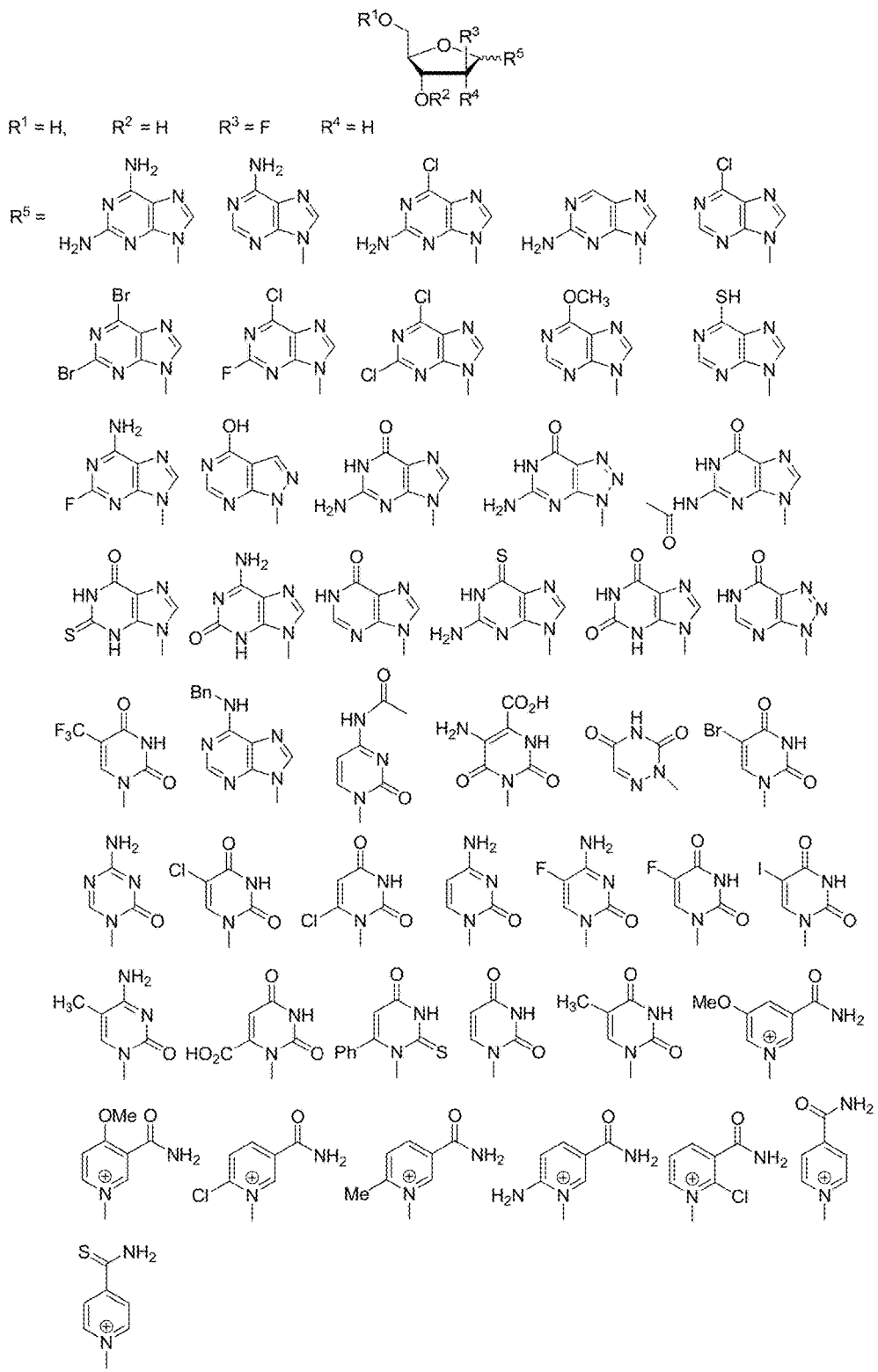

FIG. 31 illustrates specific 2'-deoxy-2'-fluoro-arabino-nucleosides.

Figure 32:
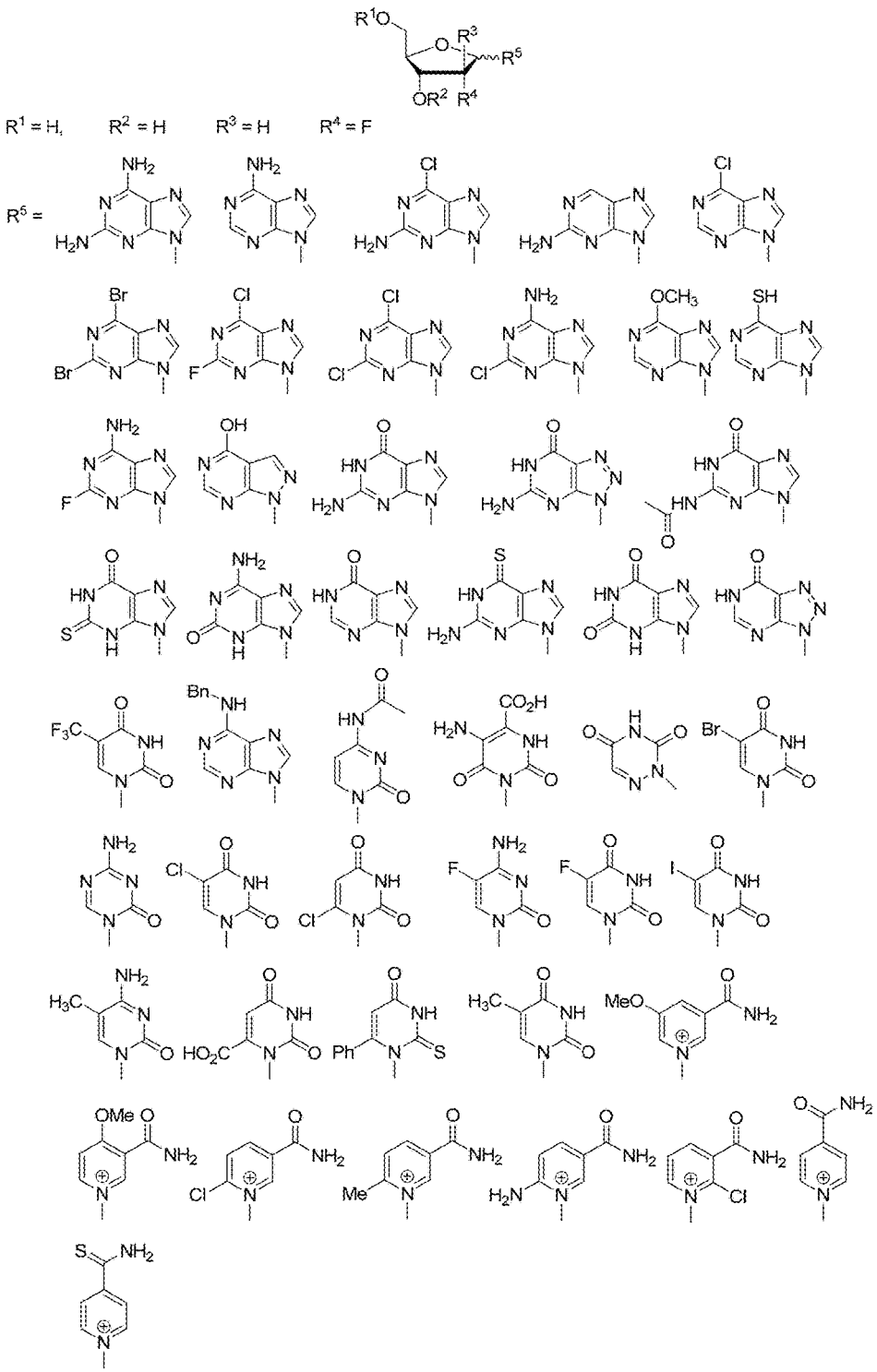

FIG. 32 illustrates specific 2'-deoxy-2'-fluoro-ribo-nucleosides.

Figure 33:
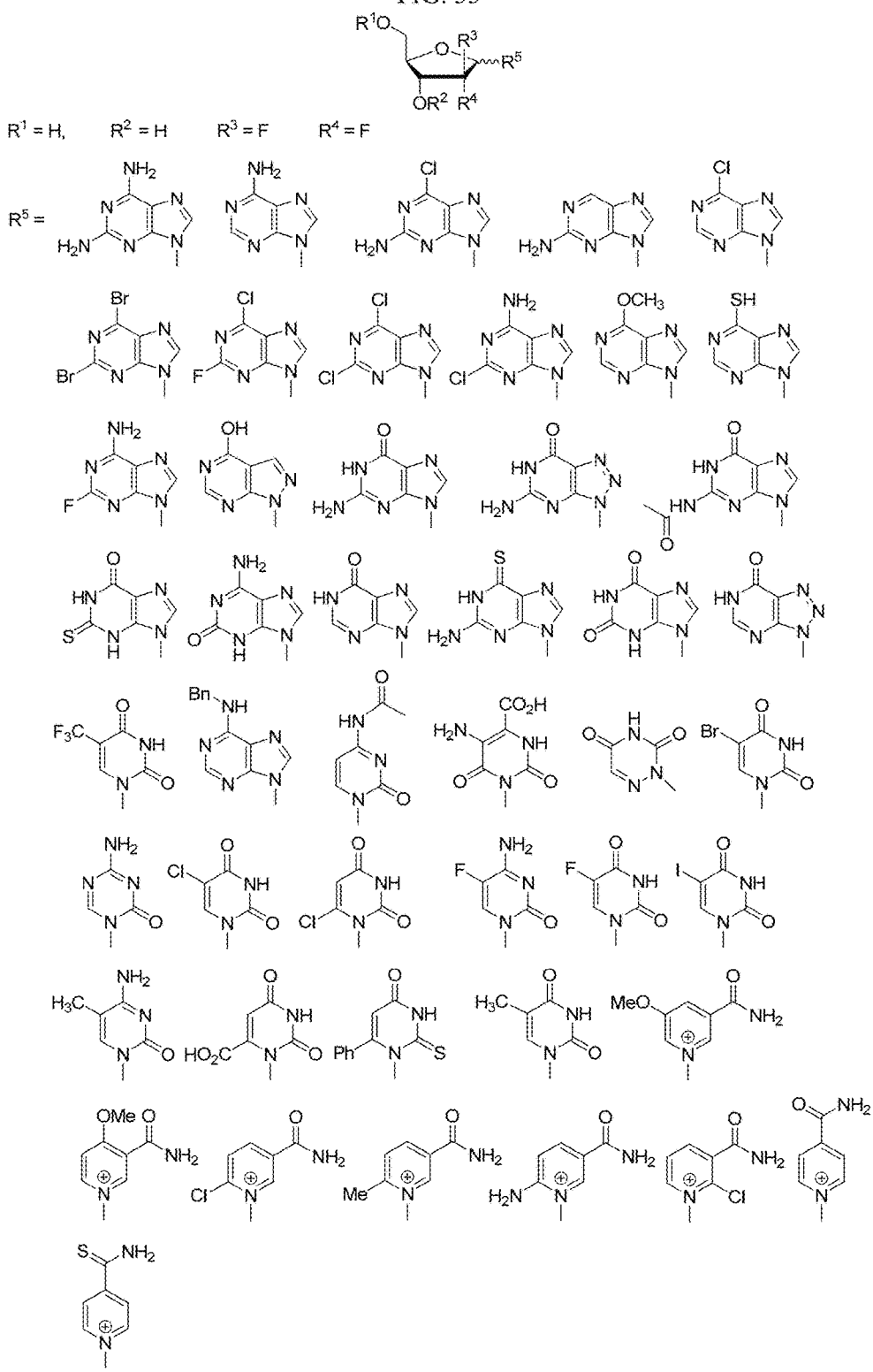

FIG. 33 illustrates specific 2'-deoxy-2',2'-difluoronucleosides.

Figure 34:
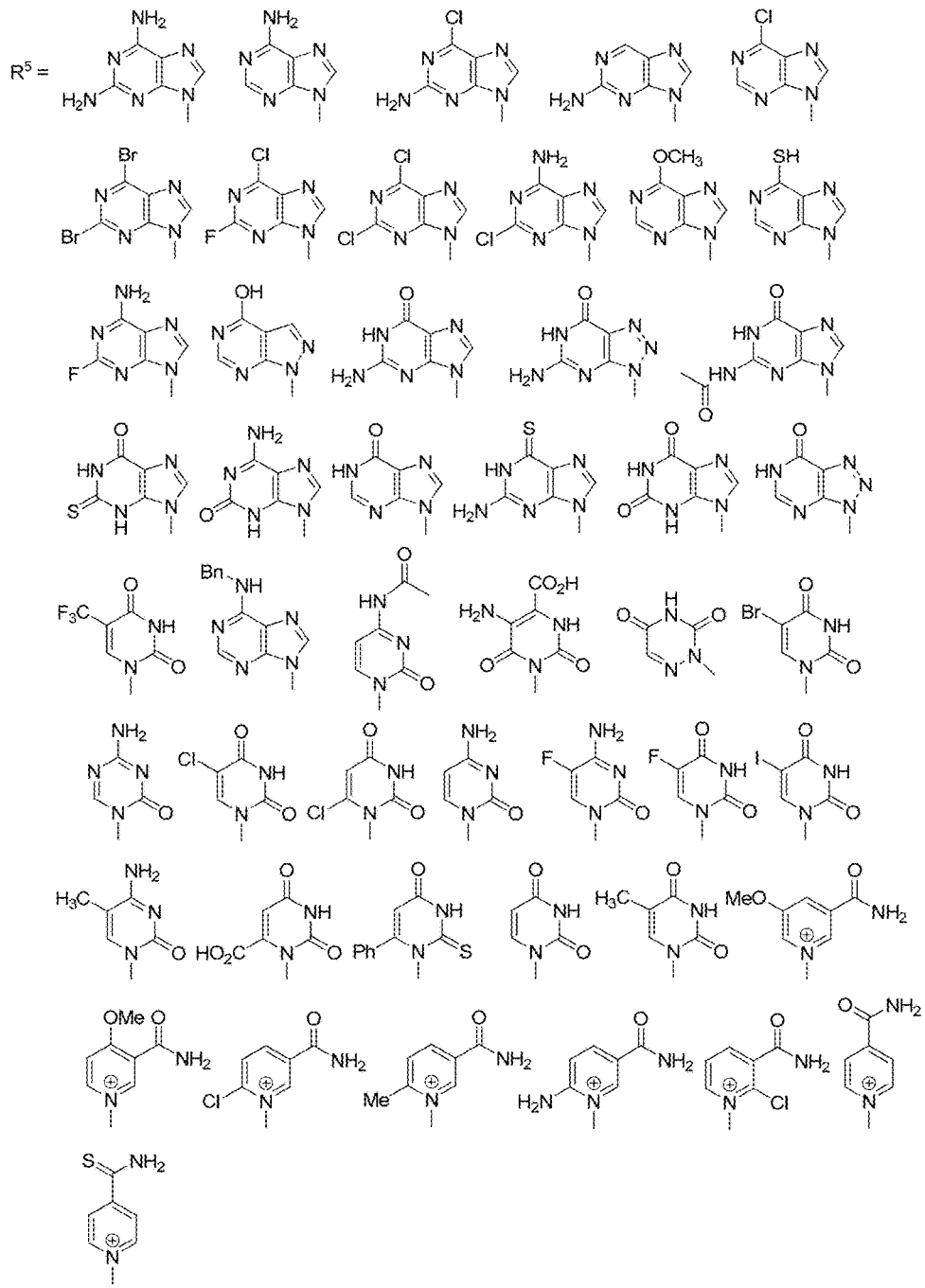

FIG. 34 illustrates specific 2'-deoxy-2'-fluoro-arabino-nucleoside-5'-phosphates.

Figure 35:
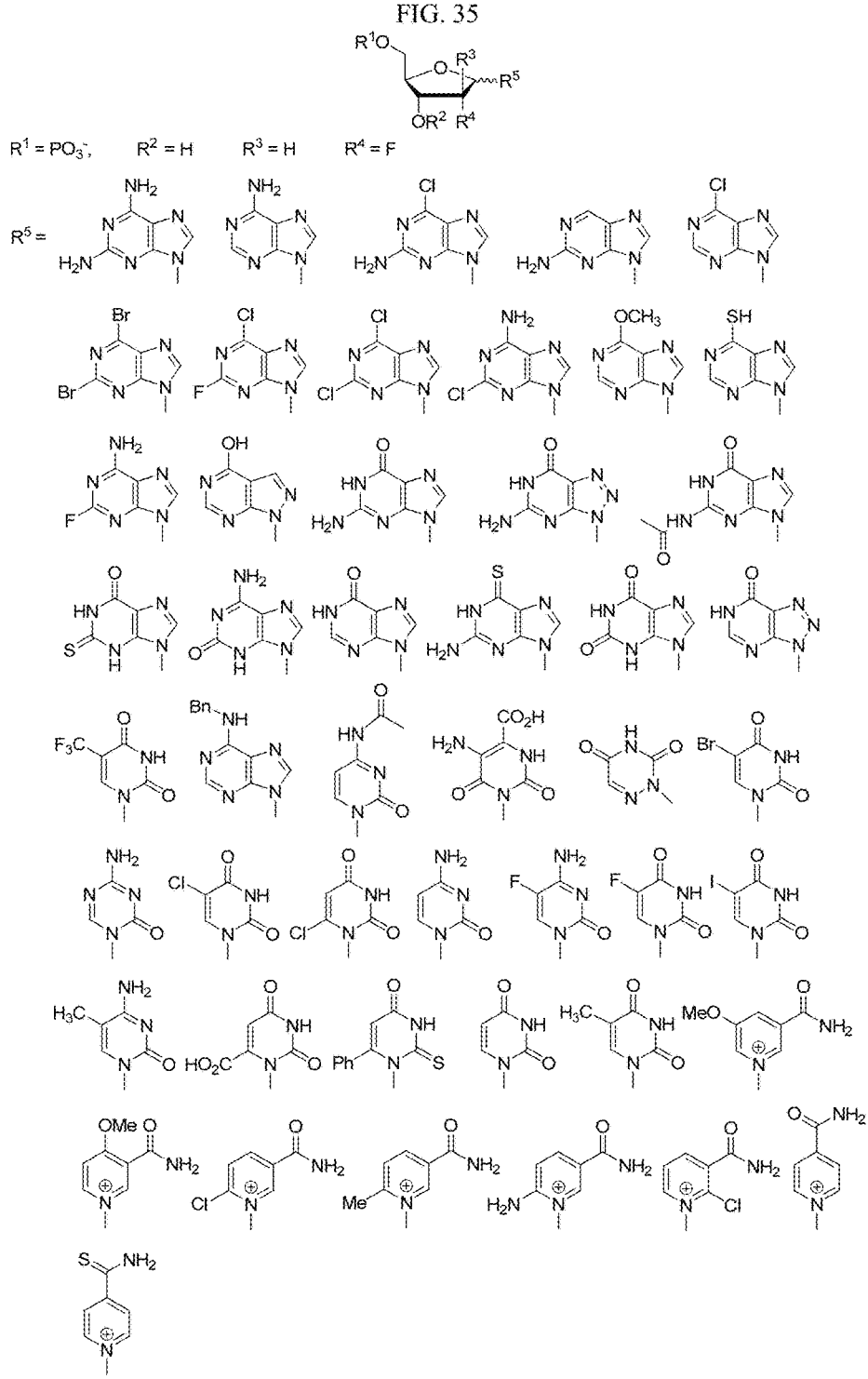

FIG. 35 illustrates specific 2'-deoxy-2'-fluoro-ribo-nucleoside-5'-phosphates.

Figure 36:
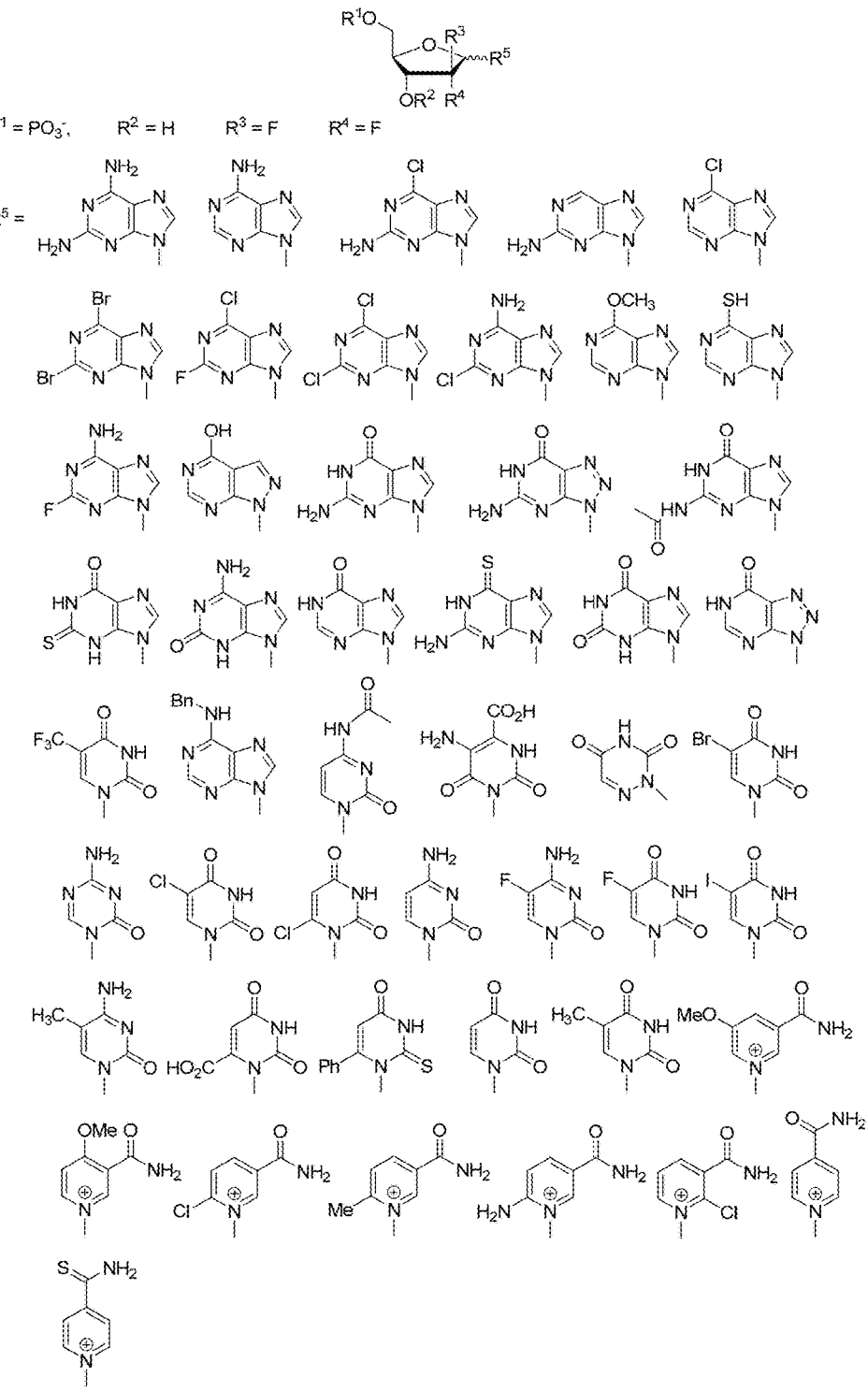

FIG. 36 illustrates specific 2'-deoxy-2',2'-difluoronucleoside-5'-phosphates.

Figure 37:
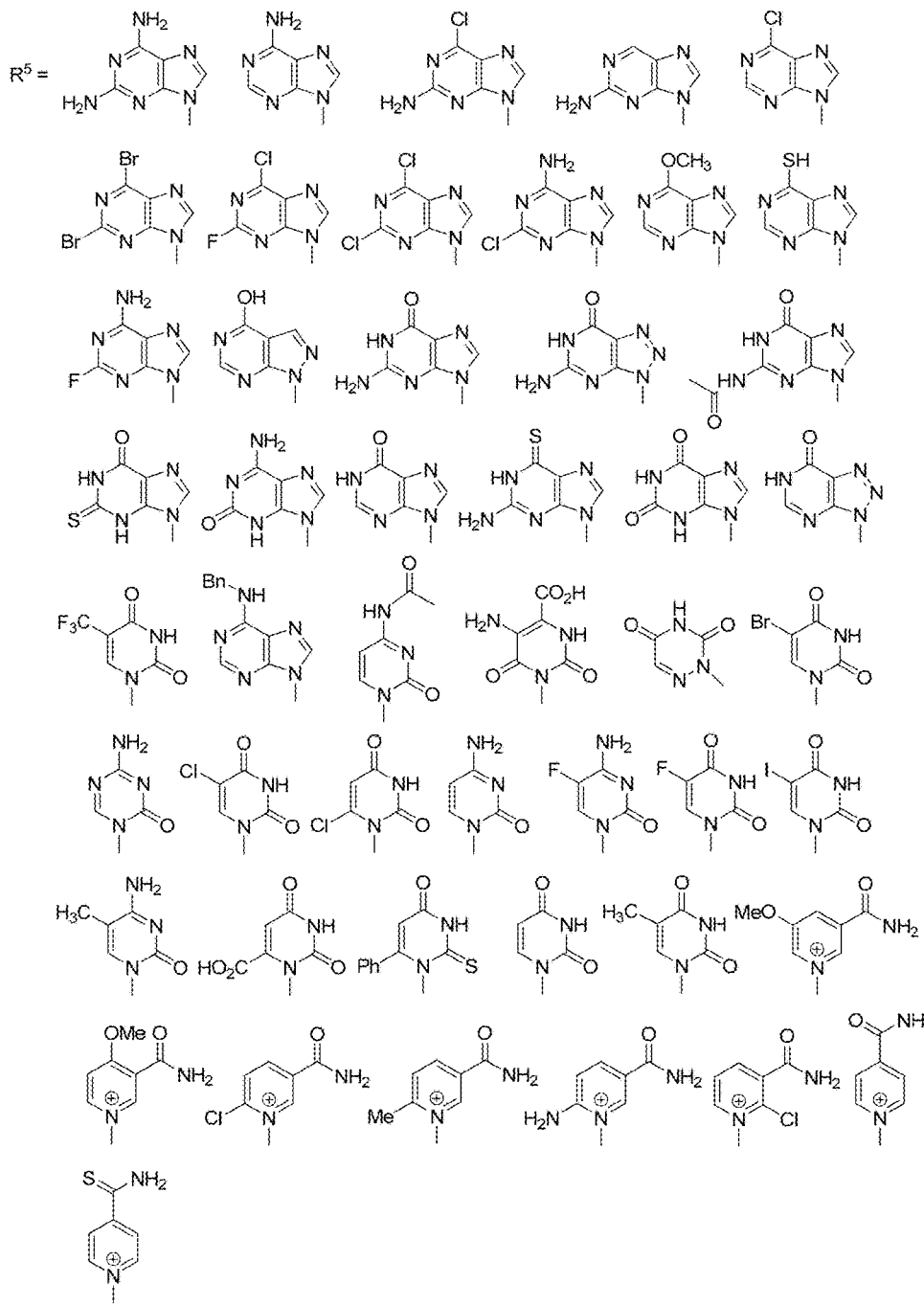

FIG. 37 illustrates specific 2'-deoxy-2'-fluoro-arabino-nucleoside-3'-phosphates.

Figure 38:
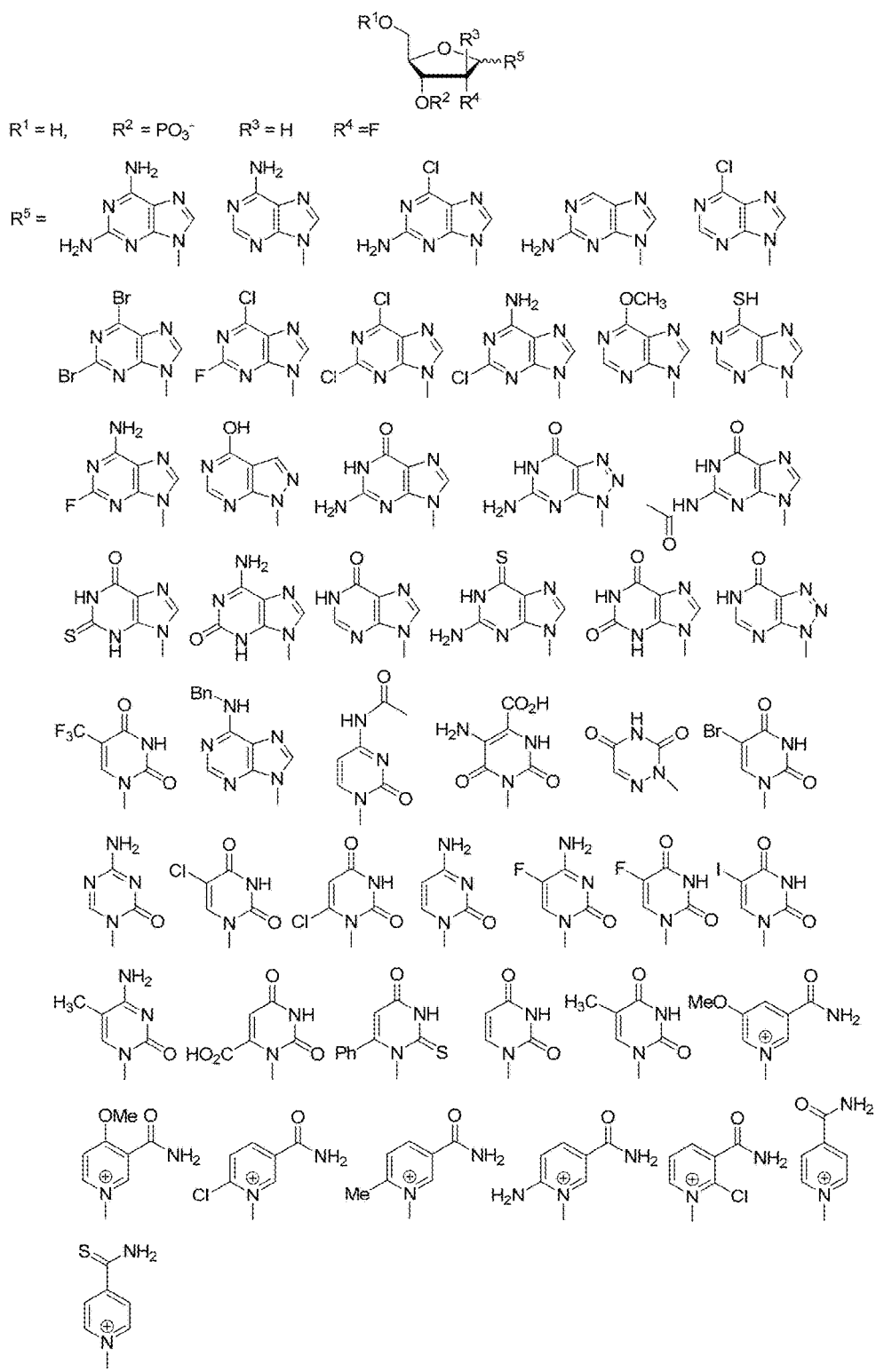

FIG. 38 illustrates specific 2'-deoxy-2'-fluoro-ribo-nucleoside-3'-phosphates.

Figure 39:
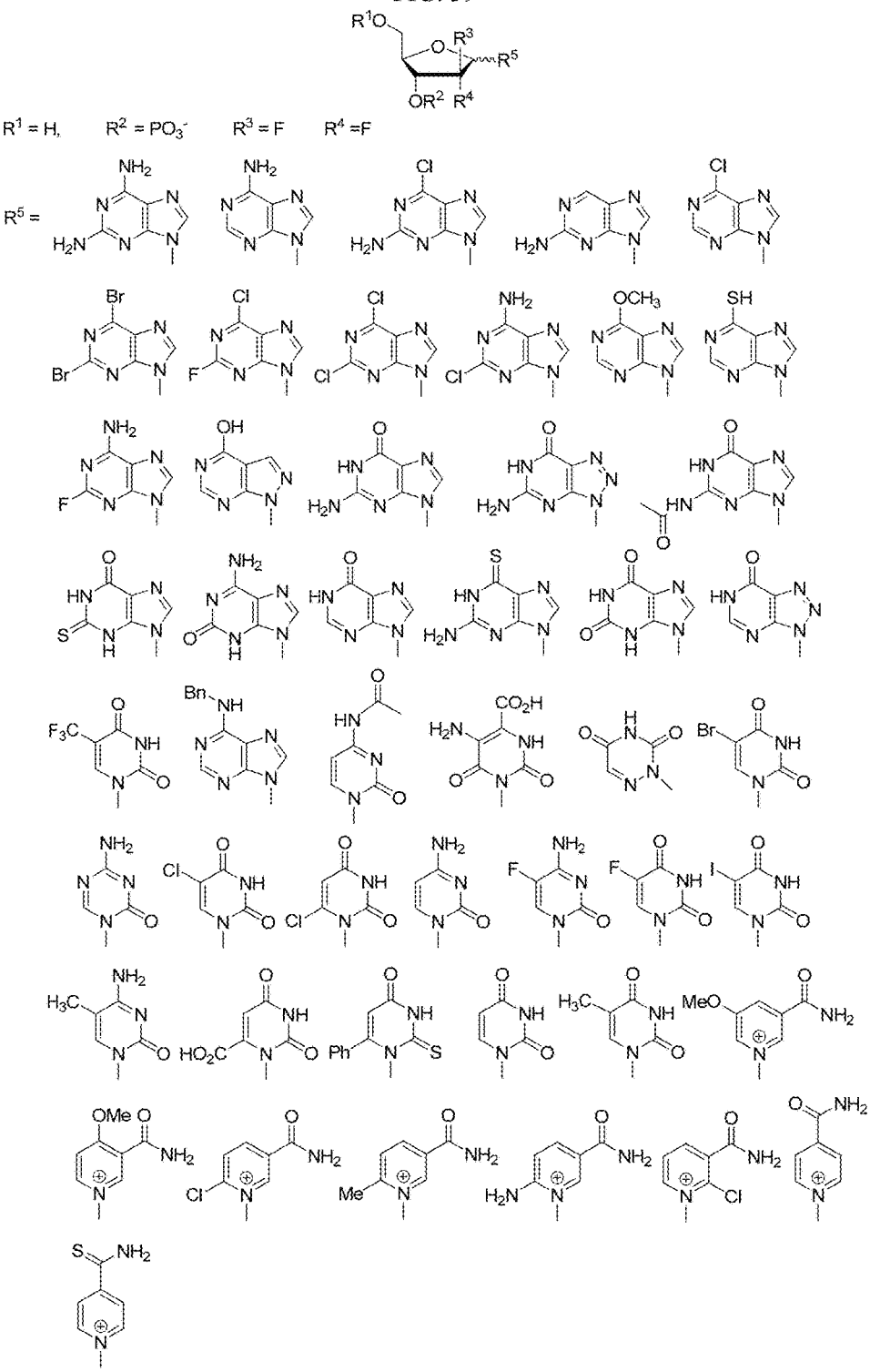

FIG. 39 illustrates specific 2'-deoxy-2',2'-difluoronucleoside-3'-phosphates.

Figure 40:
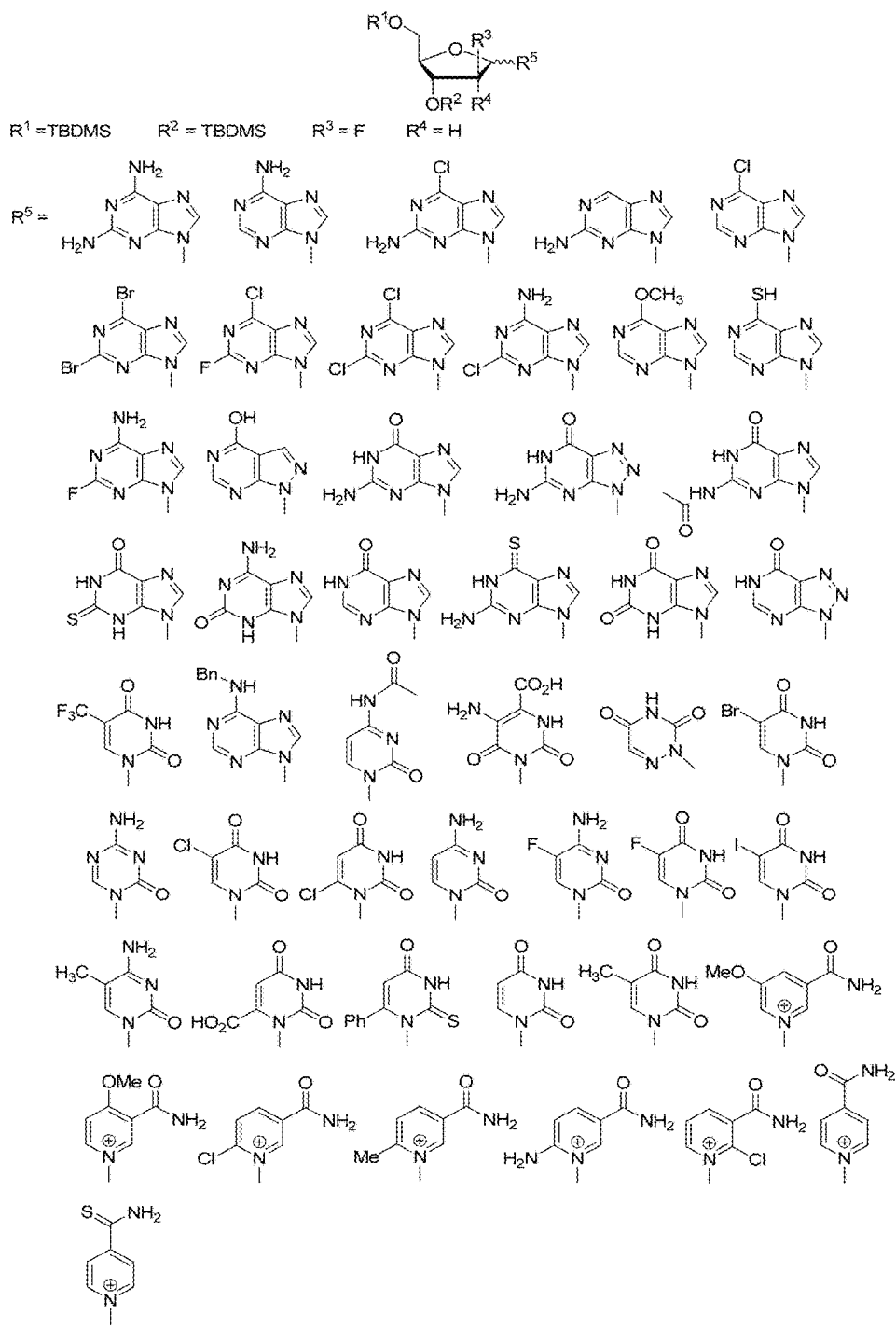

FIG. 40 illustrates specific 3',-5'-bis(TBDMS)-2'-deoxy-2'-fluoro-arabino-nucleosides.

Figure 41:
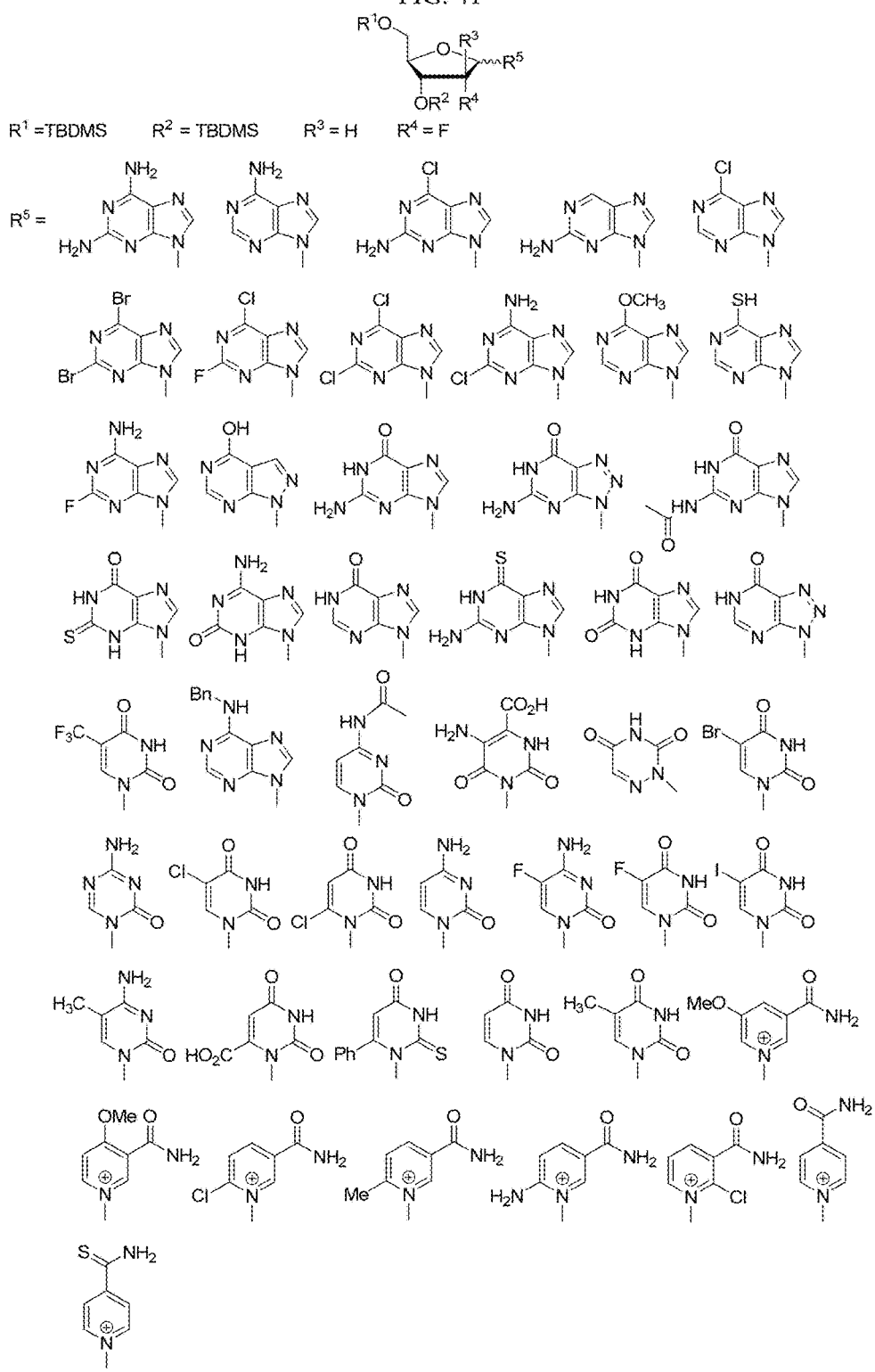

FIG. 41 illustrates specific 3',-5'-bis(TBDMS)-2'-deoxy-2'-fluoro-ribo-nucleosides.

Figure 42:
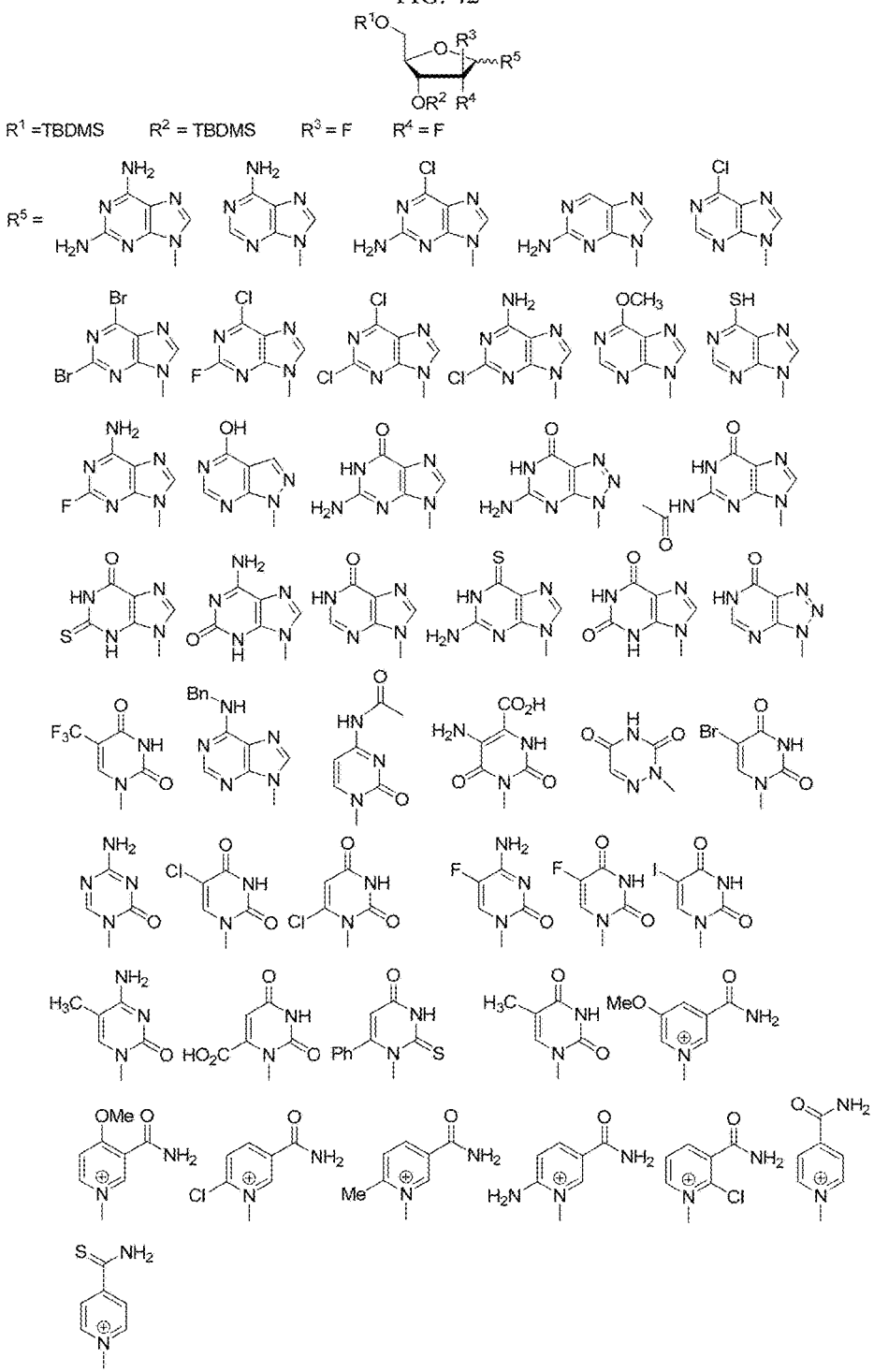

FIG. 42 illustrates specific 3',-5'-bis(TBDMS)-2'-deoxy-2',2'-difluoronucleosides.

Figure 43:
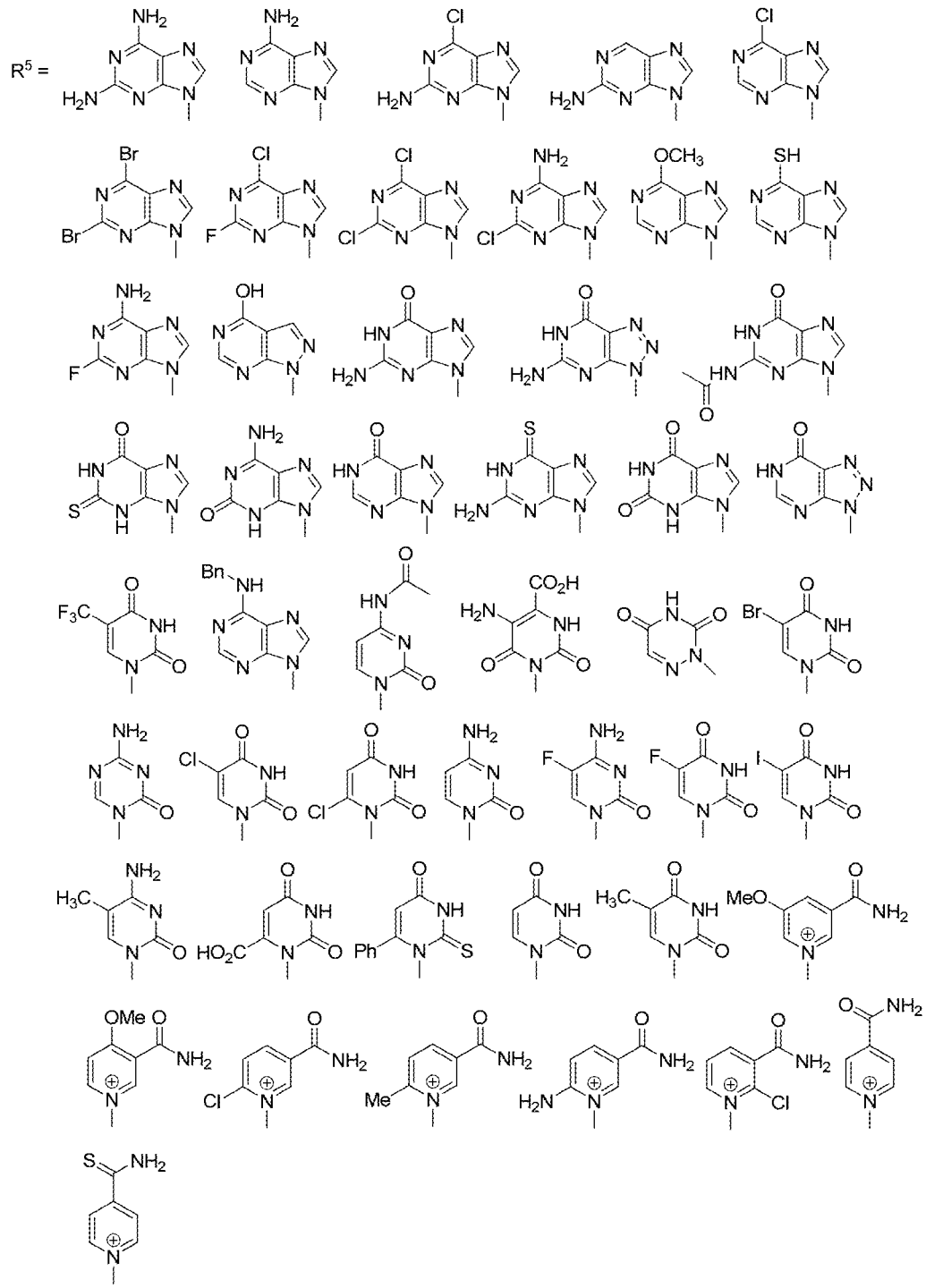

FIG. 43 illustrates specific 3',-5'-bis(TIPS)-2'-deoxy-2'-fluoro-arabino-nucleosides.

Figure 44:
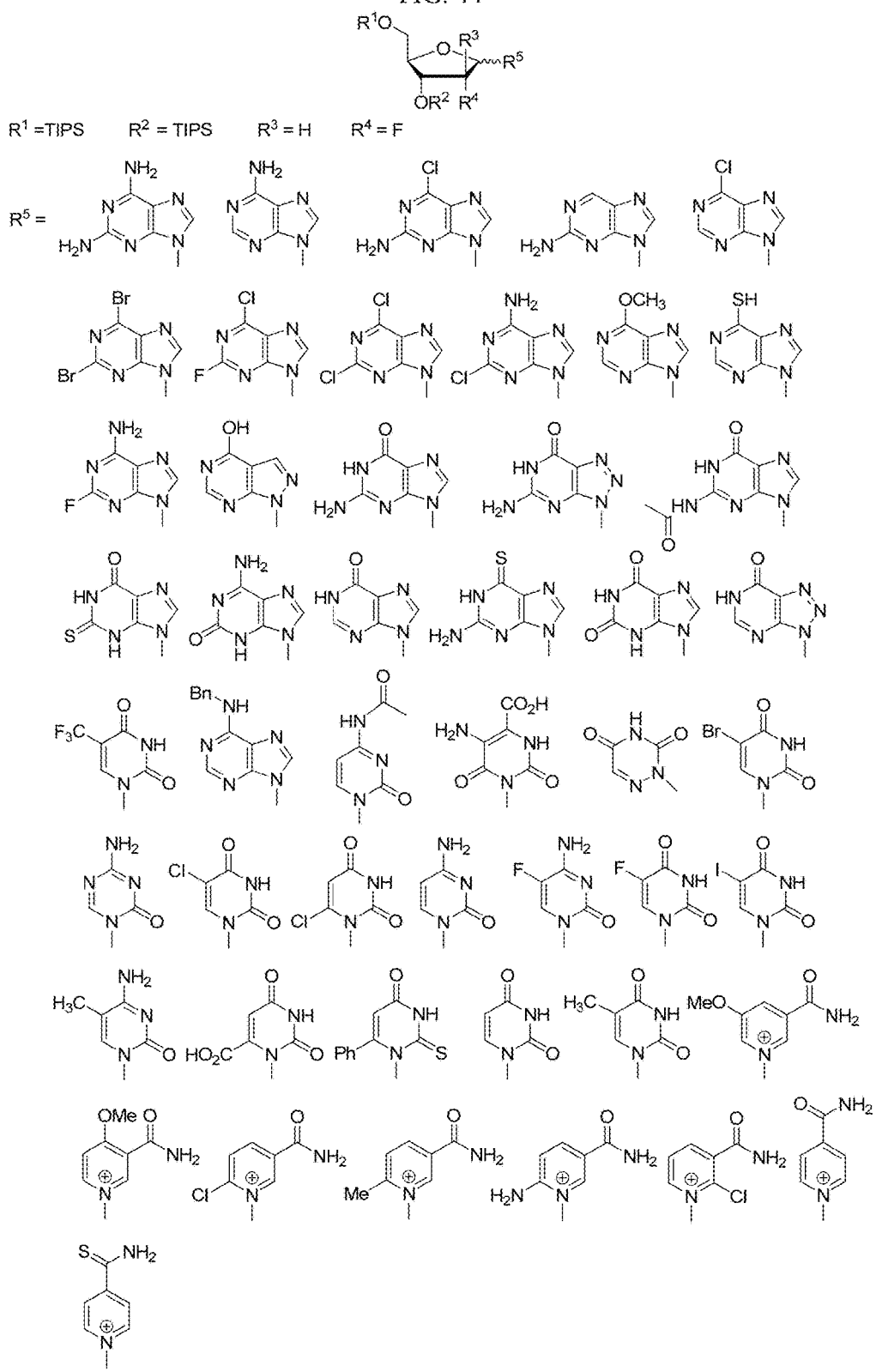

FIG. 44 illustrates specific 3',-5'-bis(TIPS)-2'-deoxy-2'-fluoro-ribo-nucleosides.

Figure 45:
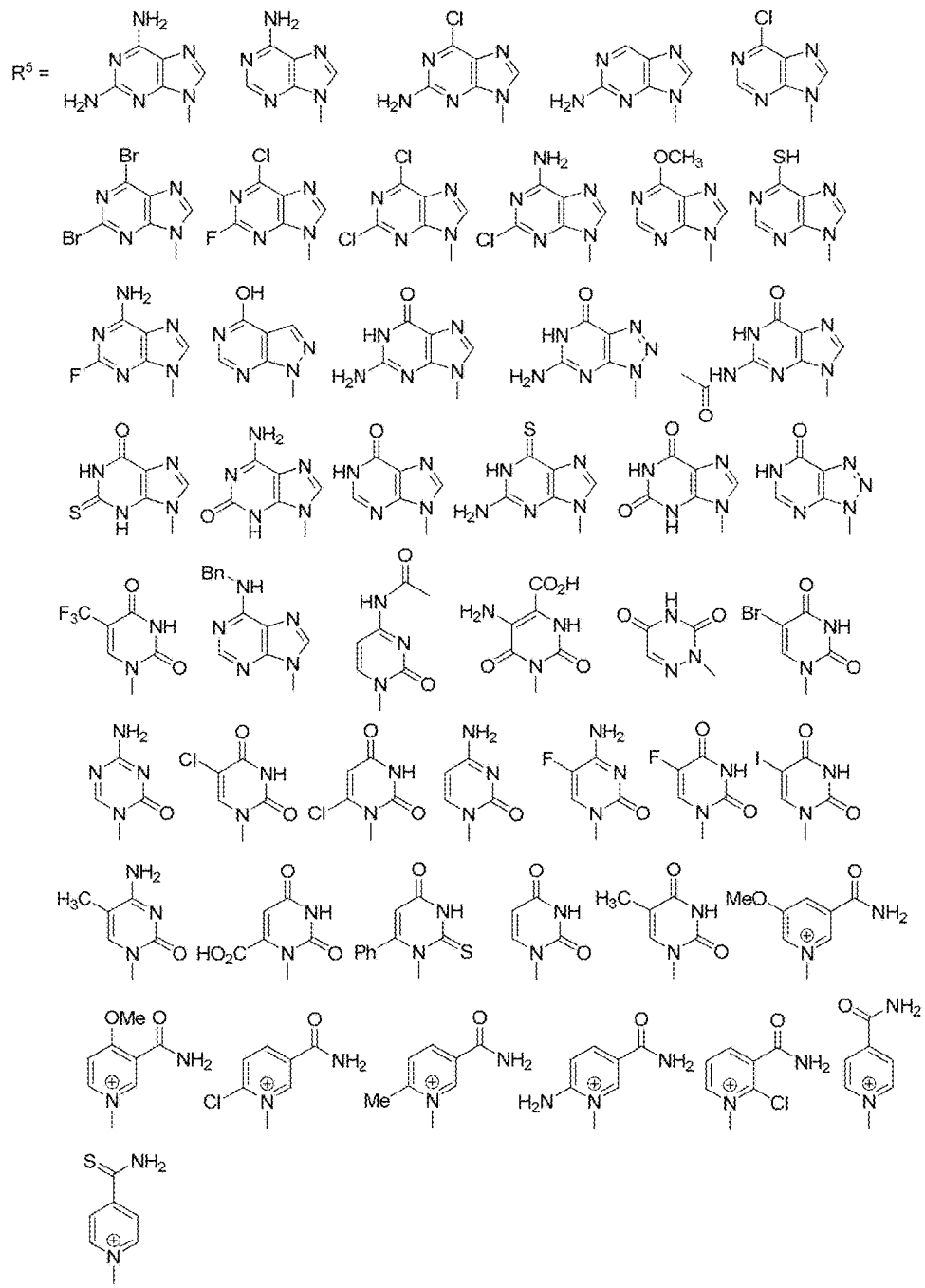

FIG. 45 illustrates specific 3',-5'-bis(TIPS)-2'-deoxy-2',2'-difluoronucleosides.

Figure 46:
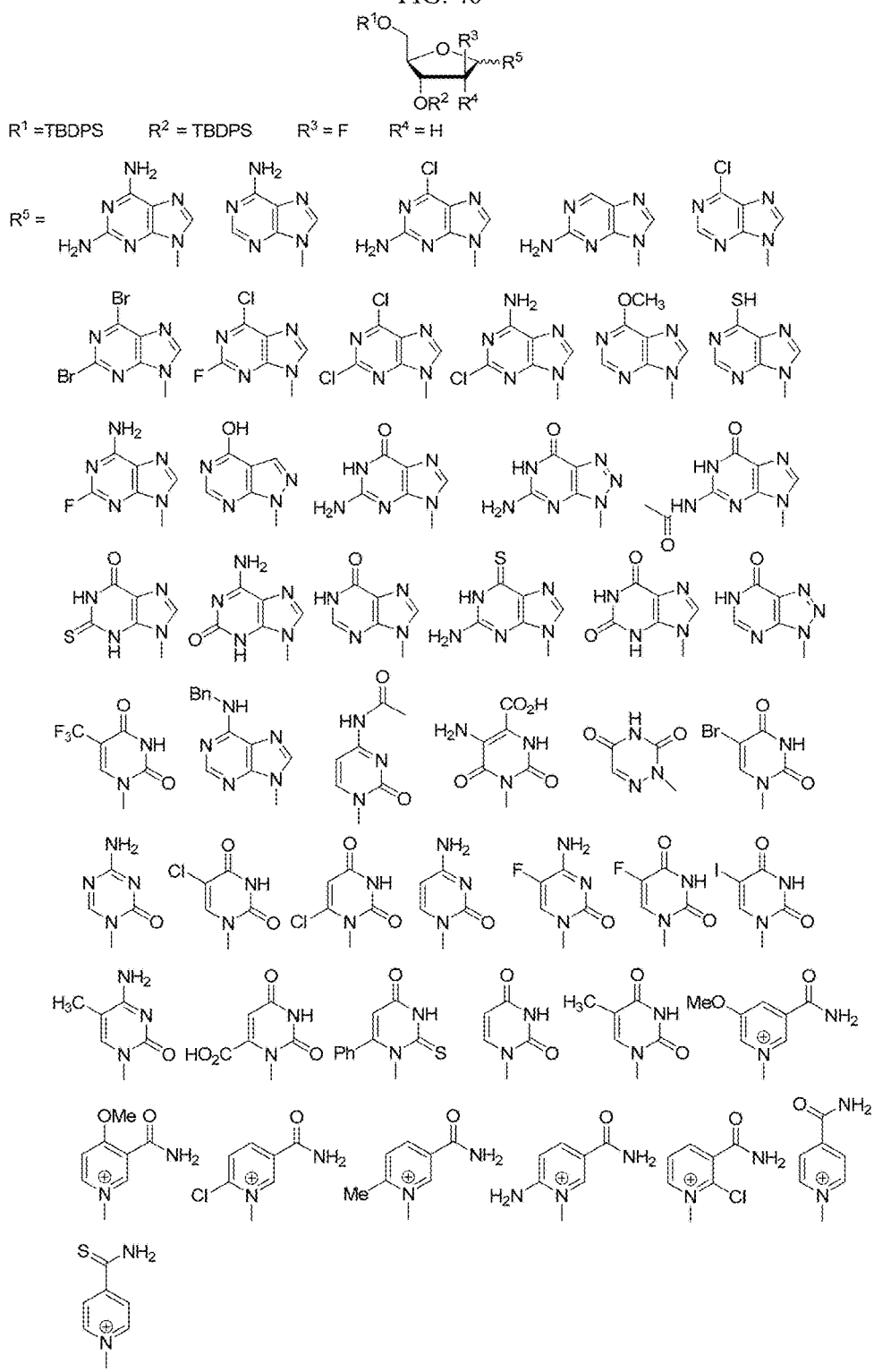

FIG. 46 illustrates specific 3',-5'-bis(TBDPS)-2'-deoxy-2'-fluoro-arabino-nucleosides.

Figure 47:
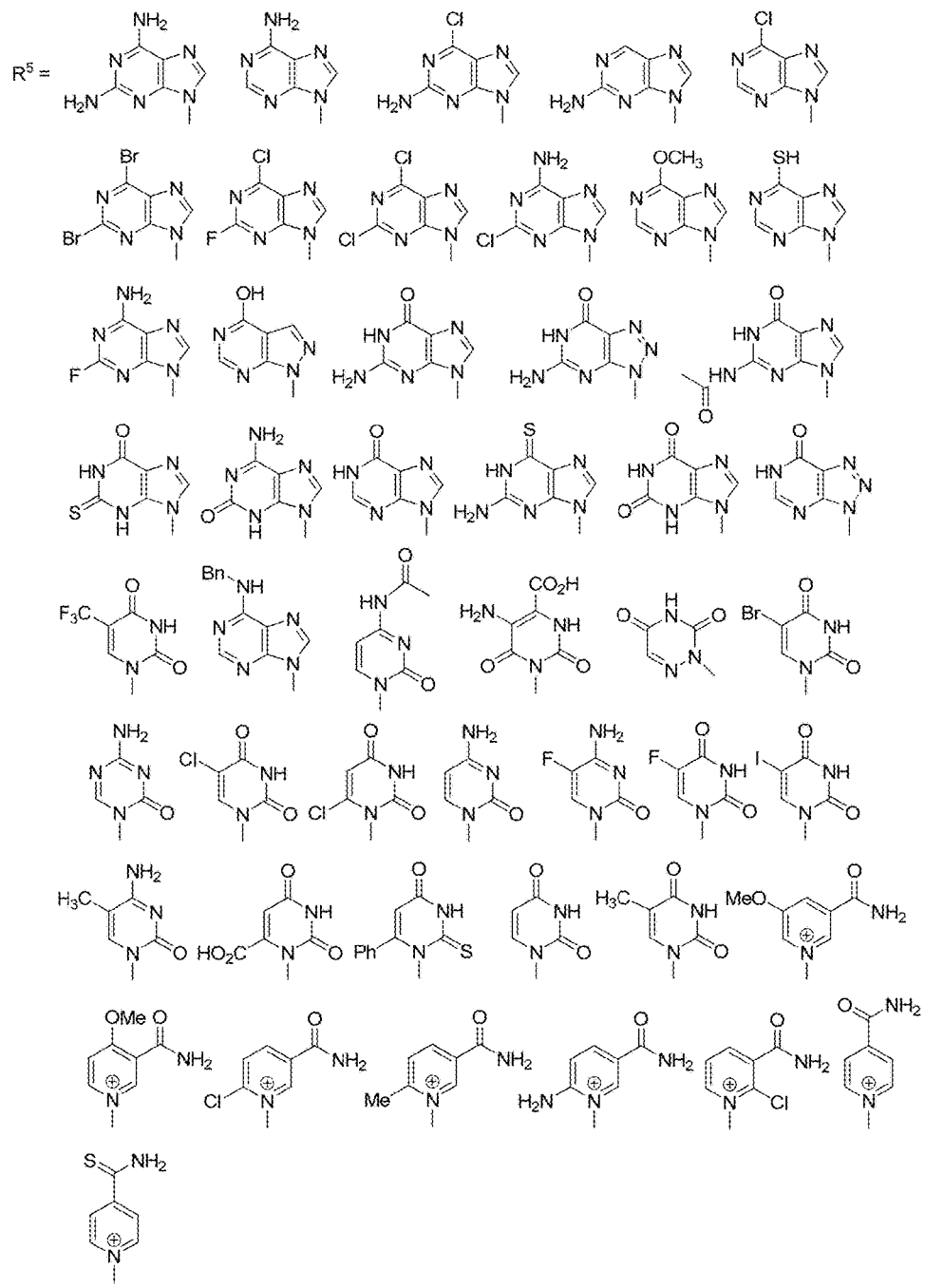

FIG. 47 illustrates specific 3',-5'-bis(TBDPS)-2'-deoxy-2'-fluoro-ribo-nucleosides.

Figure 48:
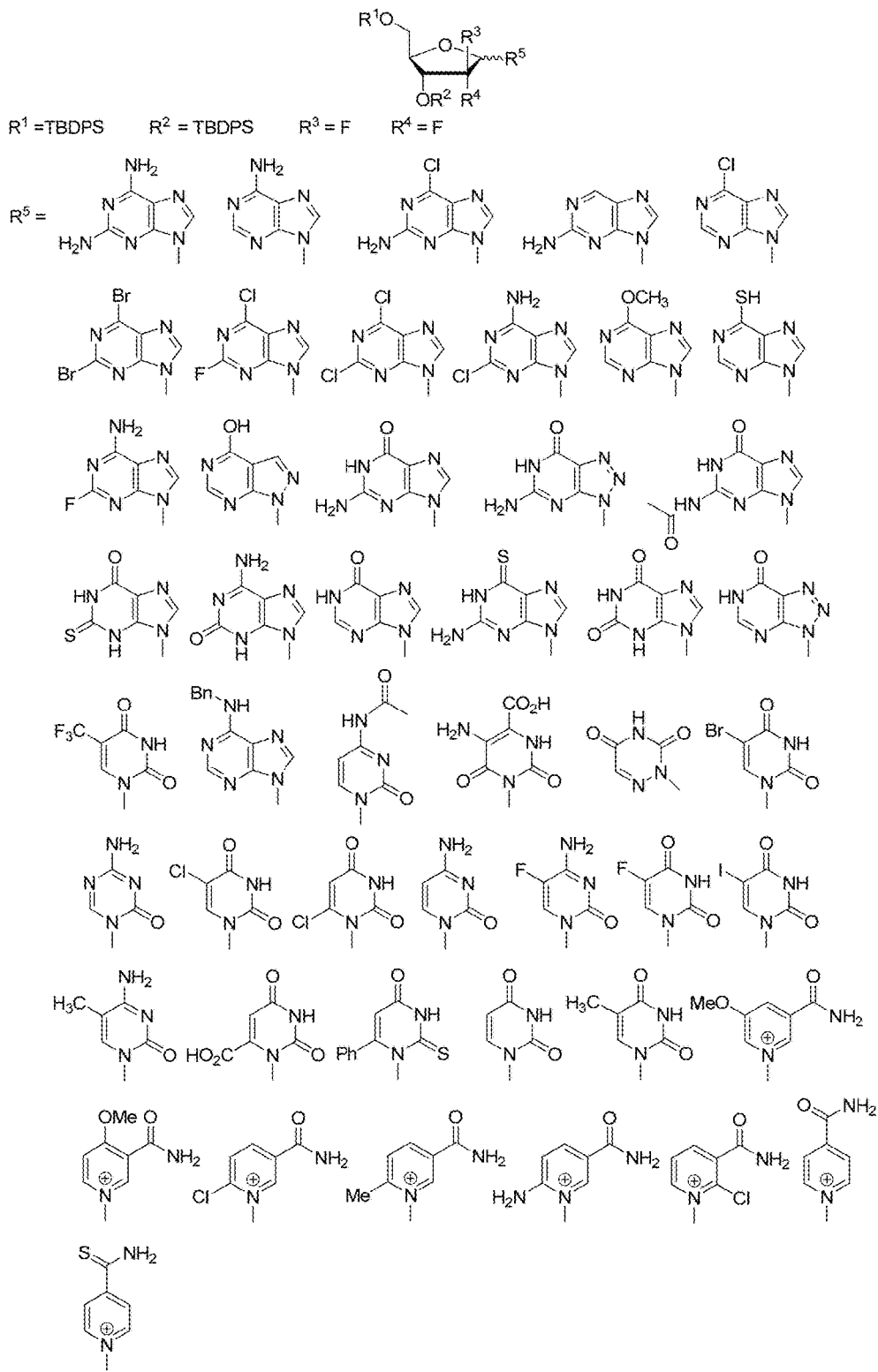

FIG. 48 illustrates specific 3',-5'-bis(TBDPS)-2'-deoxy-2',2'-difluoronucleosides.

Figure 49:
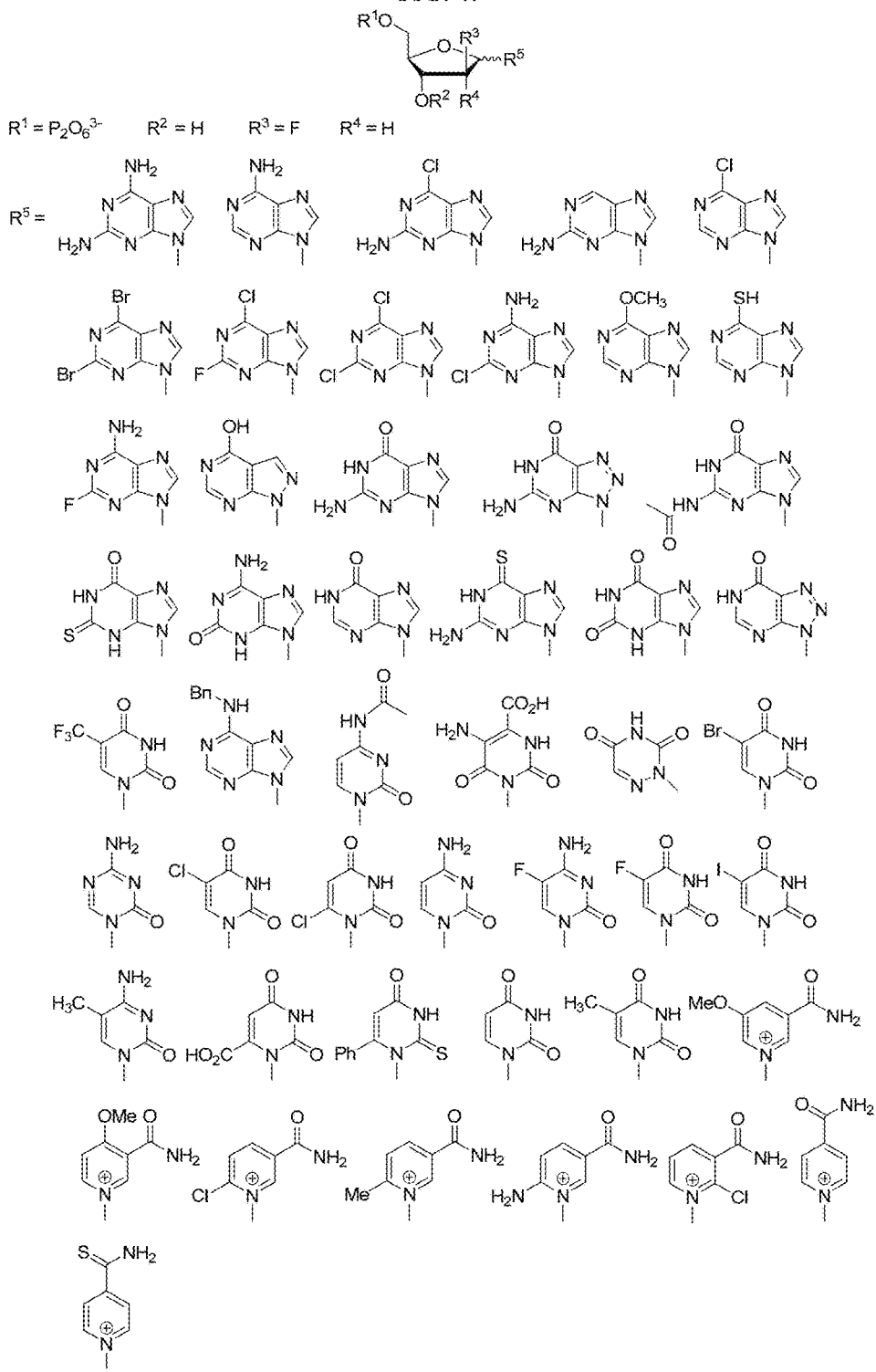

FIG. 49 illustrates specific 2'-deoxy-2'-fluoro-ribo-nucleoside-5'-diphosphates.

Figure 50:
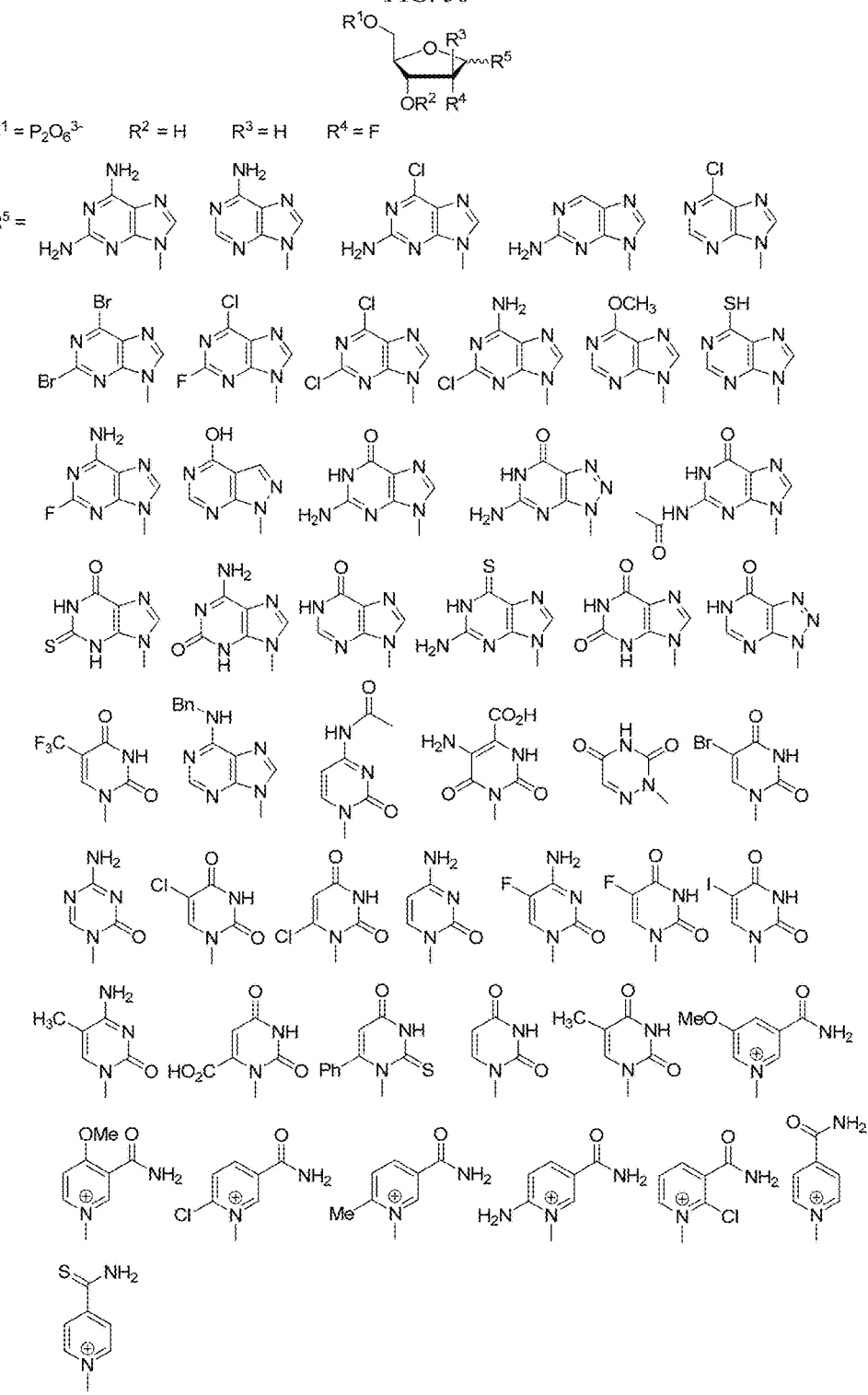

FIG. 50 illustrates specific 2'-deoxy-2',2'-difluoronucleoside-5'-diphosphates.

Figure 51:
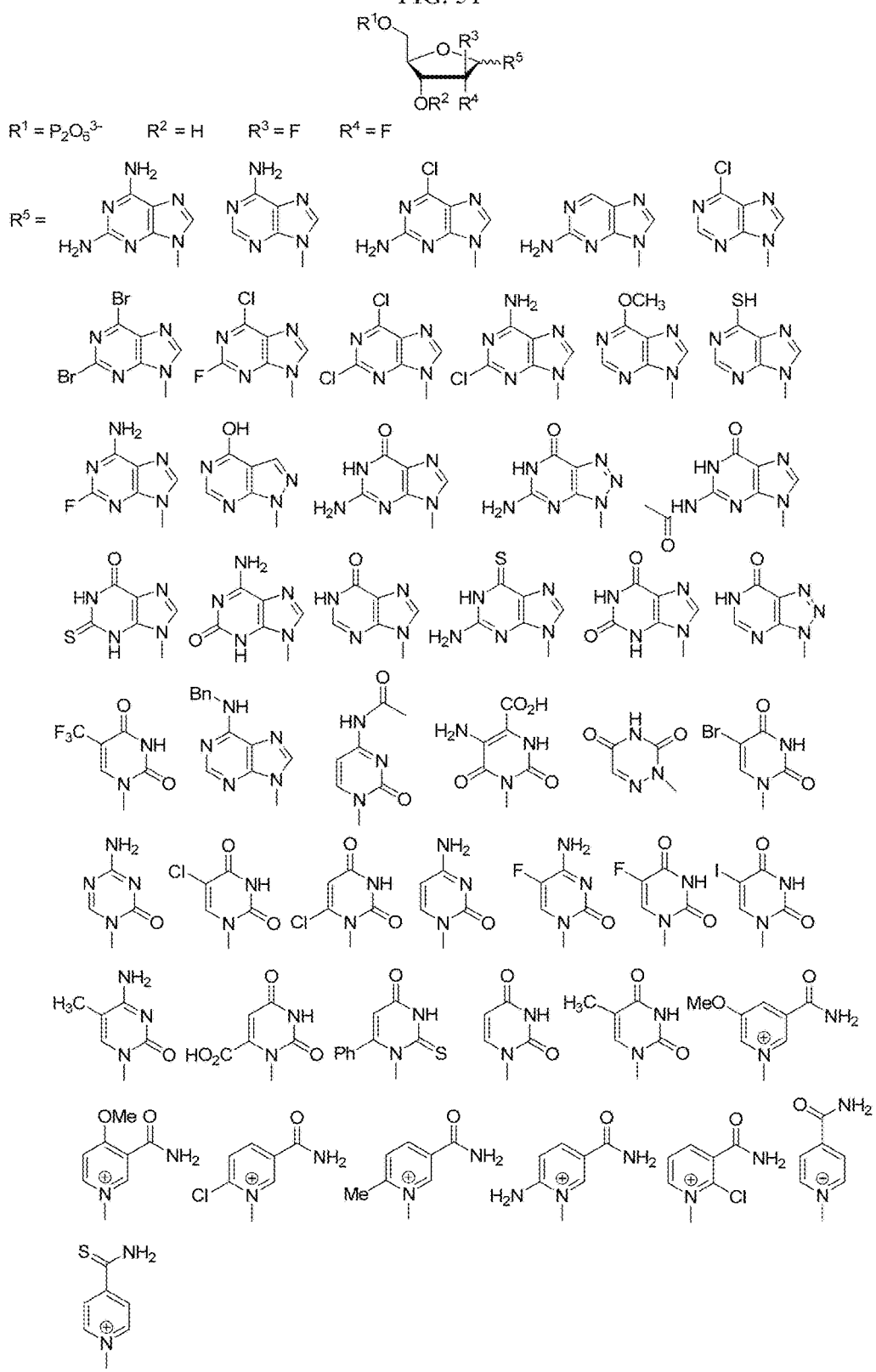

FIG. 51 illustrates specific 2'-deoxy-2'-fluoro-arabino-nucleoside-3'-diphosphates.

Figure 52:
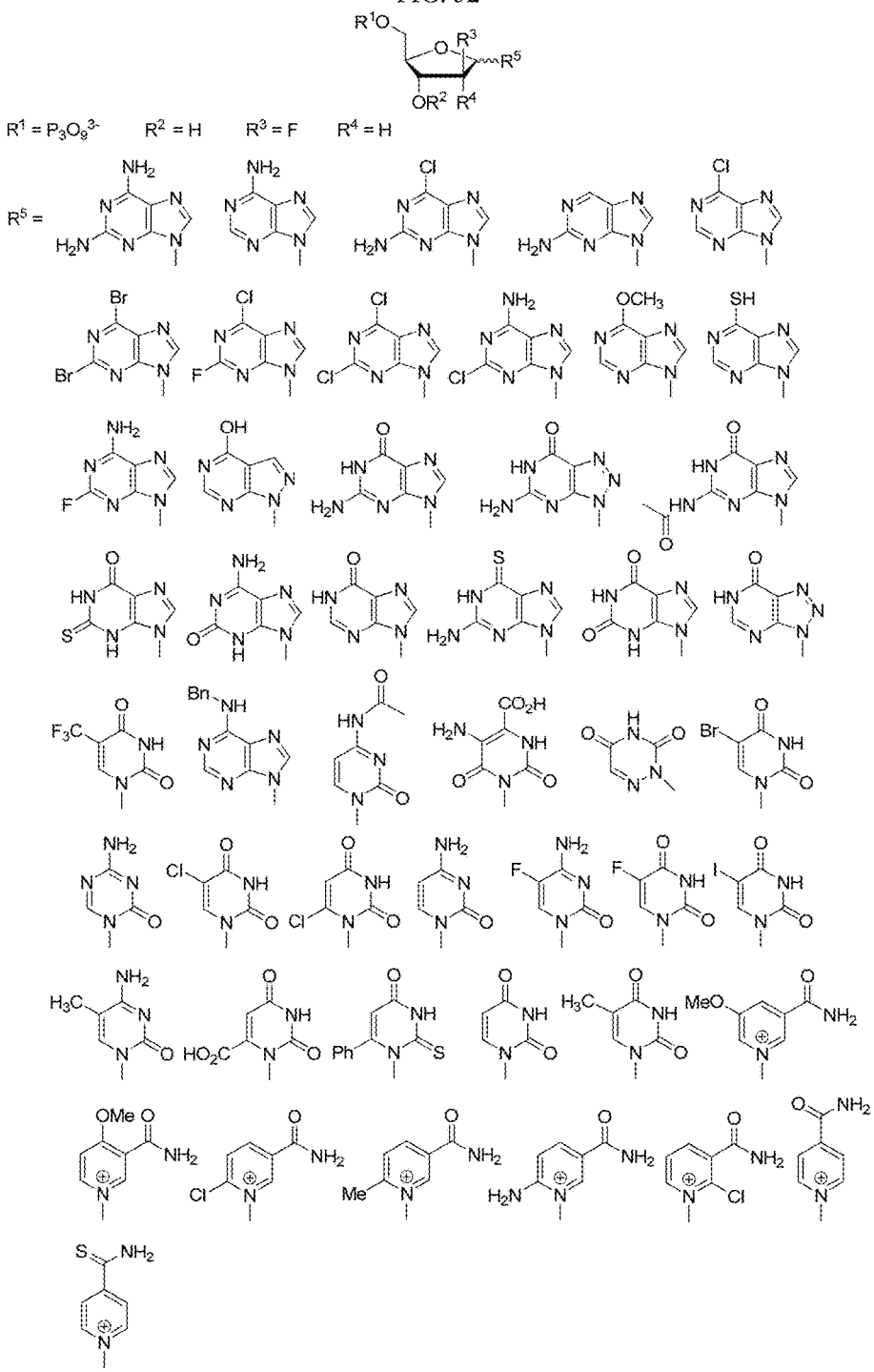

FIG. 52 illustrates specific 2'-deoxy-2'-fluoro-ribo-nucleoside-5'-triphosphates.

Figure 53:
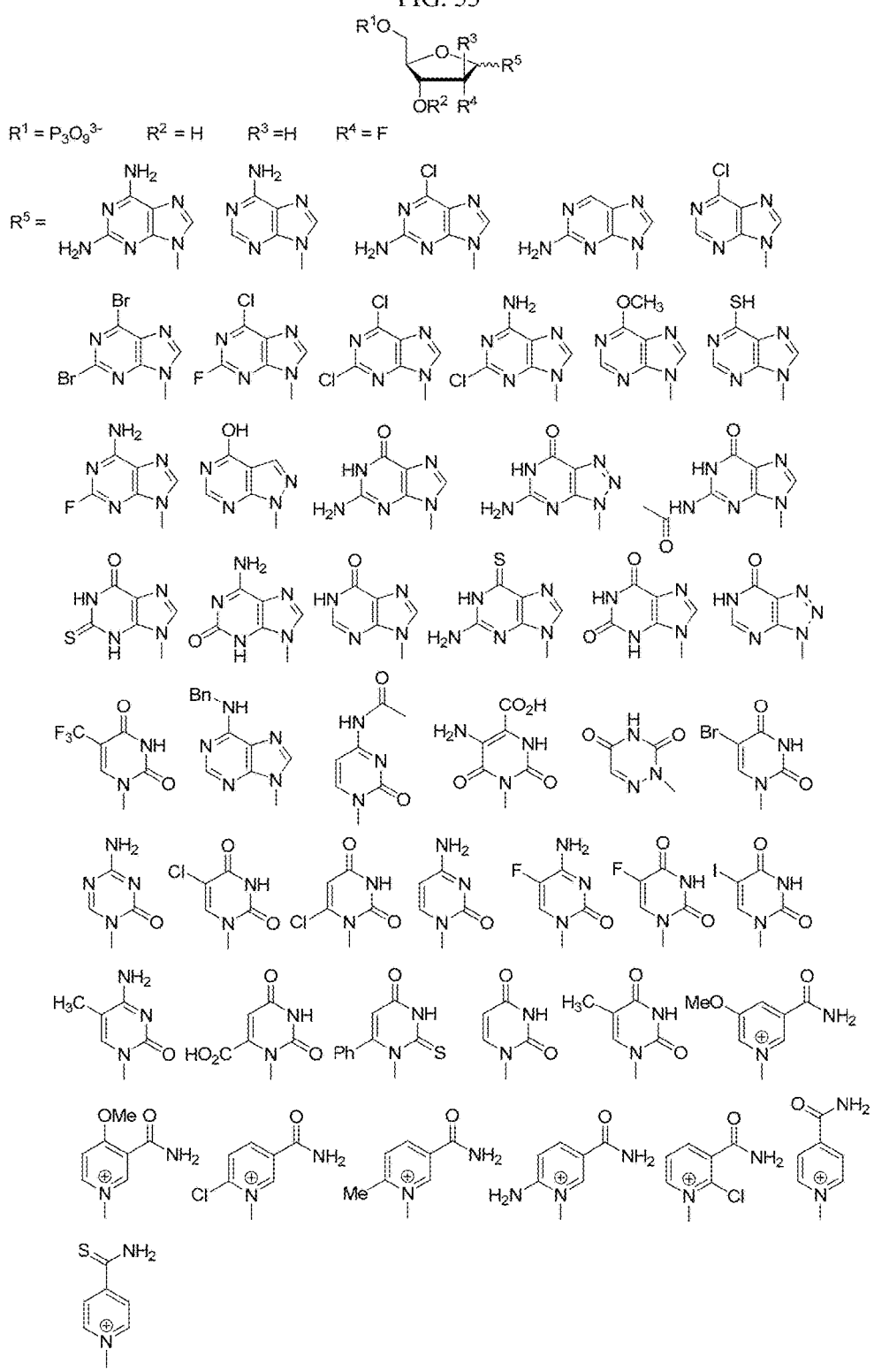

FIG. 53 illustrates specific 2'-deoxy-2',2'-difluoronucleoside-5'-triphosphates.

Figure 54:
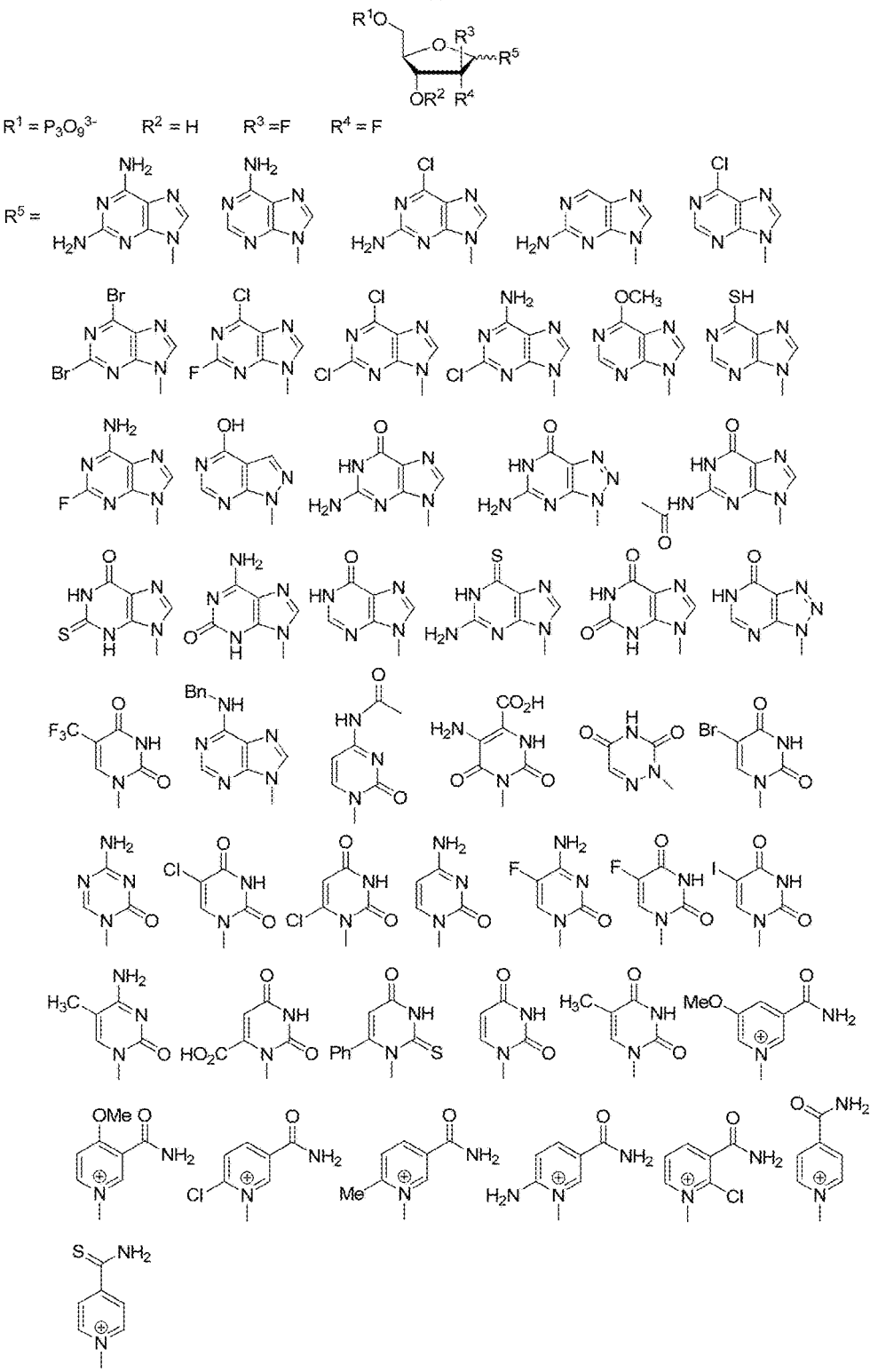

FIG. 54 illustrates specific 2'-deoxy-2'-fluoro-arabino-nucleoside-3'-triphosphates.

FIG. 55 illustrates specific 2'-fluoro-arabino-NAD$^+$ analogs.

FIG. 56 illustrates specific 2'-fluoro-ribo-NAD$^+$ analogs.

Figure 57:
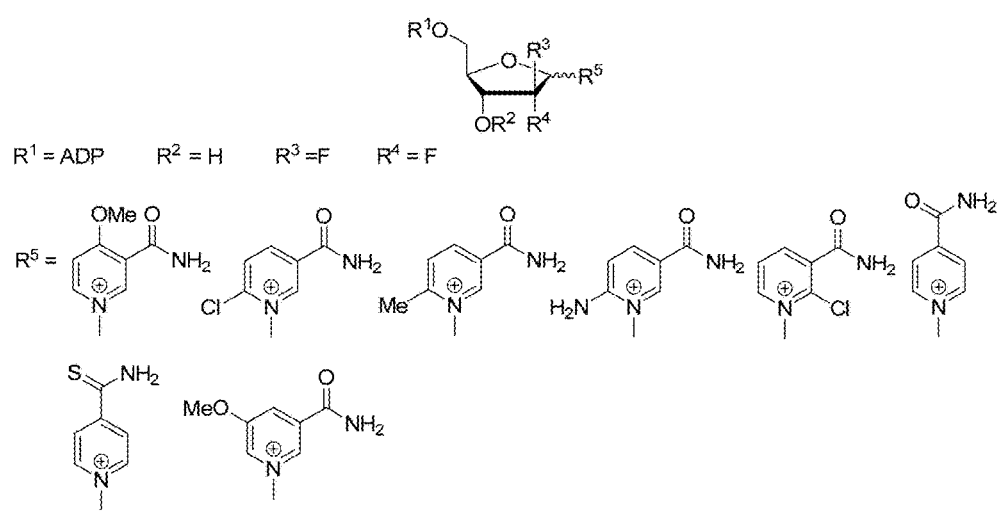

FIG. 57 illustrates specific 2'-deoxy-2',2'-difluoro-NAD+ analogs.

Figure 58:
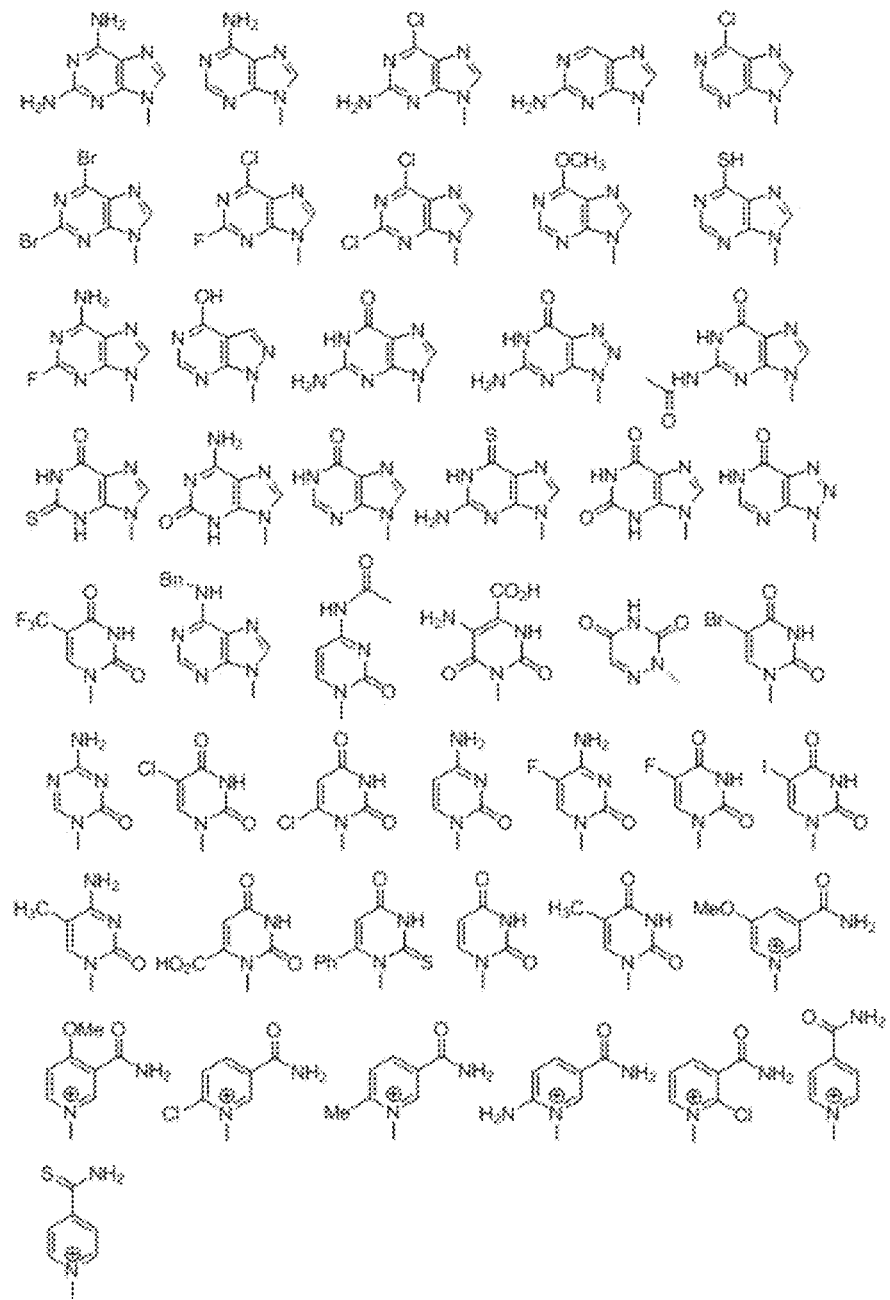

FIG. 58 illustrates specific nucleobases.

DETAILED DESCRIPTION OF THE INVENTION

The invention provides a compound of formula (I):

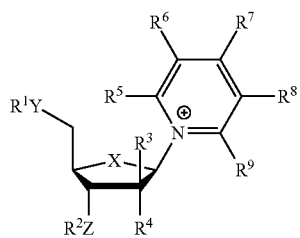

(I)

wherein $R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

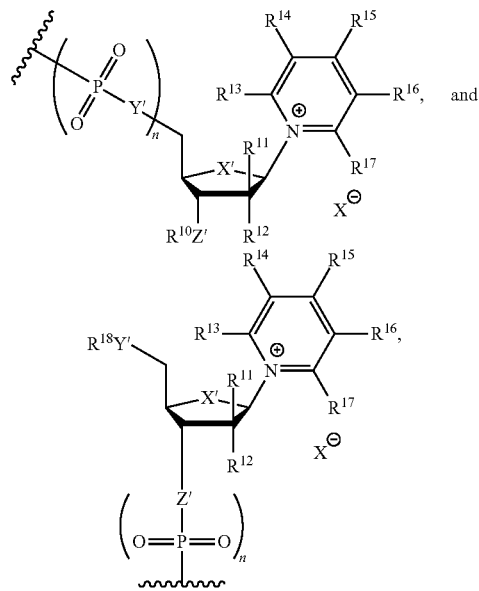

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

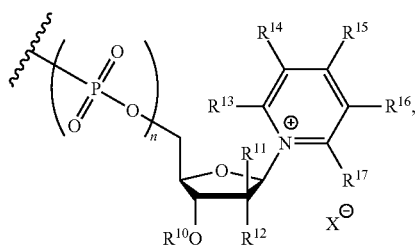

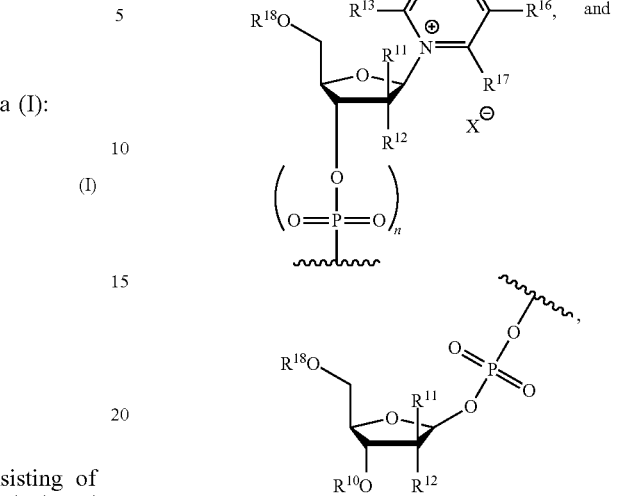

X, X', Y, Y', Z, and Z' are independently selected from the group consisting of O, S, Se, NH, and $CHR^{23}$, $R^3$ and $R^4$ are independently selected from the group consisting of hydrogen, F, Cl, Br, and I, with the proviso that $R^3$ and $R^4$ are not both hydrogen, n is 1 or 2, $R^8$ and $R^{16}$ are independently selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, each of $R^5$, $R^6$, $R^7$, $R^9$, $R^{13}$, $R^{14}$, $R^{15}$, and $R^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, F, Cl, Br, and I, $R^{23}$ is selected from the group consisting of hydrogen, alkyl, alkoxy, alkenyl, alkenyloxy, alkynyl, alkynyloxy, aryl, heteroaryl, cycloalkyl, and heterocycloalkyl, and $X^-$ is an anion, with the provisos that when $R^1$ is hydrogen, phosphate, or diphosphate, $R^2$, $R^5$, $R^6$, $R^7$, and $R^9$ are hydrogen and $R^8$ is $CONH_2$, $R^3$ is not fluoro and $R^4$ is not hydrogen, and when $R^1$, $R^2$, $R^5$, $R^6$, $R^7$, and $R^9$ are hydrogen and $R^8$ is $CONH_2$, $R^3$ is not hydrogen and $R^4$ is not fluoro, or a pharmaceutically acceptable salt thereof.

In certain embodiments, X, X', Y, Y', Z, and Z' are each O.

In accordance with more preferred embodiments, $R^8$ is $CONH_2$. In accordance with some of the above embodiments, $R^5$, $R^6$, $R^7$, and $R^9$ are hydrogen.

In certain embodiments, $R^3$ and $R^4$ are both F or Cl.

In certain embodiments, $R^3$ is hydrogen and $R^4$ is F or Cl.

In accordance with certain embodiments, $R^1$ and $R^2$ are independently selected from the group consisting of hydrogen, phosphate, diphosphate, and triphosphate.

In certain embodiments, $R^1$ and $R^2$ are independently selected from the group consisting of hydrogen, phosphate, diphosphate, and triphosphate, $R^3$ is Cl, and $R^4$ is hydrogen.

In certain embodiments, $R^1$ is hydrogen and $R^2$ is selected from the group consisting of

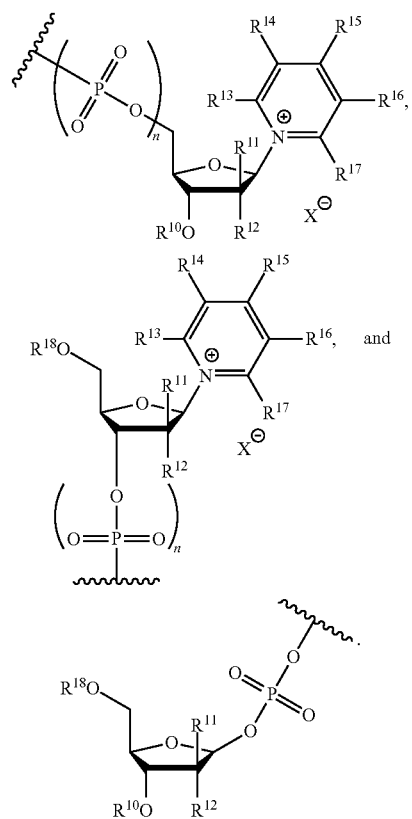

In certain embodiments, $R^2$ is hydrogen and $R^1$ is selected from the group consisting of

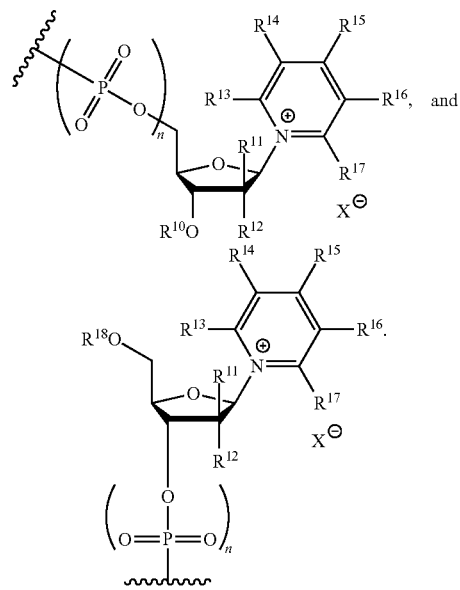

In the synthesis of the compounds, bulky protecting groups are employed. Referring to terminology used generically herein, a "bulky protecting group" is a term well known in the art. In bulky protecting groups used in the subject invention, preferably, the distance between a center atom and the outermost atom of a bulky protecting group is no less than 2.2 angstrom and the pKa of its conjugate acid is not lower than 10. Preferably, the bulky protecting group is utilized under mild temperature and pressure, does not interfere with other functional groups in the same molecule, has minimal toxicity, and is easy to install to obtain chemoselectivity in the subsequent reactions and easy to remove to complete the synthesis. Preferably, the bulky protecting group provides moderate to excellent yield (>=80%). Examples of bulky protecting groups include without limitation t-butyl; triphenylmethyl; benzyl; benzyl bromide; 2,6-bis(trifluoromethyl)benzyl (BTB) ether; t-butyldimethylsilyl (TBDMS); triisopropylsilyl (TIPS); t-butyldiphenylsilyl (TBDPS); trimethylsilyl (TMS); hexamethyldisilazane; and [2-(trimethylsilyl)ethoxy]methyl (SEM) and others described in the literature, for example in U.S. Pat. No. 4,469,881. Preferably, the bulky protecting group is a silyl, for example and without limitation, TBDMS, TIPS, TBDPS), TMS, and SEM. More preferably, the bulky protecting group is selected from the group consisting of TBDMS, TIPS, and TBDPS.

A "linker group" forms the backbone of nucleic acid polymers, and includes but is not limited to phosphodiester backbones found in endogenous and synthetic nucleic acids; phosphorothioates; phosphorodiamidates; phosphotriesters; methylphosphonates; carbamates; phosphoroamidates; sulfamides; O-methyl; and amino acids.

A nucleobase is cytosine, guanine, adenine, thymine, or uracil.

An analog of a functional group is a group in which one or more atoms, functional groups, or substructures have been replaced with different atoms, groups, or substructures, for example and without limitation, some analogs of nucleobases are hypoxanthine, xanthine, 7-methylguanine, 5,6-dihydrouracil, 5-methylcytosine, inosine, and queuosine.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1-4 carbon atoms. Lower alkyl represents; for example, methyl, ethyl, propyl, butyl, isopropyl, isobutyl, or tertiary butyl.

A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy. Di-lower alkoxy includes bridged substituents such as ethylene-dioxy or dioxolo.

A lower alkene, alkenyl or alkenyloxy group is branched or unbranched and contains 2 to 7 carbon atoms, preferably 1-4 carbon atoms and contains at least one carbon-carbon double bond. Lower alkene lower alkenyl or lower alkenyloxy represents for example vinyl, prop-1-enyl, allyl, butenyl, isopropenyl or isobutenyl and the oxy equivalents thereof.

A lower alkyne, alkynyl or alkynyloxy group is branched or unbranched and contains 2 to 7 carbon atoms, preferably 1-4 carbon atoms and contains at least one carbon-carbon triple bond. Lower alkyne or alkynyl represents for example ethynyl, prop-1-ynyl (propargyl), butynyl, isopropynyl or isobutynyl and the oxy equivalents thereof.

In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-C2-C3-alkylene; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Examples of carbocyclic aryl include naphthyl, phenyl or phenyl mono- or disubstituted by lower alkoxy, phenyl, halogen, lower alkyl or trifluoromethyl, and phenyl or phenyl mono or disubstituted by lower alkoxy, halogen or trifluoromethyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiophenyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono or di-substituted as defined above.

Cycloalkyl represents a saturated cyclic hydrocarbon optionally substituted by lower alkyl which contains 3 to 10 ring carbons and is advantageously cyclopentyl, cyclohexyl, cycloheptyl or cyclooctyl optionally substituted by lower alkyl.

Heterocycloalkyl represents a mono-, di- or tricyclic moiety comprising from 3 to 18 ring atoms, at least one of which (e.g. from 1 to 3 ring atoms) is a hetero atom selected from O, S or N, and the remaining ring atoms are carbon atoms, which are saturated or comprise one or more unsaturated alkenyl or alkynyl bonds. Preferred heterocycloalkyl moieties are N-heterocycloalkyl moieties containing from 5 to 7 ring atoms and optionally containing a further hetero atom, selected from O, S or N. Heterocycloalkyl may be substituted, for instance, as hereinafter defined and including O substitution on the heterocyclic ring e.g. as pyrrolidinone. Examples of heterocycloalkyl moieties are pyrrolidine, tetrahydrothiophene, tetrahydrofuran, piperidine, pyran, dioxane, morpholino, or piperazine, especially piperidine, morpholino or piperazine.

The present invention also provides a method for the prevention or treatment of disease in a subject, by administering to the subject a compound or salt of the invention, e.g., a composition comprising a therapeutically effective amount of a subject compound and a pharmaceutically acceptable excipient.

In another aspect, the present invention provides pharmaceutically acceptable compositions which comprise a therapeutically-effective amount of one or more of the subject compounds, as described above, formulated together with one or more pharmaceutically acceptable excipients. In another aspect, the present invention provides pharmaceutically acceptable compositions which comprise a therapeutically-effective amount of one or more of the subject compounds, as described above, formulated together with one or more pharmaceutically acceptable excipients and other therapeutically effective medications known in the art allowing for but not limited to combination therapies to improve overall efficacy of each individual therapeutic or to limit the concentration of either therapeutic to avoid side effects and maintain efficacy. The active ingredient and excipient(s) may be formulated into compositions and dosage forms according to methods known in the art. As described in detail below, the pharmaceutical compositions of the present invention may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

A therapeutically effective amount of the pharmaceutical composition of the present invention is sufficient to treat or prevent a relevant disease. The dosage of active ingredient(s) may vary, depending on the reason for use and the individual subject. The dosage may be adjusted based on the subject's weight, the age and health of the subject, and tolerance for the compound or composition.

The dose administered to a mammal, particularly, a human, in accordance with the present invention should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the human, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the mammal.

By way of example and not intending to limit the invention, the dose of the pharmaceutically active agent(s) described herein for methods of preventing abnormal cellular proliferation, a viral infection, or an autoimmune disorder, can be about 0.001 to about 1 mg/kg body weight of the subject being treated per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for methods of treating abnormal cellular proliferation, a viral infection, or an autoimmune disorder, can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19th Ed. Mack Publishing Company, Easton, Pa., (1995).

Excipients are added to the composition for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel™), microtine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit™), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel™), hydroxypropyl methyl cellulose (e.g. Methocel™), liquid glucose, magnesium aluminum silicate, maltodextrin, methylcellulose, polymethacrylates, povidone (e.g. Kollidon™, Plasdone™), pregelatinized starch, sodium alginate and starch.

The dissolution rate of a compacted solid pharmaceutical composition in the subjects's stomach may be increased by the addition of a disintegrant to the composition. Disintegrants include alginic acid, carboxymethylcellulose calcium, carboxymethylcellulose sodium (e.g. Ac Di Sol™, Primellose™), colloidal silicon dioxide, croscarmellose sodium, crospovidone (e.g. Kollidon™, Polyplasdone™), guar gum, magnesium aluminum silicate, methyl cellulose, microcrystalline cellulose, polacrilin potassium, powdered cellulose, pregelatinized starch, sodium alginate, sodium starch glycolate (e.g. Explotab™) and starch.

Glidants can be added to improve the flowability of a non compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present invention, these compounds and any other solid excipients are dissolved or suspended in a liquid carrier such as water, water-for-injection, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Flavoring agents and flavor enhancers may make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present invention may be a capsule containing the composition, for example, a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting, however, they are not subjected to a final tableting step.

The invention also provides a method of synthesizing a compound of the formula:

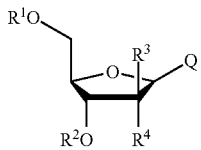

wherein Q and Q' are independently selected from the group consisting of $C_6$-$C_{10}$ aryl, $C_5$-$C_{10}$ heteroaryl, $C_5$-$C_{10}$ heterobicycloaryl, $C_5$-$C_{10}$ heterocyclyl, $C_5$-$C_{10}$ heterobicyclyl, each optionally substituted by 1, 2, 3, 4, or 5 substituents selected from the group consisting of halo, =O, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_6$-$C_{10}$ aryl, heteroaryl, $C_1$-$C_6$ haloalkyl, $C_1$-$C_6$ dihaloalkyl, $C_1$-$C_6$ trihaloalkyl, —$NO_2$, —OH, —$OR^{23}$, —SH, —$SR^{23}$, —$SOR^{23}$, —$SO_2R^{23}$, —$COR^{23}$, —COOH, —$COOR^{23}$, —$CONH_2$, —$CONHR^{23}$, —$CONHR^{23}R^{24}$, and

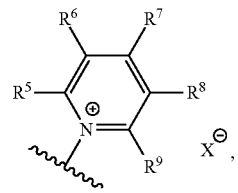

$R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

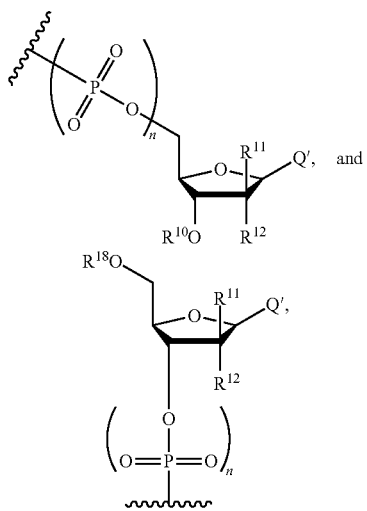

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

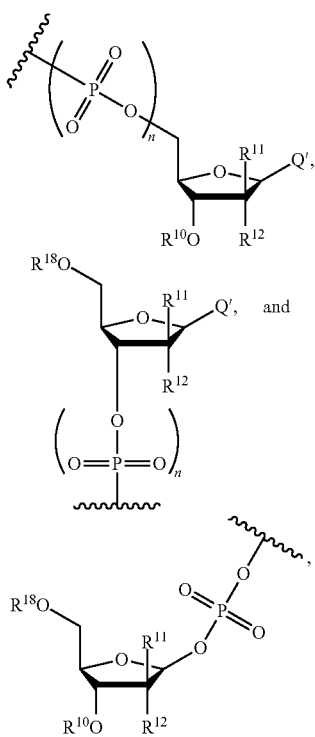

$R^3$ is F or Cl, n is 1 or 2, $R^8$ is selected from the group consisting of hydrogen, $COR^{19}$, $B(OR^{20})_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, $R^5$, $R^6$, $R^7$, $R^9$, $R^{13}$, $R^{14}$, $R^{15}$, and $R^{17}$ are independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, hydroxy, F, Cl, Br, and I, $R^{23}$ and $R^{24}$ are independently selected from the group consisting of $C_1$-$C_6$ alkyl, $C_2$-$C_6$ alkenyl, $C_2$-$C_6$ alkynyl, $C_3$-$C_8$ cycloalkyl, and $C_3$-$C_8$ cycloalkenyl, and $X^-$ is an anion, In certain embodiments, the invention provides a method of synthesizing the compound of formula (II):

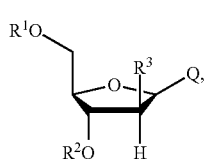

The method comprises the steps of (i) providing a compound of formula (III):

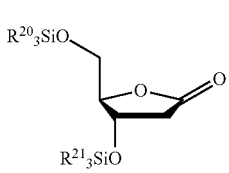

wherein each $R^{20}$ and $R^{21}$ are independently selected from the group consisting of $C_1$-$C_6$ alkyl and $C_6$-$C_{10}$ aryl, (ii) treating the compound of formula (III) with a base and a fluorinating or a chlorinating agent to provide a compound of formula (IV):

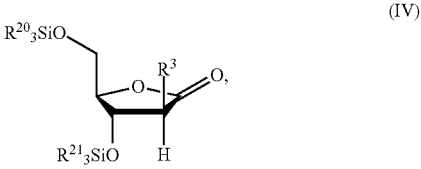

(iii) treating the compound of formula (IV) with a reducing agent to provide a compound of formula (V):

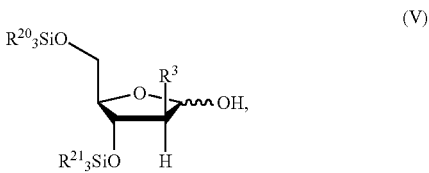

and (iv) converting the compound of formula (V) into the compound of formula (II).

In certain embodiments, the invention provides a method of synthesizing the compound of formula (VI):

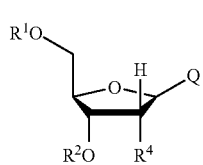

(VI)

The method comprises the steps of (i) providing a compound of formula (III):

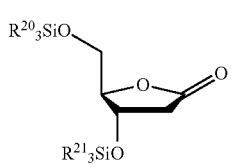

(III)

wherein each $R^{20}$ and $R^{21}$ are independently selected from the group consisting of $C_1$-$C_6$ alkyl and $C_6$-$C_{10}$ aryl, (ii) treating the compound of formula (III) with a base and a silylating agent to provide a compound of formula (VII):

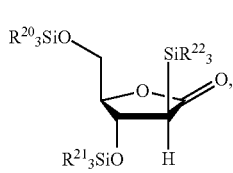

(VII)

wherein each $R^{22}$ is independently selected from the group consisting of $C_1$-$C_6$ alkyl and $C_6$-$C_{10}$ aryl, (iii) treating the compound of formula (VII) with a base and a fluorinating or a chlorinating agent to provide a compound of formula (VIII):

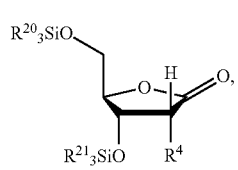

(VIII)

(iv) treating the compound of formula (VIII) with a reducing agent to provide a compound of formula (IX):

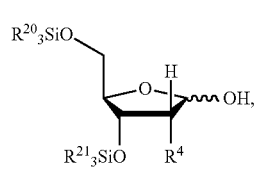

(IX)

and (v) converting the compound of formula (IX) into the compound of formula (VI).

In certain embodiments, the invention provides a method of synthesizing the compound of formula (X):

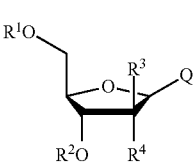

(X)

The method comprises the steps of (i) providing a compound of formula (IV):

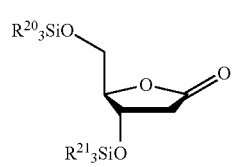

(IV)

wherein each $R^{20}$ and $R^{21}$ are independently selected from the group consisting of $C_1$-$C_6$ alkyl and $C_6$-$C_{10}$ aryl and wherein $R^3$ is F or Cl, (ii) treating the compound of formula (IV) with a base and a fluorinating or a chlorinating agent to provide a compound of formula (XI):

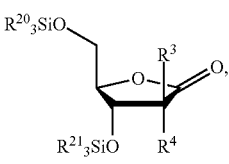

(IX)

(iii) treating the compound of formula (XI) with a reducing agent to provide a compound of formula (XII):

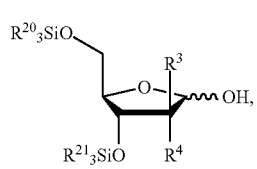

(XII)

and (iv) converting the compound of formula (XII) into the compound of formula X.

The compounds of formulas (II), (VI), and (X) encompass the inventive compounds.

Synthesis

Figure 1:
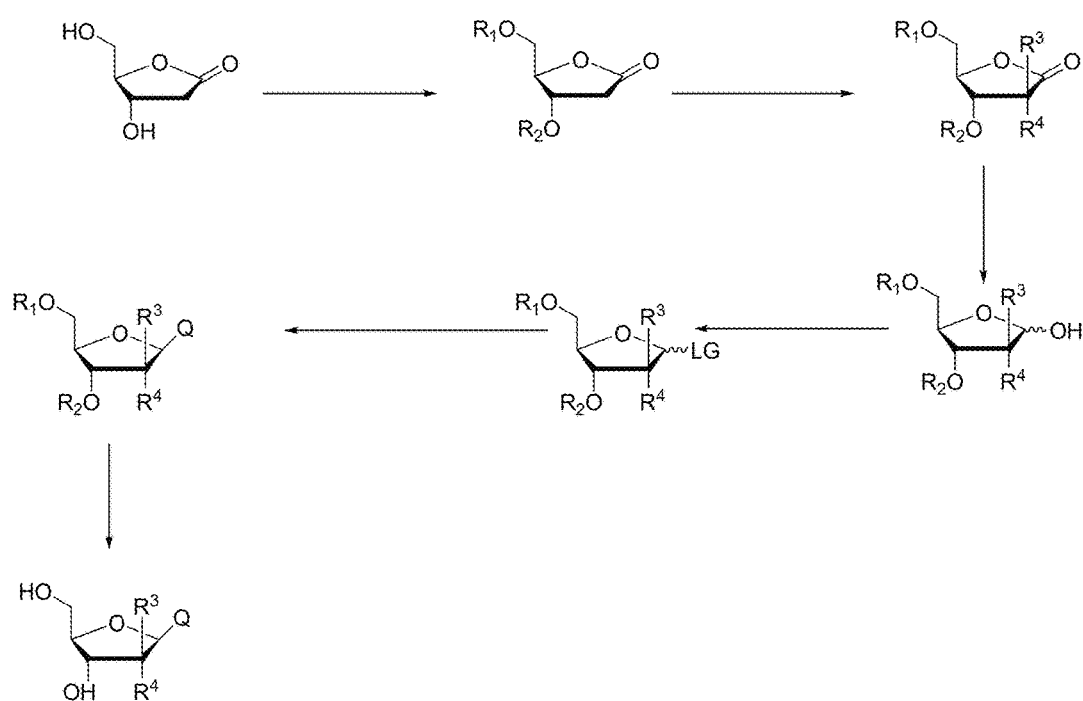
FIG. 1 illustrates a general synthetic route to prepare nucleosides or nucleotides in accordance with an embodiment of the invention.

The compounds of the invention can be synthesized according to the general scheme depicted in FIG. 1. The protected 2-deoxyribinolactone is converted to the mono- or dihalolactone. The lactone carbonyl group is reduced to the corresponding lactol. The lactol hydroxyl group is transformed into a suitable leaving group ("LG"). Displacement of the leaving group with a nucleophilic ring system followed by removal of the protecting groups provides the nucleoside. Subsequently, the free hydroxyl groups can be further reacted to provide various embodiments of the invention.

Figure 2:
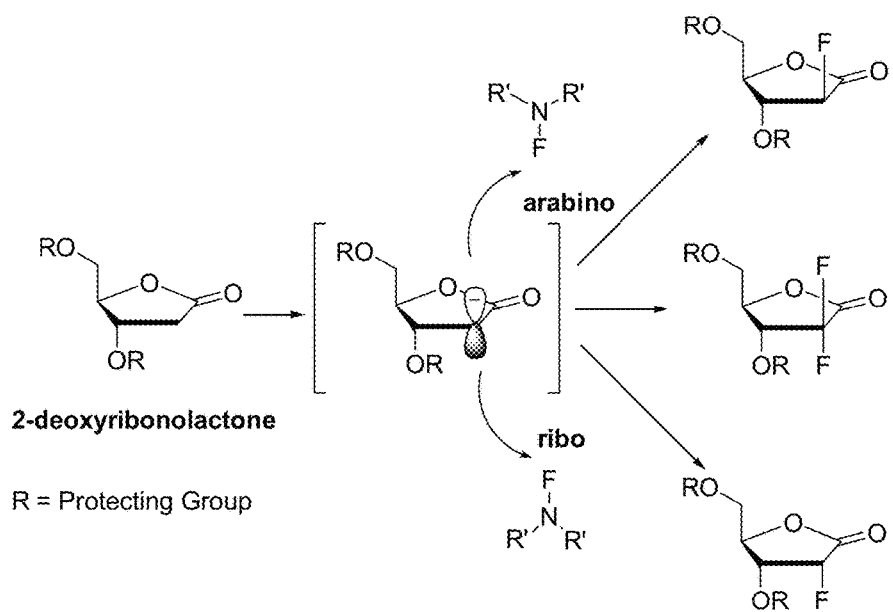
FIG. 2 illustrates synthetic routes to fluorinated ribose derivatives in accordance with an embodiment of the invention.

Generally, halogenation of the lactone is accomplished through generation of the enolate anion of a suitably protected 2-deoxy-ribonolactone, followed by reaction of the enolate anion with an appropriate electrophilic reagent, as depicted in FIG. 2. The main concerns are first, control of competing β-elimination of the enolate species leading to the unsaturated lactone and 2) to control stereochemistry for the electrophilic substitution leading to either the arabino (beta) isomer or the ribo (alpha) isomer.

Figure 3:
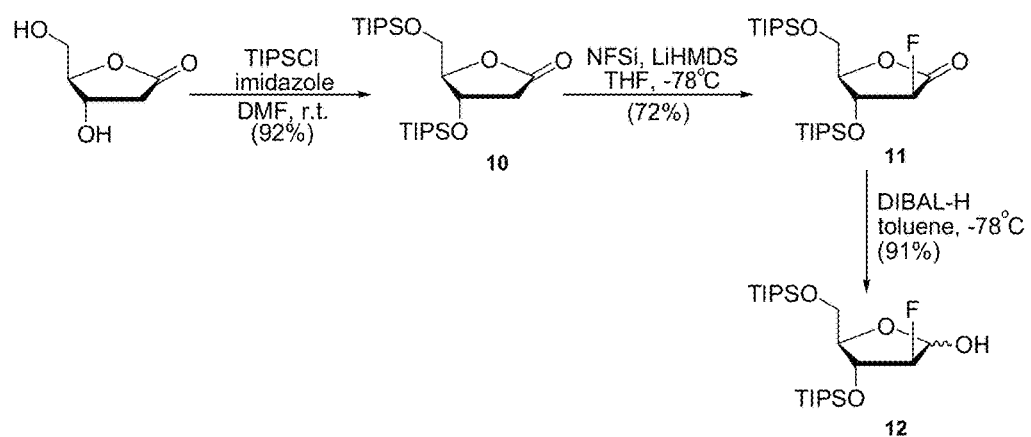
FIG. 3 illustrates a synthetic route to fluorinated arabino ribose derivatives in accordance with an embodiment of the invention.

The synthesis of a protected 2-deoxy-2-fluoro-arabinose furanose is exemplified in FIG. 3. Protection of the hydroxyl groups of 2-deoxy-ribonolactone with triisopropylchlorosilane and imidazole in DMF provides 2-deoxy-3,5-di-O-(triisopropylsilyl)-D-ribonolactone 10. Treatment of 10 with lithium bis(trimethylsilyl)amide (LiHMDS) in THF at −78° C. generates the corresponding enolate anion which reacts selectively with N-fluorodibenzenesulfonimide (NFSi) to provide 2-deoxy-2-fluoro-3,5-di-O-(triisopropylsilyl)-D-ribonolactone 11. Reduction of the lactone carbonyl group with diisobutylaluminum hydride (DIBAL-H) in toluene at −78° C. provides 2-deoxy-2-fluoro-3,5-di-O-(triisopropylsilyl)-D-arabino-furanose 12.

Figure 4:
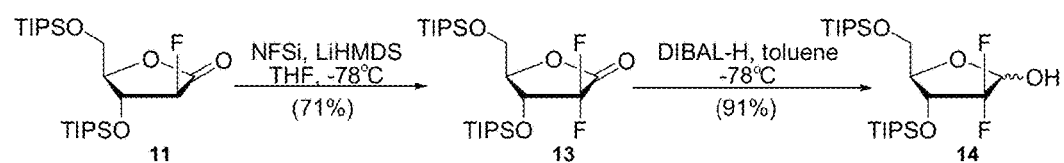
FIG. 4 illustrates a synthetic route to fluorinated ribo ribose derivatives in accordance with an embodiment of the invention.

The synthesis of a protected 2-deoxy-2,2-difluoro-ribofuranose is exemplified in FIG. 4. Treatment of 2-deoxy-2-fluoro-3,5-di-O-(triisopropylsilyl)-D-ribonolactone 11 with LiHMDS in THF at −78° C. generates the corresponding enolate anion which reacts selectively with N-fluorodibenzenesulfonimide (NFSi) to provide 2-deoxy-2,2-difluoro-3,5-di-O-(triisopropylsilyl)-D-ribonolactone 13. Reduction of the lactone carbonyl group with DIBAL-H in toluene at −78° C. to provide 2-deoxy-2,2-difluoro-3,5-di-O-(triisopropylsilyl)-D-ribofuranose 14.

Figure 5:
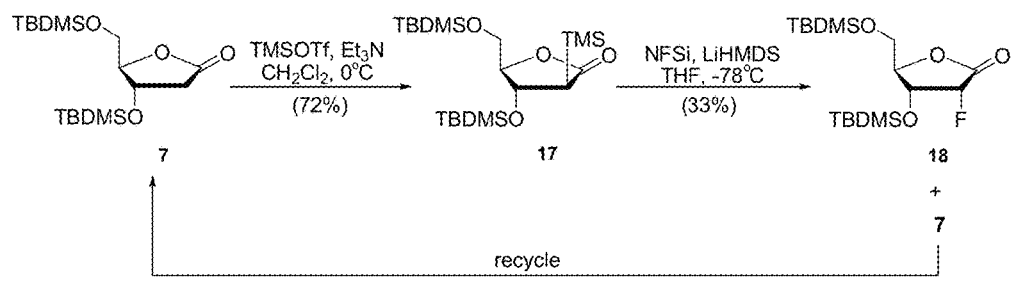
FIG. 5 illustrates a synthetic route to a protected 2-deoxy-2-fluoro-ribo-lactone in accordance with an embodiment of the invention.

Synthesis of protected 2-deoxy-2-fluoro-ribo-lactone proceeds via a 2-silyl intermediate and is exemplified in FIG. 5. 2-deoxy-3,5-di-O-(t-butyldimethylsilyl)-D-ribonolactone 7 is obtained by oxidation of 2-deoxy-D-ribose with bromine in water followed by silylation with t-butyldimethylsilyl chloride and imidazole in DMF. Treatment of 7 with TMSOTf and Et$_3$N in DCM provides 2-deoxy-2-trimethylsilyl-3,5-di-O-(t-butyldimethylsilyl)-D-arabinolactone 17. Generation of the enolate anion of 17 with LiHMDS in THF at −78° C., followed by reaction with NFSi provides after column chromatography 2-deoxy-2-fluoro-3,5-di-O-(t-butyldimethylsilyl)-D-ribonolactone 18.

Figure 6:
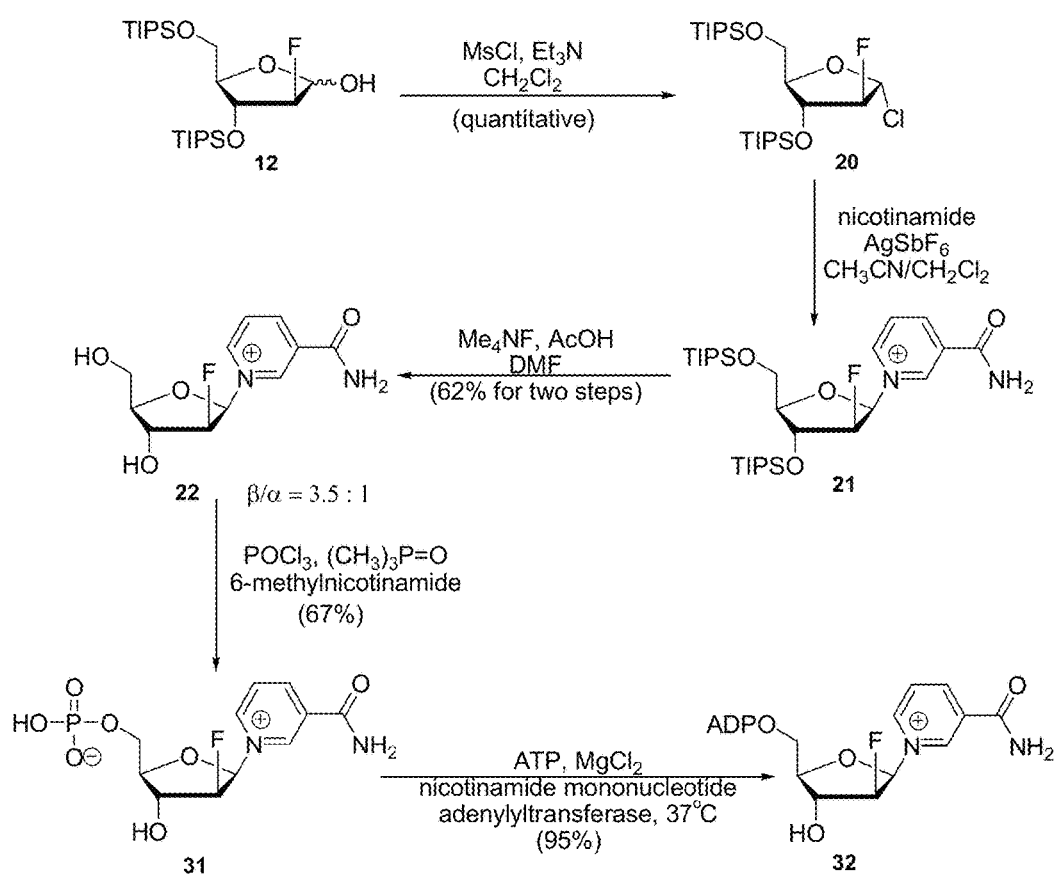
FIG. 6 illustrates a synthetic route to nucleotides in accordance with an embodiment of the invention.

The synthesis of the 1-(2'-deoxy-2'-fluoro-arabinofuranosyl)-nicotinamide 22 in 5 steps, 38% isolated yield from protected 2-deoxyribonolactone is depicted in FIG. 6. 12 was activated with methanesulfonylchloride and triethylamine, which formed only the α-chloro sugar 20. 20 was coupled with nicotinamide in acetonitrile and dichloromethane mixed solvent with stoichiometric amount of AgSbF$_6$. Crude product 21 was a mixture of both isomers with β being the major isomer. After deprotection with fluoride, β and α-isomers were separated by preparative HPLC (β:α=3.5). The $^1$H NMR spectrum obtained for 22 (β) agreed with literature data (Ref. 25). Yield of 22 (β) from 12 was 62% and required only one purification step.

Figure 7:
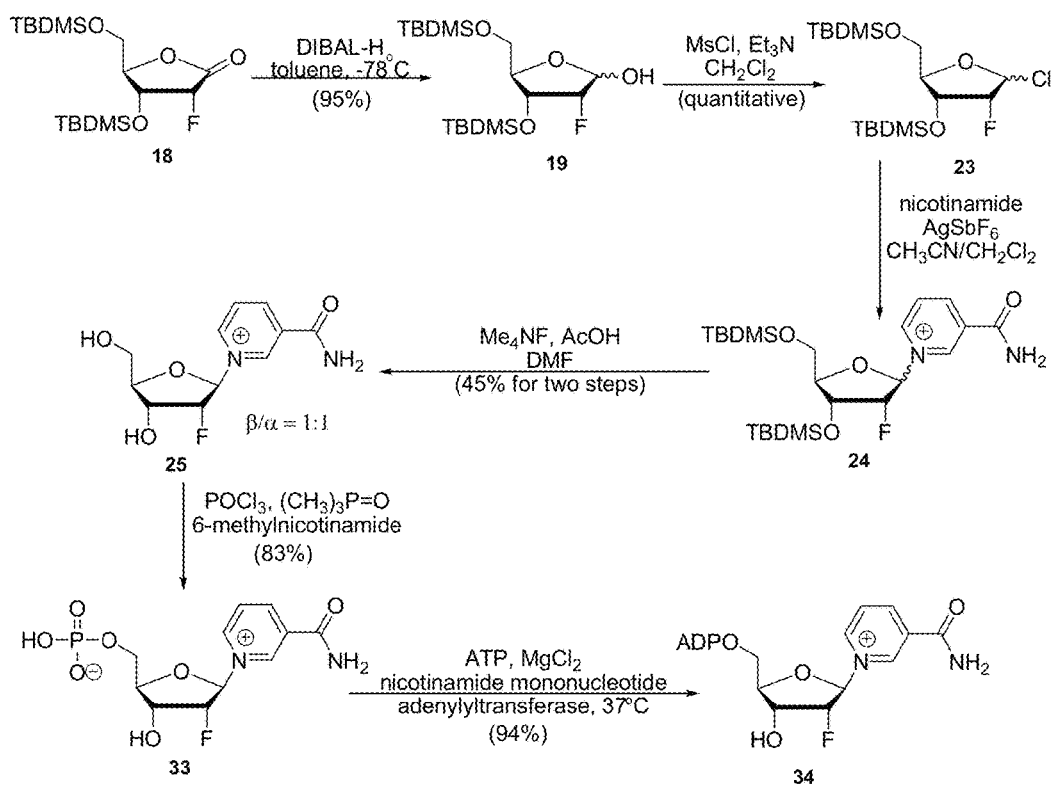
FIG. 7 illustrates a synthetic route to nucleotides in accordance with an embodiment of the invention.

The synthesis of this compound in 6 steps and 15% isolated yield from 2-deoxy-ribonolactone is depicted in FIG. 7. The furanose 19 was converted to the chloro sugar 23 by treatment with methanesulfonylchloride and triethylamine, the reaction occurred quantitatively but produced both α- and β-isomers. Coupling of the chloro-sugar to nicotinamide with AgSbF$_6$ provided a mixture of nicotinamide adducts 24, followed by deprotection and HPLC purification to provide the desired nicotinamide substituted 2'-deoxy-T-fluoro-ribo-nucleoside 25 in 45% yield from the lactol 19. The corresponding a isomer was isolated in 46% yield. Stereochemistries were assigned by NOEs (see Examples).

Figure 8:
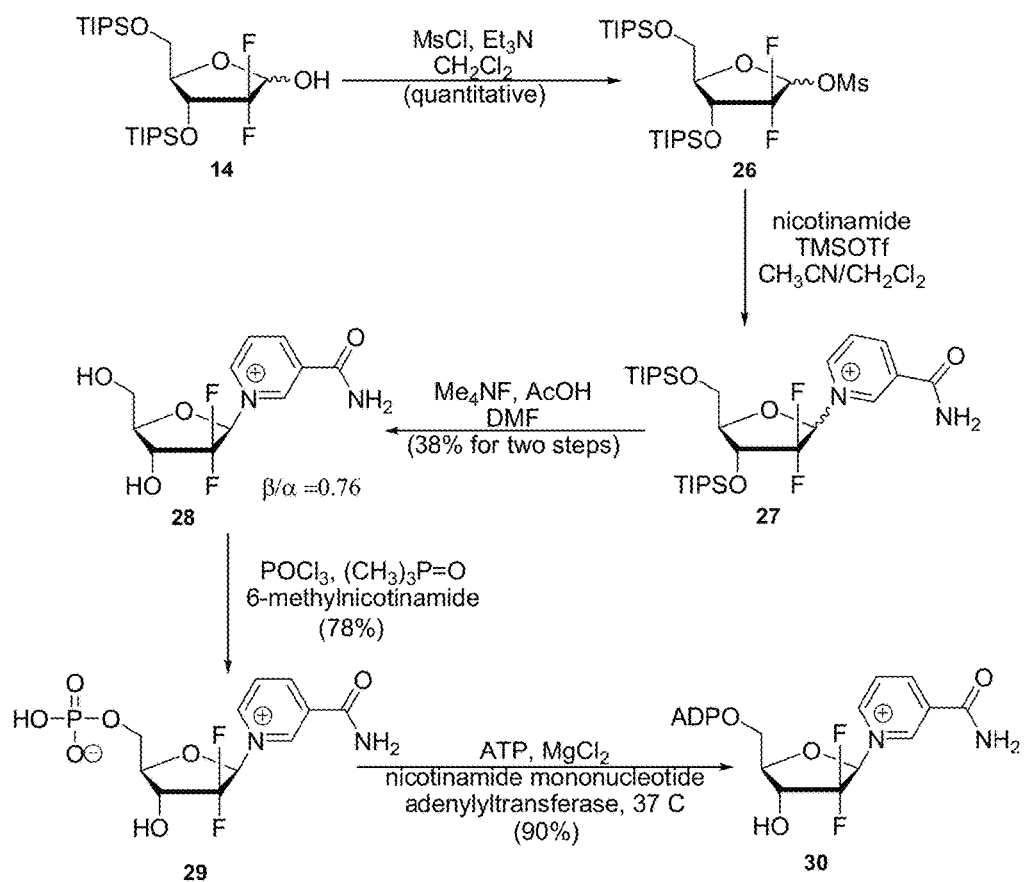
FIG. 8 illustrates a synthetic route to nucleotides in accordance with an embodiment of the invention.

The synthesis of the 1-(T-deoxy-2',2'-difluoro-ribofuranosyl)-nicotinamide has never been reported. The synthesis of the β-isomer of the 1-(2'-deoxy-2',2'-difluoro-ribofuranosyl)-nicotinamide in 6 steps with 18% isolated yield and 23% for the α-isomer is depicted in FIG. 8. The 1-mesylate 26 was prepared similarly to a reported method (Ref. 35). It appears that the additional fluorine at the 2-position deactivates the mesylate from nucleophilic chlorination which occurs for the arabino- and ribo-fluoro analogues (Schemes 10 and 11). Reaction with nicotinamide yielded nucleoside 27 in both α and β-configuration. Subsequent deprotection and HPLC purification provided β-28 in 38% yield and the α-anomer in 50% yield. Poor stereochemical control from the mesylate is known, with few preferable alternatives (Ref. 35). NOEs between the H$_{1'}$ and H$_{4'}$ in the β-nucleoside and NOEs between the H$_{1'}$ and H$_{3'}$ and nicotinamide H$_2$ and H$_{4'}$ for the α isomer confirmed stereochemistries.

The complete syntheses of the difluoro-nucleotide and difluoro-dinucleotide are described, with syntheses of the other nicotinamide substituted mononucleotides and dinucleotides being accomplished in a similar manner. The monofluoro derivatives were prepared by similar methods and the preparation of these compounds is described in the experimental and in FIG. 8. 1-(2-deoxy-2,2-difluororibosyl)-nicotinamide 28 (β-isomer) was phosphorylated with POCl$_3$ in trimethylphosphate in the presence of 6-methylnicotinamide, a hindered weak base which controls acidity, to yield 2'-deoxy-2',2'-difluoro-nicotinamide mononucleotide (2'-deoxy-2',2'-difluoro-NMN) 29 in 78% isolated yield (Scheme 12). Although previously unstudied, it was found that the 2-fluoro-NMN compounds could be adenylated enzymatically with yeast nicotinamide mononucleotide adenylyltransferase (Ref. 46) (NMNAT-1). In this case, reaction with ATP furnished 2'-deoxy-2',2'-difluoro-NAD$^+$ 30 in 90% yield versus ATP, which was limiting, with recovery of unreacted 29. These steps complete the first reported syntheses of 2',2'-difluoro-NMN and 2',2'-difluoro-NAD$^+$. The dinucleotide was completed in 8 steps with 14% overall yield from 2-deoxyribonolactone 10. Similarly with these methods 2'-fluoro-arabino-NMN and NAD$^+$ 31, 32 (7 steps 22.4% yield from 10) were synthesized as well as T-fluoro-ribo-NMN and NAD$^+$ 33, 34 (8 steps 12% yield from 7).

Figure 9:
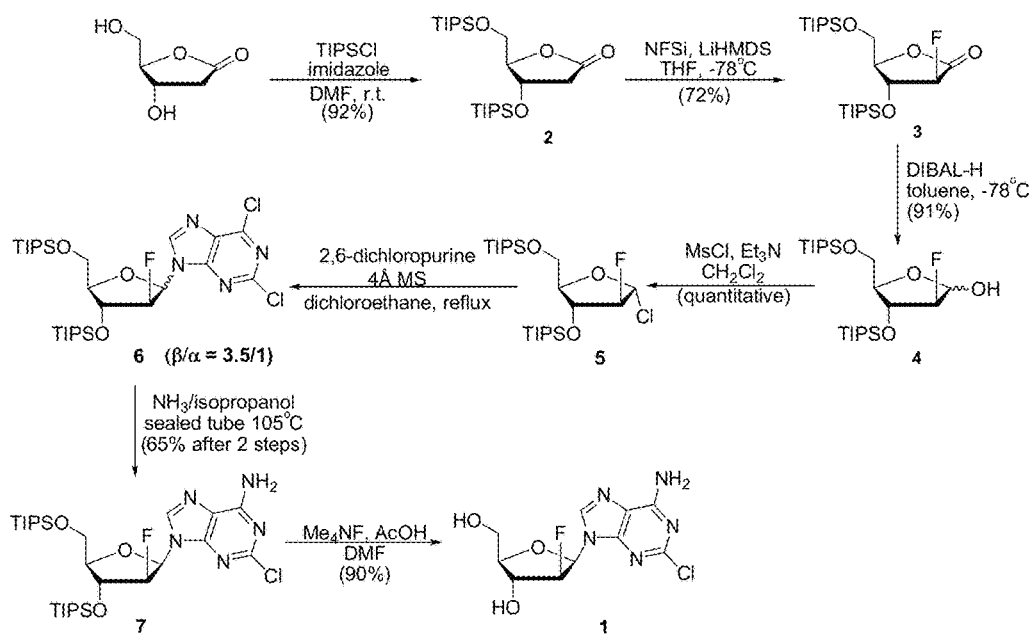
FIG. 9 illustrates a synthesis of clofarabine in accordance with an embodiment of the invention.

Clofarabine (1,2-chloro-2'-deoxy-2'-fluoro-arabino-adenosine) is a purine nucleoside antimetabolites used clinically for pediatric patients with relapsed or refractory acute lymphocytic leukemia. It interrupts DNA synthesis by inhibiting ribonucleotide reductase to terminate DNA chain elongation. The synthesis of clarafabine is depicted in FIG. 9. TIPS-protected 2-deoxy-ribonolactone 35 was obtained in 92% yield from 2-deoxy-ribonolactone. 35 was treated with LiHMDS with the presence of NFSi at −78° C. to furnish only the arabino-isomer 36 in 72% isolated yield. Reduction of 36 with DIBAL-H provided lactol 37 in 91% yield. 37 was activated with methanesulfonylchloride and triethylamine, which formed only the α-chloro sugar 38 in quantitative yield. 38 was coupled with 2,6-dichloropurine by employing a previous reported method. This coupling gave a mixture of both the β and α isomers with a 3.5 to 1 ratio favoring the β-isomer. The mixture 39 was used in the next step without further purification. Amination of 39 with ammonia in isopropanol in a sealed tube at 105° C. afforded the desired 2-amino-6-chloropurine nucleoside 40, at this stage β-anomer was purified by column chromatography and the yield after coupling and amination steps is about 65%. Finally, deprotection of the silyl protecting groups gave clofarabine 41 as an off-white solid, the NMR matches the reported data.

Figure 10:
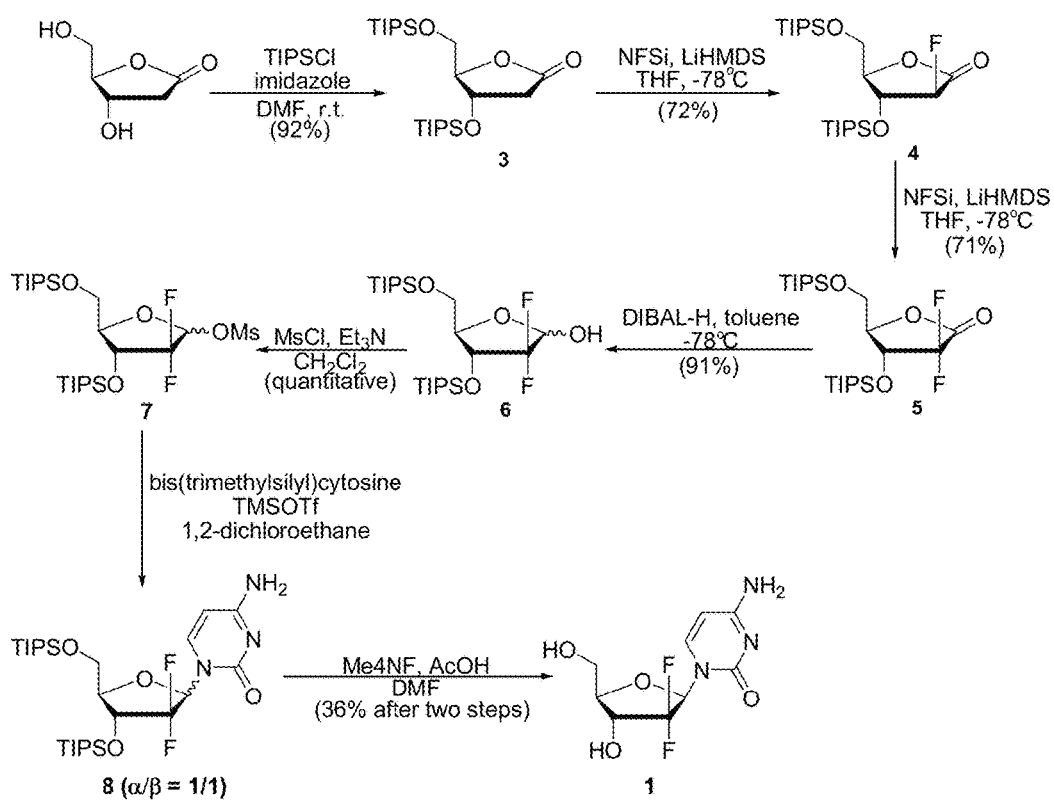
FIG. 10 illustrates a synthesis of gemcitabine in accordance with an embodiment of the invention.

The synthesis of gemcitabine is depicted in FIG. 10. This approach is highlighted by electrophilic fluorination of protected 2-deoxy-ribonolactone with an air-stable fluorinating agent, NFSi, and the total yield is drastically improved over the reported syntheses to about 33%.

TIPS-protected 2-deoxy-ribonolactone 35 was obtained in 92% yield from 2-deoxy-ribonolactone (Scheme 18). 35 was treated with LiHMDS with the presence of NFSi at −78° C. to furnish only the arabino-isomer 36 in 72% isolated yield. The second fluorination of 36 under the same reaction conditions provided the desired 2-deoxy-2,2-difluoro-ribonolactone 42 in 71% yield. Reduction with DIBAL-H provided lactol 43 in 91% yield.

The 1-mesylate 44 was prepared similarly to the reported method. Reaction with bis(trimethylsilyl)cytosine yielded nucleoside 45 in both α and β-configuration. Integration from NMR spectrum indicates the α/β ratio is 1:1. Subsequent deprotection and HPLC purification provided β-46 in 36% yield for two steps. Proton NMR matches reported data. The synthesis of the nucleoside was completed in 7 steps with 17% overall yield.

Figure 11:
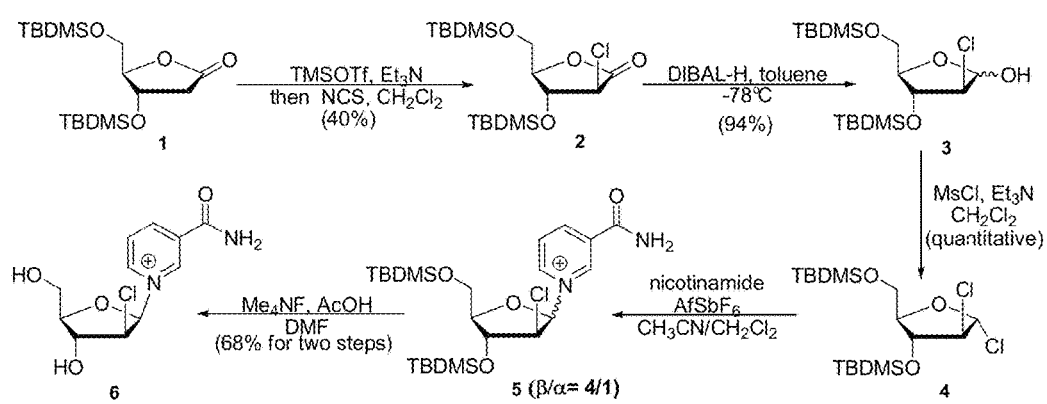
FIG. 11 illustrates a synthetic route to chlorinated nucleotides in accordance with an embodiment of the invention.

In certain embodiments, the invention provides methods for synthesis of chloro nucleosides. Referring to FIG. 11, treatment of 47 with TMSOTf, triethylamine followed by NCS provided only the arabino-chloro lactone 48 in 40% isolated yield. Reduction with DIBAL-H and chlorination at 1-position afforded compound 50 in almost quantitative yield. Coupling of 50 with nicotinamide with the presence of $AgSbF_6$ gave 51 as a mixture of both α and β isomers, in which 3 predominates (β/α=4/1). The following deprotection and HPLC purification afforded desired 2'-deoxy-2'-arabino-chloro-NR 52 in 68% after two steps.

Figure 12:
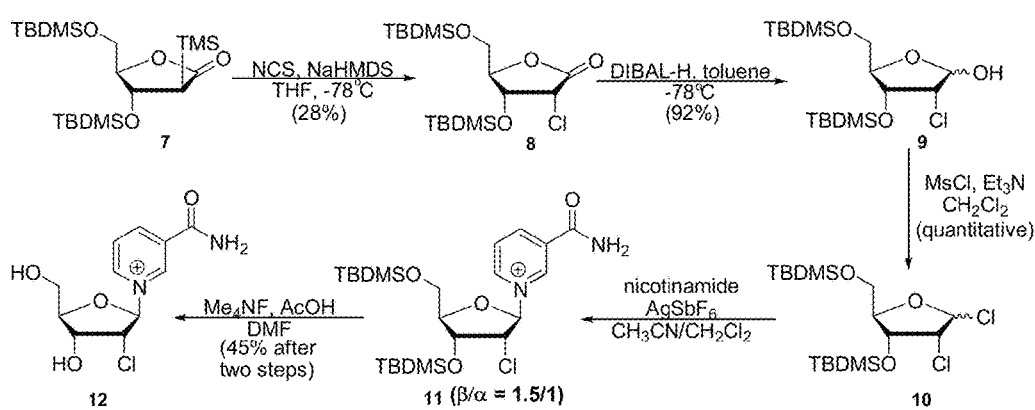
FIG. 12 illustrates a synthetic route to chlorinated nucleotides in accordance with another embodiment of the invention.

Synthesis of 2'-Deoxy-2'-ribo-chloro-NR is depicted in FIG. 12. Chlorination of 53 with NCS gave both arabino- and ribo-chloro lactones, from which the ribo lactone 54 was isolated in 28% yield. Conversion to the nucleoside was performed similarly to the fluorinated compounds described herein. 2'-deoxy-2'-ribo-chloro-NR was obtained in 45% yield after coupling and deprotection.

Figure 13:
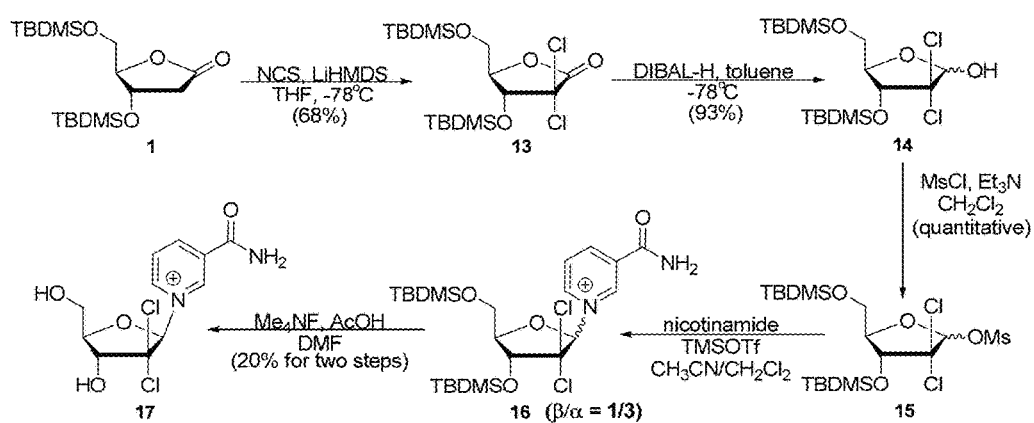
FIG. 13 illustrates a synthetic route to chlorinated nucleotides in accordance with another embodiment of the invention.

Preparation of the dichloro analog is depicted in FIG. 13. Gem-dichloro lactone 59 was obtained in one step with 68% yield starting from compound 47. NCS is a rather reactive chlorination agent, the introduction of the first chlorine substituent at 2-position makes the remaining proton even more acidic, thus allowing the second chlorination to occur in one pot. Coupling of 1-mesylate 61 with nicotinamide with the presence of TMSOTf afforded 62 as a mixture of β- and α-isomers (β/α=1/3), similar to what we have observed for the gem-difluoro analogue. Final deprotection provided 63 in 20% isolated yield after two steps.

Figure 14:
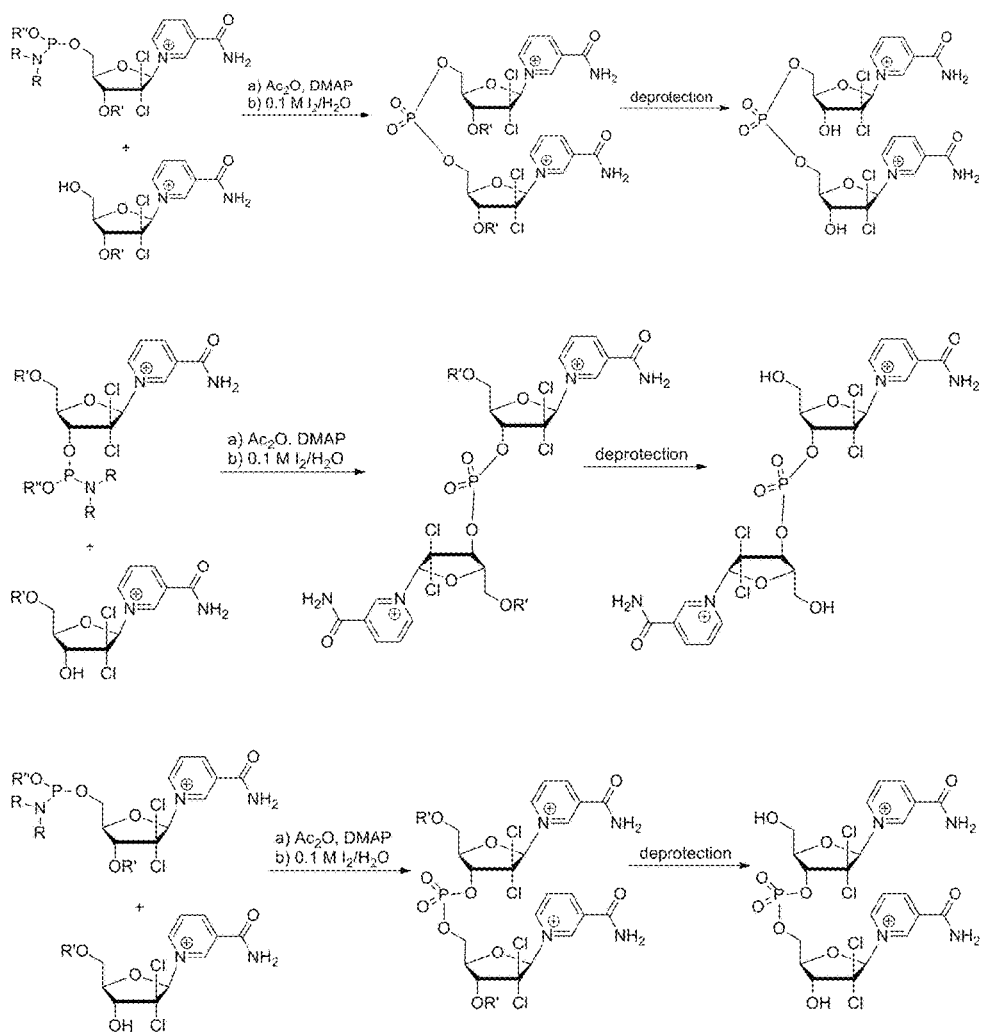
FIG. 14 illustrates a synthetic route to phosphate-linked nucleosides in accordance with another embodiment of the invention.
Figure 15:
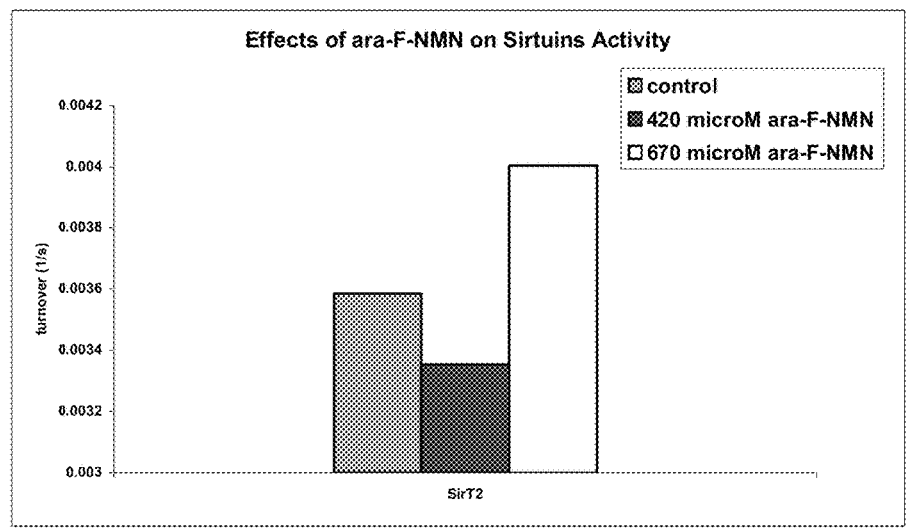
FIG. 15 illustrates the effects of ara-F-NNM on activity of sirtuins.

Synthetic routes to certain embodiments of the invention wherein the compounds comprise a phosphate linker group linking ribose moieties are depicted in FIG. 14.

In certain embodiments, the invention provides a polymer comprising as a monomeric unit any of the compound embodiments of the invention.

The invention further discloses a method of treating a disorder or a symptom thereof in a subject, wherein the disorder is selected from the group consisting of an abnormal cellular proliferation, a viral infection, and an autoimmune disorder, which method comprises administering to a subject in need thereof an effect amount of a compound of the compound embodiments of the invention, the polymer embodiment of the invention, or a pharmaceutically acceptable salt thereof, wherein the disorder or symptom thereof is treated.

In any of the embodiments of the invention, abnormal cellular proliferation can be a cancer. The cancer can be any cancer in any organ, for example, a cancer is selected from the group consisting of glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma, and combinations thereof. The cancer can be any suitable cancer, for example, follicular thyroid carcinoma, colorectal cancer, pancreatic cancer, leukemias, such as myeloid leukemia, prostate cancer, hepatic cancer, hepatocellular carcinoma, cholangiocarcinoma, cervical and ovarian cancer, cancers of glial origin and renal cancer.

Viral infections include but are not limited to HIV, hepatitis B and C, herpes simplex, chronic ear infections, osteomyelitis, Lyme disease, and chlamadia. Non-limiting examples of suitable autoimmune disorders include psoriasis, atopic dermatitis, rheumatoid arthritis, osteoarthritis, scleroderma and systemic lupus erythematosus.

The novel compounds disclosed herein, as well as known compounds whose synthesis is described herein, have several utilities.

They may modulate the following targets:

Ribonucleotide reductase (similar to Clofarabine and Gemcitabine, each of which inhibits said enzyme)

Thymidylate synthase (similar to Fluorouracil, Capecitabine, Tegafur, Carmofur, Floxuridine, each a fluorine-containing compound that inhibits this enzyme)

DNA polymerase (similar to fludara, which inhibits said enzyme)

poly(ADP-ribose) polymerases (PARPs)

Sirtuins

CD38

They have the following therapeutic utilities:

Anticancer activities, such as those exhibited by Fludara, Gemcitabine, and the fluorinated nucleoside analogs disclosed in Published PCT Application WO/2007/112028 assigned to RFS Pharma, LLC, which is incorporated herein in its entirety, and similar to CD38, sirtuin and PARP inhibitors currently in development.

Antiviral activities, such as those exhibited by fluorinated nucleoside analogs disclosed in Published PCT Application WO/2007/112028 assigned to RFS Pharma, LLC, which is incorporated herein in its entirety.

Metabolic diseases, including wasting, diabetes, diseases of aging.

Incorporated into oligonucleotides, interfering RNA reagents, aptamers, and other higher-order structures, as treatments for any numbers of diseases for which interfering RNA, antisense, or aptamers are possible They have the following utilities as reagents due to their high stability:

As a reagent on a purification column

As a reagent in crystallization reactions

As electron sinks

Incorporated into oligonucleotides, interfering RNA reagents, aptamers, and other higher-order structures, as more robust reagents The following examples further illustrate the invention but, of course, should not be construed as in any way limiting its scope.

EXAMPLE 1

2-deoxy-3,5-di-O-(p-chlorobenzoyl)-D-ribonolactone (5). A solution of methyl-2-deoxy-3,5-di-O-(p-chlorobenzoyl)-D-ribofuranoside (500 mg, 1.18 mmol) in 20 mL of 80% acetic acid aqueous solution and 2 mL of 10% aqueous HCl was heated to reflux for an hour and then cooled to room temperature. Water was added, organic phase was washed with water, saturated NaHCO$_3$ solution, brine and dried over anhydrous Na$_2$SO$_4$. Solvent was removed under vacuo and crude product was dissolved in 10 mL of CH$_2$Cl$_2$, to this solution was added PCC (294 mg, 1.36 mmol). Reaction was stirred at room temperature and monitored by TLC, once it was completed, PCC was filtered off, filtrate was concentrated and purified by column chromatography (hexanes:ethyl acetate 4:1) to afford 5 (190 mg, 0.46 mmol, 40% yield for two steps) as white solid. mp=89-90° C. $^1$H NMR (CDCl$_3$, 400 MHz), δ ppm: 2.81 (dd, J=2.1, 18.8 Hz, 1H), 3.12 (dd, J=7.5, 18.9 Hz, 1H), 4.60 (dd, J=3.7, 12.3 Hz, 1H), 4.68 (dd, J=3.8, 12.3 Hz, 1H), 4.92 (m, 1H), 5.58 (dt, J=1.8, 7.5 Hz, 1H), 7.42 (m, 4H), 7.93 (m, 4H). $^{13}$C NMR (125 MHz, CDCl$_3$), δ ppm: 34.9, 63.9, 71.9, 82.2, 127.0, 127.4, 129.09, 129.11, 131.0, 131.2, 140.3, 140.6, 164.98, 165.02, 173.5. HRMS (ESI): calcd. for C$_{19}$H$_{14}$C$_{12}$O$_6$: 408.0167. Found: 408.017.

EXAMPLE 2

(S)-4-hydroxymethyl-2-buten-4-olide (6). To a flame-dried round-bottom flask were added 5 (155 mg, 0.38 mmol) and NFSi (120 mg, 0.38 mmol) in 5 mL of anhydrous THF. The solution was cooled to −78° C. and LiHMDS in THF solution (0.456 mL, 0.456 mmol) was added dropwise. Reaction mixture was allowed to stir at −78° C. for additional hour and then quenched by saturated NH$_4$Cl solution. Organic layer was washed by saturated NaHCO$_3$ solution, water, brine and dried over anhydrous Na$_2$SO$_4$. Column chromatography (hexanes:ethyl acetate 4:1~2:1) gave 6 (62 mg, 0.24 mmol, 65%) as white solid. mp=115-116° C. $^1$H NMR (CDCl$_3$, 400 MHz), δ ppm: 4.55 (dd, J=4.8, 12.0 Hz, 1H), 4.61 (dd, J=3.7, 12.1 Hz, 1H), 5.34 (m, 1H), 6.22 (dd, J=2.1, 5.8 Hz, 1H), 7.40 (d, J=8.6 Hz, 2H), 7.48 (dd, J=1.5, 5.7 Hz, 1H), 7.91 (d, J=8.6 Hz, 2H). $^{13}$C NMR (125 MHz, CDCl$_3$), δ ppm: 63.1, 76.9, 80.8, 123.6, 127.5, 128.91, 128.96, 131.1, 131.6, 140.2, 152.1, 165.2, 172.1. HRMS (ESI): calcd. for C$_{12}$H$_9$ClO$_4$: 252.0189. Found: 252.0188.

EXAMPLE 3

2-deoxy-3,5-di-O-(t-butyldimethylsilyl)-D-ribonolactone (7). To a solution of 2-deoxy-D-ribose (1.0 g, 7.45 mmol) in 6 mL of water was added Br$_2$ (2 mL). The flask was sealed and the content was stirred at room temperature for 5 days. The resulting mixture was neutralized by adding silver carbonate until the pH was 7. The mixture was filtered and the filtrate was concentrated under reduced pressure to yield 2-deoxyribonolactone as a yellow oil. Without further purification, the crude product was dissolved in 20 mL of anhydrous DMF, and imidazole (2.53 g, 37.3 mmol) and t-butyldimethylsilyl chloride (4.5 g, 29.8 mmol) were added. The resulting solution was stirred at room temperature for 24 h, and quenched by addition of water. Water layer was extracted by ethyl acetate (3×10 mL), organic layers were combined, washed with brine and dried over anhydrous Na$_2$SO$_4$. Crude product was concentrated in vacuo. Flash chromatography (hexanes:ethyl acetate 20:1) afforded 7 (3.2 g, 8.9 mmol, 89% yield after two steps) as white solid. mp=72-73° C. $^1$H NMR (CDCl$_3$, 400 MHz), δ ppm: 0.038 (s, 3H), 0.051 (s, 3H), 0.062 (s, 6H), 0.085 (s, 18H), 2.36 (dd, J=2.6, 17.7 Hz, 1H), 2.79 (dd, J=6.7, 17.7 Hz, 1H), 3.73 (dd, J=2.5, 11.5 Hz, 1H), 3.78 (dd, J=3.4, 11.5 Hz, 1H), 4.30 (dd, J=2.5, 5.2 Hz, 1H), 4.48 (dt, J=2.3, 6.6 Hz, 1H). $^{13}$C NMR (125 MHz, CDCl$_3$), δ ppm: −5.7, −5.5, −4.9, −4.8, 17.9, 18.2, 25.7, 25.8, 39.0, 62.5, 69.6, 88.1, 175.8. HRMS (ESI): calcd. for C$_{17}$H$_{36}$O$_4$Si$_2$: 360.2152. Found: 360.2155.

EXAMPLE 4

2-deoxy-2-fluoro-3,5-di-O-(t-butyldimethylsilyl)-D-ribonolactone (8). To a flame-dried 100 mL round-bottom flask were added 7 (1.8 g, 5 mmol) and NFSi (2.36 g, 7.5 mmol) in 20 mL of anhydrous THF. The solution was cooled to −78° C. and 6.5 mL (6.5 mmol) of a 1 M solution of LiHMDS in THF was added dropwise over a period of 10 mins. This was allowed to stir at −78° C. for an additional hour and was quenched by saturated NH$_4$Cl. The mixture was allowed to warm to room temperature, water layer was extracted by ethyl acetate (3×10 mL), organic layers were combined, washed with saturated NaHCO$_3$, water, brine, dried over anhydrous Na$_2$SO$_4$ and concentrated in vacuo. Crude product was purified by flash chromatography (hexanes:ethyl acetate 20:1) to afford both 8 (1.1 g, 29 mmol, 58%) and 9 (0.5 g, 1.9 mmol, 38%) also as white solid. 8 mp=49-50° C. $^1$H NMR (CDCl$_3$, 400 MHz), δ ppm: 0.060 (s, 3H), 0.065 (s, 3H), 0.107 (s, 3H), 0.128 (s, 3H), 0.87 (s, 9H), 0.89 (s, 9H), 3.76 (dd, J=2.5, 12.4 Hz, 1H), 3.95 (dt, J=2.1, 12.4 Hz, 1H), 4.10 (dt, J=2.0, 7.7 Hz, 1H), 4.70 (dt, J=7.8, 18.9 Hz, 1H), 5.09 (dd, J=8.0, 51.7 Hz, 1H). $^{13}$C NMR (100 MHz, CDCl$_3$), δ ppm: −5.5, −5.4, −5.2, −4.8, 17.9, 18.2, 25.5, 25.7, 59.4, 71.3, 71.5, 80.6, 80.7, 91.3, 93.3, 168.5, 168.7. HRMS (ESI): calcd. for C$_{17}$H$_{35}$FO$_4$Si$_2$: 378.2058. Found: 378.206.

EXAMPLE 5

4-(t-butyldimethylsiloxy)methyl-4-fluoro-2-buten-4-olide (9) mp=85-87° C. $^1$H NMR (CDCl$_3$, 500 MHz), δ ppm: 0.045 (s, 3H), 0.057 (s, 3H), 0.85 (s, 9H), 3.86 (dd, J=11.3, 15.9 Hz, 1H), 4.04 (dd, J=7.8, 11.3 Hz, 1H), 6.25 (d, J=5.7 Hz, 1H), 7.33 (d, J=5.7 Hz, 1H). $^{13}$C NMR (125 MHz, CDCl$_3$), δ ppm: −5.62, −5.58, −18.1, 25.6, 63.5, 63.8, 114.4, 116.3, 125.01, 125.05, 149.7, 149.8, 168.39, 168.41. HRMS (ESI): calcd. for C$_{11}$H$_{19}$FO$_3$Si: 246.1087. Found: 246.1085.

EXAMPLE 6

2-deoxy-3,5-di-O-(triisopropylsilyl)-D-ribonolactone (10). 2-Deoxy-D-ribonolactone (1.1 g, 8.3 mmol) was dissolved in 10 mL of anhydrous DMF, to this solution were added imidazole (3.4 g, 50 mmol) and triisopropylsilyl chloride (6.4 g, 33 mmol) were added. The resulting solution was stirred at room temperature for 24 h, and quenched by addition of water. Water layer was extracted by ethyl acetate (3×10 mL), organic layers were combined, washed with brine and dried over anhydrous Na$_2$SO$_4$. Crude product was concentrated in vacuo. Column chromatography (hexanes:ethyl acetate 25:1~20:1) provided 10 (3.4 g, 7.7 mmol, 92%) as colorless oil. $^1$H NMR (CDCl$_3$, 400 MHz), δ ppm: 1.05 (stack, 42H), 2.41 (dd, J=1.9, 17.6 Hz, 1H), 2.86 (dd, J=6.6, 17.6 Hz, 1H), 3.83 (dd, J=2.6, 9.4 Hz, 1H), 3.91 (dd, J=3.0, 11.4 Hz, 1H), 4.39 (s, 1H), 4.65 (d, J=6.5, 1H). $^{13}$C NMR (125 MHz, CDCl$_3$), δ ppm: 11.9, 12.1, 18.0, 39.7, 63.4, 70.1, 88.9, 176.1. HRMS (ESI): calcd. for C$_{23}$H$_{48}$O$_4$Si$_2$: 444.3091. Found: 444.3094. MM2 calculations on lithium enolate of 10 were performed using CHEM3D version 10.0 Minimized energy to minimum RMS gradient of 0.100.

EXAMPLE 7

2-deoxy-2-fluoro-3,5-di-O-(triisopropylsilyl)-D-ribonolactone (11). Compound 11 was obtained according to the fluorination procedure to synthesize 8, using 10 (2 g, 4.5 mmol) as the starting material. Column chromatography (hexanes:ethyl acetate 30:1) provided 11 (1.5 g, 3.25 mmol, 72%) as a white solid. mp=38-39° C. $^1$H NMR (CDCl$_3$, 400 MHz), δ ppm: 1.07 (stack, 42H), 3.91 (dd, J=2.4, 12.1 Hz, 1H), 4.08 (dt, J=2.1, 12.1 Hz, 1H), 4.16 (dt, J=2.1, 7.0 Hz, 1H), 4.92 (dt, J=7.2, 18.8 Hz, 1H), 5.10 (dd, J=7.4, 51.3 Hz, 1H). $^{13}$C NMR (100 MHz, CDCl$_3$), δ ppm: 11.9, 12.1, 17.7, 17.80, 17.84, 17.86, 60.3, 71.6, 71.8, 81.8, 81.9, 91.7, 93.7, 168.6, 168.8. NOE identified between H$_2$ and H$_4$ in NOESY. HRMS (ESI): calcd. for C$_{23}$H$_{47}$FO$_4$Si$_2$: 462.2997. Found: 462.2993.

EXAMPLE 8

2-deoxy-2-fluoro-3,5-di-O-(triisopropylsilyl)-D-arabinofuranose (12). 11 (200 mg, 0.43 mmol) was dissolved in 1.5 mL of anhydrous toluene and cooled to −78° C. To this solution was added 3.02 mL of DIBAL-H in THF solution (3.02 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated NaHCO$_3$, water, brine, dried over anhydrous Na$_2$SO$_4$ and concentrated in vacuo. Column chromatography (hexanes:ethyl acetate 15:1) afforded 12 (181 mg, 0.39 mmol, 91%) as colorless oil. $^1$H NMR (CDCl$_3$, 400 MHz), δ ppm: 1.07 (stack, 54H), 3.46 (d, J=10.9 Hz, 1H), 3.60 (m, 1.27H), 3.78 (m, 1.57H), 3.95 (q, J=3.7 Hz, 0.28H), 4.32 (m, 1H), 4.49 (dd, J=0.9, 12.6 Hz, 1H), 4.63 (t, J=4.0 Hz, 0.14H), 4.67 (t, J=4.0 Hz, 0.14H), 4.81 (t, J=4.1 Hz, 0.28H), 4.83 (dd, J=0.8, 50.2 Hz, 1H), 5.31 (m, 0.3H), 5.35 (t, J=10.1 Hz, 1H). $^{13}$C NMR (125 MHz, CDCl$_3$), δ ppm: 12.0, 12.2, 18.0, 63.2, 75.4, 75.5, 75.6, 87.6, 87.7, 95.9, 97.5, 97.7, 98.8, 98.9, 100.8, 101.0. HRMS (ESI): calcd. for C$_{23}$H$_{49}$FO$_4$Si$_2$: 464.3153. Found: 464.3162.

EXAMPLE 9

2-deoxy-2,2-difluoro-3,5-di-O-(triisopropylsilyl)-D-ribonolactone (13). Compound 13 was obtained according to the fluorination procedure to synthesize 8, using 11 (92 mg, 0.2 mmol) as the starting material. Column chromatograph (hexanes:ethyl acetate 40:1) provided 13 (68 mg, 0.14 mmol, 71%) as pale yellow oil. $^1$H NMR (CDCl$_3$, 400 MHz), δ ppm: 1.08 (stack, 42H), 3.96 (dd, J=2.4, 12.0 Hz, 1H), 4.08 (dt, J=2.6, 12.1 Hz, 1H), 4.31 (m, 1H), 4.76 (dt, J=6.0, 11.2 Hz, 1H). $^{13}$C NMR (100 MHz, CDCl$_3$), δ ppm: 11.4, 11.45, 11.8, 12.1, 17.2, 17.3, 17.36, 17.43, 59.6, 68.3, 68.5, 68.6, 68.7, 82.5, 82.6, 109.9, 112.4, 115.0, 163.3, 163.6, 164.0. HRMS (ESI): calcd. for C$_{23}$H$_{46}$F$_2$O$_4$Si$_2$: 480.2903. Found: 480.2901.

EXAMPLE 10

2-deoxy-2,2-difluoro-3,5-di-O-(triisopropylsilyl)-D-ribofuranose (14). Compound 14 was obtained according to the reduction procedure to synthesize 12, using 13 (160 mg, 0.33 mmol) as the starting material. Column chromatography (hexanes:ethyl acetate 10:1) provided 14 (146 mg, 0.3 mmol, 91%) as colorless oil. $^1$H NMR (CDCl$_3$, 400 MHz), δ ppm: 1.04 (stack, 78H), 3.48 (d, J=11.3 Hz, 1H), 3.67 (m, 1.8H), 3.81 (m, 1.8H), 3.88 (dt, J=2.1, 11.2 Hz, 1H), 4.02 (m, 0.8H), 4.24 (m, 1H), 4.39 (dt, J=2.0, 10.7 Hz, 1H), 4.67 (m, 0.8H), 5.02 (dd, J=5.1, 9.8 Hz, 0.8H), 5.11 (dd, J=6.1, 11.3 Hz, 1H). $^{13}$C NMR (125 MHz, CDCl$_3$), δ ppm: 11.87, 11.90, 12.1, 12.3, 17.72, 17.73, 17.78, 17.83, 17.86, 17.89, 62.2, 62.34, 62.36, 69.6, 69.7, 69.8, 70.0, 71.9, 72.0, 72.1, 72.3, 83.95, 84.02, 85.3, 95.3, 95.5, 95.6, 95.8, 96.0, 96.2, 96.3, 96.5, 119.5, 120.1, 121.5, 121.6, 122.1, 123.6, 124.2. HRMS (ESI): calcd. for C$_{23}$H$_{48}$F$_2$O$_4$Si$_2$: 482.3059. Found: 482.3054.

EXAMPLE 11

2-deoxy-2-bromo-3,5-di-O-(t-butyldimethylsilyl)-D-ribono, arabino-lactones (15). To a solution of 7 (180 mg, 0.5 mmol) and triethylamine (303 mg, 3 mmol) in 6 mL of CH$_2$Cl$_2$ at 0° C. was added TMSOTf (333 mg, 1.5 mmol), and the solution was stirred at this temperature for 30 mins. A solution of NBS (134 mg, 0.75 mmol) in 1.5 mL of CH$_2$Cl$_2$ was added, and the stirring was continued for 1 h at 0° C. Reaction mixture was poured into saturated NaHCO$_3$ solution, extracted with CH$_2$Cl$_2$ (3×5 mL). Combined organic layer was washed with brine, dried over anhydrous Na$_2$SO$_4$ and concentrated in vacuo. Flash chromatography (hexanes:ethyl acetate 35:1) afforded a mixture of two isomers of 15 (120 mg, 0.27 mmol, 55%, 1:1.4, arabino/ribono) as pure pale yellow liquid. A small amount of this mixture was separated to obtain the pure compounds. Stereochemistry was determined by an observed NOE between the 2 and 4 protons of the arabino-isomer. Arabino-15: $^1$H NMR (CDCl$_3$, 500 MHz), δ ppm: 0.041 (s, 3H), 0.053 (s, 3H), 0.10 (s, 3H), 0.13 (s, 3H), 0.85 (s, 9H), 0.90 (s, 9H), 3.76 (dd, J=2.0, 12.2 Hz, 1H), 3.93 (dd, J=2.2, 12.2 Hz, 1H), 4.31 (m, 1H), 4.39 (t, J=5.0 Hz, 1H), 4.47 (d, J=5.7 Hz, 1H). $^{13}$C NMR (125 MHz, CDCl$_3$), δ ppm: −5.6, −5.5, −5.0, −4.8, 18.1, 18.2, 25.6, 25.8, 46.1, 60.3, 68.8, 85.0, 170.9. HRMS (ESI): calcd. for C$_{17}$H$_{35}$BrO$_4$Si$_2$: 438.1257. Found: 438.1261. Ribono-15: $^1$H NMR (CDCl$_3$, 500 MHz), δ ppm: 0.058 (s, 3H), 0.062 (s, 3H), 0.116 (s, 3H), 0.172 (s, 3H), 0.87 (s, 9H), 0.88 (s, 9H), 3.79 (dd, J=3.0, 12.0 Hz, 1H), 3.92 (dd, J=3.3, 12.0 Hz, 1H), 4.21 (m, 1H), 4.37 (d, J=6.9 Hz, 1H), 4.67 (dd, J=6.1, 6.6 Hz, 1H). $^{13}$C NMR (125 MHz, CDCl$_3$), δ ppm: −5.5, −5.4, −5.0, −4.1, 17.8, 18.2, 25.6, 25.7, 46.1, 60.2, 75.6, 85.3, 170.1. HRMS (ESI): calcd. for C$_{17}$H$_{35}$BrO$_4$Si$_2$: 438.1257. Found: 438.1258.

EXAMPLE 12

(2-R and 2-S)-2-deoxy-2-bromo-2-fluoro-3,5-di-O-(t-butyldimethylsilyl)-D-ribonolactone (16). Compound 16 was obtained according to the fluorination procedure to synthesize 8, using 15 (400 mg, 0.91 mmol) as the starting material. Column chromatography (hexanes:ethyl acetate 30:1) provided 16 (230 mg, 0.5 mmol, 55%) as pale yellow oil. $^1$H NMR (CDCl$_3$, 500 MHz), δ ppm: 0.058 (s, 3H), 0.065 (s, 3H), 0.13 (s, 3H), 0.17 (s, 3H), 0.86 (s, 9H), 0.93 (s, 9H), 3.77 (dd, J=1.9, 12.7 Hz, 1H), 4.00 (m, 2H), 4.53 (dd, J=8.0, 15.4 Hz, 1H). $^{13}$C NMR (125 MHz, CDCl$_3$), δ ppm: −5.5, −5.4, −5.2, −4.6, 18.0, 18.2, 25.5, 25.7, 58.3, 72.0, 72.2, 80.6, 80.7, 98.2, 100.5, 165.6, 165.8. HRMS (ESI): calcd. for C$_{17}$H$_{34}$BrFO$_4$Si$_2$: 456.1163. Found: 456.1178.

EXAMPLE 13

Debromination of 16 yielding 8. 16 (60 mg, 0.13 mmol), tributyltinhydride (83 mg, 0.28 mmol) and AIBN (3 mg, 0.018 mmol) were dissolved in 1 mL of toluene and stirred at 90° C. for 24 h. Solvent was evaporated and residue was dissolved in acetonitrile, washed with hexanes to remove organotin compounds. Solvent was again concentrated in vacuo, and NMR identified it as compound 8 described previously.

EXAMPLE 14

2-deoxy-2-trimethylsilyl-3,5-di-O-(t-butyldimethylsilyl)-D-arabinolactone (17). To a solution of 7 (1 g, 2.78 mmol), and triethylamine (1.68 g, 16.68 mmol) in 28 mL of $CH_2Cl_2$ at 0° C. was added TMSOTf (1.85 g, 8.34 mmol) dropwise. The solution was stirred at this temperature for another 2 h and then quenched with saturated $NH_4Cl$. The mixture was allowed to warm to room temperature, water layer was extracted by $CH_2Cl_2$ (3×10 mL), organic layers were combined, washed with saturated $NaHCO_3$, water, brine, dried over anhydrous $Na_2SO_4$ and concentrated in vacuo. Crude product was purified by flash chromatography (hexanes:ethyl acetate 25:1) to afford 17 (850 mg, 1.97 mmol, 71%) as a white solid. mp=70-71° C. $^1H$ NMR ($CDCl_3$, 400 MHz), δ ppm: 0.067 (s, 6H), 0.074 (s, 6H), 0.19 (s, 9H), 0.85 (s, 9H), 0.89 (s, 9H), 2.17 (d, J=2.5 Hz), 3.50 (dd, J=7.7, 10.7 Hz, 1H), 3.76 (dd, J=7.1, 12.2 Hz, 1H), 4.27 (m, 1H), 4.45 (t, J=2.2 Hz, 1H). $^{13}C$ NMR (125 MHz, $CDCl_3$), δ ppm: −5.4, −5.3, −4.7, −4.2, −1.7, −0.8, 17.7, 18.4, 25.6, 25.8, 25.90, 25.94, 42.2, 62.2, 71.8, 87.4, 177.7. HRMS (ESI): calcd. for $C_{20}H_{44}O_4Si_3$: 432.2547. Found: 432.2553.

EXAMPLE 15

2-deoxy-2-fluoro-3,5-di-O-(t-butyldimethylsilyl)-D-ribonolactone (18). Compound 18 was obtained according to the fluorination procedure to synthesize 8, using 17 (780 mg, 1.81 mmol) as the starting material. Column chromatograph (hexanes:ethyl acetate 30:1~10:1) provided both 18 (226 mg, 0.60 mmol, 33%) and 7 (400 mg, 1.11 mmol, 61%) as white solid. mp=75-77° C. $^1H$ NMR ($CDCl_3$, 400 MHz), δ ppm: 0.046 (s, 3H), 0.061 (s, 3H), 0.087 (s, 6H), 0.86 (s, 9H), 0.87 (s, 9H), 3.77 (dd, J=1.7, 11.9 Hz, 1H), 3.84 (dd, J=2.6, 12.0 Hz, 2H), 4.37 (d, J=2.1 Hz, 1H), 4.43 (d, J=5.2 Hz, 1H), 5.21 (dd, J=5.3, 50 Hz, 1H). $^{13}C$ NMR (125 MHz, $CDCl_3$), δ ppm: −5.7, −5.6, −5.3, −4.9, −4.8, 18.2, 18.3, 25.6, 25.8, 62.3, 70.3, 70.4, 71.8, 84.2, 85.8, 86.4, 88.1, 171.1. HRMS (ESI): calcd. for $C_{17}H_{35}FO_4Si_2$: 378.2058. Found: 378.2059.

EXAMPLE 16

2-deoxy-2-fluoro-3,5-di-O-(t-butyldimethylsilyl)-D-ribofuranose (19). Compound 19 was obtained according to the reduction procedure to synthesize 12, using 18 (100 mg, 0.22 mmol) as the starting material. Column chromatography (hexanes:ethyl acetate 15:1) provided 19 (95 mg, 0.205 mmol, 95%) as colorless oil. $^1H$ NMR ($CDCl_3$, 500 MHz), δ ppm: 1.02 (stack, 96H), 3.28 (d, J=7.3 Hz, 2.2H), 3.68 (dd, J=3.7, 11 Hz, 1H), 3.76 (dd, J=2.7, 11 Hz, 1H), 3.80 (dd, J=1.8, 11 Hz, 2.2H), 3.92 (dd, J=2.2, 11 Hz, 2.2H), 4.09 (dt, J=1.9, 6.7 Hz, 2.2H), 4.14 (dd, J=1.2, 12.3 Hz, 1H), 4.23 (s, 1H), 4.49 (dd, J=1.7, 2.8 Hz, 1H), 4.59 (dd, J=3.7, 53.4 Hz, 2.2H), 4.71 (ddd, J=3.8, 10.4, 23.5 Hz, 1H), 4.85 (dt, J=4.4, 51.7 Hz, 1H), 5.24 (dd, J=4.2, 8 Hz, 1H), 5.27 (t, J=6.1 Hz, 2.2H). $^{13}C$ NMR (125 MHz, $CDCl_3$), δ ppm: 11.83, 11.85, 11.9, 12.2, 17.71, 17.72, 17.81, 17.85, 17.87, 17.88, 61.8, 63.5, 69.8, 69.9, 71.9, 72.0, 84.0, 85.67, 85.70, 87.6, 89.2, 93.5, 95.0, 95.7, 95.9, 99.1, 99.3. HRMS (ESI): calcd. for $C_{17}H_{37}FO_4Si_2$: 380.2214. Found: 380.2212.

EXAMPLE 17

1-chloro-2-deoxy-2-fluoro-3,5-di-O-(triisopropylsilyl)-D-arabinofuranose (20). 12 (40 mg, 0.086 mmol) was dissolved in 0.5 mL of $CH_2Cl_2$ and triethylamine (12.2 mg, 0.12 mmol). To this solution was added at 0° C. methanesulfonyl chloride (11.5 mg, 0.1 mmol). After 3 h of stirring under argon at room temperature, the mixture was evaporated in vacuo, and the residue was taken up in ethyl acetate. The solution was washed with saturated $NaHCO_3$, followed by 1 M HCl, water and brine. Solvent was concentrated under reduced pressure to afford 20 (40 mg, 0.086 mmol, almost quantitatively) as yellow liquid. $^1H$ NMR ($CDCl_3$, 400 MHz), δ ppm: 1.08 (stack, 42H), 3.89 (dd, J=3.7, 11.7 Hz, 1H), 3.96 (dd, J=2.9, 11.7 Hz, 1H), 4.30 (dd, J=3.4, 8.3 Hz, 1H), 4.58 (dd, J=5.1, 14.8 Hz, 1H), 5.12 (d, 51.7 Hz, 1H), 6.15 (d, J=12.5 Hz, 1H). $^{13}C$ NMR (125 MHz, $CDCl_3$), δ ppm: 11.9, 12.0, 17.80, 17.84, 17.9, 61.4, 75.1, 75.4, 88.61, 88.64, 95.3, 95.6, 103.8, 105.3. HRMS (ESI): calcd. for $C_{23}H_{48}ClFO_3Si_2$: 482.2815. Found: 482.2822.

EXAMPLE 18

1-(2'-deoxy-2'-fluoro-3',5'-di-O-(triisopropylsilyl)arabinofuranosyl)-nicotinamide (21). 20 (25 mg, 0.052 mmol) and nicotinamide (15 mg, 0.12 mmol) were dissolved in 1 mL of $CH_2Cl_2$. To this solution at 0° C. was added a ice-cold solution of nicotinamide (15 mg, 0.12 mmol) and $AgSbF_6$ (36 mg, 0.104 mmol) in 1.5 mL of acetonitrile. Reaction mixture was kept at room temperature overnight. Solvent was evaporated under reduce pressure and the residue was redissolved in methanol and pass through a short pad of celite. Concentrated crude product (which contained a mixture of α and β isomers) was examined by NMR and used for the next step without further purification.

EXAMPLE 19

1-(2'-deoxy-2'-fluoro-arabinofuranosyl)-nicotinamide (22). To a solution of 21 (25 mg, 0.044 mmol) in 1 mL of DMF were added acetic acid (10.6 mg, 0.176 mmol) and tetramethylammonnium fluoride (16.4 mg, 0.176 mmol). The reaction was stirred at room temperature overnight, then was concentrated and purified by HPLC on a Waters RP-18 XBridge PrepShield 19×50 mm column (solvent was 20 mM ammonium acetate, compounds were eluted at a flow rate of 2 mL/min) to afford 22 (β-isomer, $t_R$=8 min, 7 mg, 0.027 mmol, 62%) and α-isomer ($t_R$=6.7 min, 2 mg, 0.008 mmol, 18%). β-isomer $^1H$ NMR ($D_2O$, 400 MHz), δ ppm: 3.88 (dd, J=4.8, 13.0 Hz, 1H), 4.0 (dd, J=1.9, 12.9 Hz, 1H), 4.28 (dd, J=4.7, 8.3 Hz, 1H), 4.51 (dt, J=5.5, 17.6 Hz, 1H), 5.5 (dt, J=4.6, 51.3 Hz, 1H), 6.68 (dd, J=4.7, 9.8 Hz, 1H), 8.23, (t, J=6.6 Hz, 1H), 8.95 (d, J=8.1 Hz, 1H), 9.18 (d, J=6.2 Hz, 1H), 9.57 (s, 1H). $^{13}C$ NMR (125 MHz, $D_2O$), δ ppm: 59.4, 71.1, 71.3, 85.07, 85.11, 93.9, 94.0, 94.1, 95.6, 128.1, 133.8, 141.5, 143.8, 146.1, 165.7. HRMS (ESI): calcd. for $C_{11}H_{13}FN_2O_4$: 256.0859. Found: 256.0865.

EXAMPLE 20

(1R,2R)-1-chloro-2-deoxy-2-fluoro-3,5-di-O-(t-butyldimethylsilyl)-D-ribofuranose (23). Compound 23 was obtained according to the chlorination procedure to synthesize 20, using 19 (10 mg, 0.021 mmol) as the starting material to afford 23 (10 mg, 0.021 mmol, almost quantitatively) as yellow liquid. $^1$H NMR (CDCl$_3$, 500 MHz), δ ppm: 1.02 (stack, 51H), 3.86 (stack, 3.4H), 4.02 (dd, J=1.8, 11.8 Hz, 0.7H), 4.10 (m, 0.7H), 4.31 (d, J=2.1 Hz, 1H), 4.55 (quintet, J=3 Hz, 1H), 4.82 (dt, J=4.7, 49 Hz, 1H), 4.95 (dd, J=3.3, 45 Hz, 0.7H), 6.06 (d, J=11.1 Hz, 0.7H), 6.21 (d, J=4.1 Hz, 1H). $^{13}$C NMR (125 MHz, CDCl$_3$), δ ppm: 11.8, 11.9, 12.1, 12.2, 17.77, 17.81, 17.84, 17.86, 17.95, 17.96, 31.5, 52.5, 61.6, 62.3, 68.6, 68.8, 85.8, 87.9, 88.7, 89.6, 92.8, 93.0, 93.4, 93.7, 95.6, 97.2. HRMS (ESI): calcd. for C$_{17}$H$_{36}$ClFO$_3$Si$_2$: 398.1876. Found: 398.1880.

EXAMPLE 21

1-(2'-deoxy-2'-fluoro-3',5'-di-O-(t-butyldimethylsilyl)-D-ribofuranosyl)-nicotinamide (24). 23 (11 mg, 0.026 mmol) and nicotinamide (8 mg, 0.065 mmol) were dissolved in 1 mL of CH$_2$Cl$_2$. To this solution at 0° C. was added a ice-cold solution of nicotinamide (8 mg, 0.065 mmol) and AgSbF$_6$ (8.9 mg, 0.026 mmol) in 1.5 mL of acetonitrile. Reaction mixture was kept at room temperature overnight. Solvent was evaporated under reduce pressure and the residue was redissolved in methanol and pass through a short pad of celite. Concentrated crude product was examined by NMR and used for the next step without further purification.

EXAMPLE 22

1-(2-deoxy-2-fluoro-D-ribofuranosyl)-nicotinamide (25). Compound 25 was obtained according to the deprotection procedure to synthesize 22, using 24 (12.6 mg, 0.026 mmol) as the starting material. Crude product was purified by HPLC on a Waters RP-18 XBridge PrepShield 19×50 mm column (solvent was 20 mM ammonium acetate, compounds were eluted at a flow rate of 2 mL/min) to afford 25 (β-isomer, t$_R$=14.5 min, 3 mg, 0.012 mmol, 45%) and α-isomer (t$_R$=10.6 min, 3.1 mg, 0.012 mmol, 46%). β-isomer: $^1$H NMR (D$_2$O, 600 MHz), δ ppm: 3.75 (dd, J=2.4, 13.2 Hz, 1H), 3.97 (dd, J=2.4, 13.8 Hz, 1H), 4.31 (m, 1H), 4.35 (m, 1H), 5.20 (dd, J=4.2, 49.2 Hz, 1H), 6.47 (d, J=14.4 Hz, 1H), 8.10 (t, J=7.8 Hz, 1H), 8.80 (dd, J=1.2, 7.8 Hz, 1H), 9.16 (d, J=6.6 Hz, 1H), 9.54 (s, 1H). $^{13}$C NMR (125 MHz, D$_2$O), δ ppm: 55.15, 55.18, 55.22, 58.8, 67.3, 67.4, 85.8, 94.2, 95.7, 97.2, 97.5, 128.5, 134.1, 140.8, 142.9, 145.9, 165.2. NOESY: NOE correlation between sugar H$_{3'}$ and nicotinamide H$_2$. HRMS (ESI): calcd. for C$_{11}$H$_{13}$FN$_2$O$_4$: 256.0859. Found: 256.0863. α-isomer: $^1$H NMR (D$_2$O, 500 MHz), δ ppm: 3.82 (dd, J=4.5, 10.5 Hz, 1H), 4.0 (dd, J=2.0, 10.5 Hz, 1H), 4.61 (m, 1H), 4.81 (m, 1H), 5.65 (dt, J=4.5, 43.5 Hz, 1H), 6.79 (dd, J=3.5, 8.5 Hz, 1H), 8.29, (dd, J=5.5, 7.0 Hz, 1H), 9.01 (d, J=6.5 Hz, 1H), 9.17 (d, J=5.5 Hz, 1H), 9.40 (s, 1H). NOESY: NOE correlations between sugar H$_{4'}$ and nicotinamide H$_2$, sugar H$_{4'}$ and nicotinamide H$_4$, sugar H$_{1'}$ and H$_{3'}$.

EXAMPLE 23

1-(2-deoxy-2-fluoro-D-ribofuranosyl)-nicotinamide (25). Compound 25 was obtained according to the deprotection procedure to synthesize 22, using 24 (12.6 mg, 0.026 mmol) as the starting material. Crude product was purified by HPLC on a Waters RP-18 XBridge PrepShield 19×50 mm column (solvent was 20 mM ammonium acetate, compounds were eluted at a flow rate of 2 mL/min) to afford 25 (β-isomer, t$_R$=14.5 min, 3 mg, 0.012 mmol, 45%) and α-isomer (t$_R$=10.6 min, 3.1 mg, 0.012 mmol, 46%). β-isomer: $^1$H NMR (D$_2$O, 600 MHz), δ ppm: 3.75 (dd, J=2.4, 13.2 Hz, 1H), 3.97 (dd, J=2.4, 13.8 Hz, 1H), 4.31 (m, 1H), 4.35 (m, 1H), 5.20 (dd, J=4.2, 49.2 Hz, 1H), 6.47 (d, J=14.4 Hz, 1H), 8.10 (t, J=7.8 Hz, 1H), 8.80 (dd, J=1.2, 7.8 Hz, 1H), 9.16 (d, J=6.6 Hz, 1H), 9.54 (s, 1H). $^{13}$C NMR (125 MHz, D$_2$O), δ ppm: 55.15, 55.18, 55.22, 58.8, 67.3, 67.4, 85.8, 94.2, 95.7, 97.2, 97.5, 128.5, 134.1, 140.8, 142.9, 145.9, 165.2. NOESY: NOE correlation between sugar H$_{3'}$ and nicotinamide H$_2$. HRMS (ESI): calcd. for C$_{11}$H$_{13}$FN$_2$O$_4$: 256.0859. Found: 256.0863. α-isomer: $^1$H NMR (D$_2$O, 500 MHz), δ ppm: 3.82 (dd, J=4.5, 10.5 Hz, 1H), 4.0 (dd, J=2.0, 10.5 Hz, 1H), 4.61 (m, 1H), 4.81 (m, 1H), 5.65 (dt, J=4.5, 43.5 Hz, 1H), 6.79 (dd, J=3.5, 8.5 Hz, 1H), 8.29, (dd, J=5.5, 7.0 Hz, 1H), 9.01 (d, J=6.5 Hz, 1H), 9.17 (d, J=5.5 Hz, 1H), 9.40 (s, 1H). NOESY: NOE correlations between sugar H$_{4'}$ and nicotinamide H$_2$, sugar H$_{4'}$ and nicotinamide H$_4$, sugar H$_{1'}$ and H$_{3'}$.

EXAMPLE 24

1-(2'-deoxy-2',2'-difluoro-3',5'-di-O-(triisopropylsilyl)-ribofuranosyl)-nicotinamide (27). 26 (420 mg, 0.75 mmol) and nicotinamide (732 mg, 6 mmol) were dissolved in 20 mL of CH$_3$CN/CH$_2$Cl$_2$ (1:1). To this solution was added TMSOTf (167 mg, 0.75 mmol) under argon, the reaction mixture was kept refluxing overnight. Solvent was evaporated in vacuo, concentrated crude product was examined by NMR and used for the next step without further purification.

EXAMPLE 25

1-(2'-deoxy-2',2'-difluoro-ribofuranosyl)-nicotinamide (28). Compound 28 was obtained according to the deprotection procedure to synthesize 22, using 27 (440 mg, 0.75 mmol) as the starting material. Crude product was purified by HPLC on a Waters RP-18 XBridge PrepShield 19×50 mm column (solvent was 20 mM ammonium acetate, compounds were eluted at a flow rate of 2 mL/min) to afford 28 (β-isomer, t$_R$=17.8 min, 78 mg, 0.28 mmol, 38%) and the α-isomer (t$_R$=14.8 min, 103 mg, 0.37 mmol, 50%). β-isomer: $^1$H NMR (D$_2$O, 600 MHz), δ ppm: 3.83 (d, J=11.4 Hz, 1H), 4.01 (d, J=12.6 Hz, 1H), 4.24 (d, J=7.8 Hz, 1H), 4.46 (dd, J=10.8, 20.4 Hz, 1H), 6.56 (d, J=8.4 Hz, 1H), 8.20 (t, J=6.6 Hz, 1H), 8.92 (d, J=7.8 Hz, 1H), 9.20 (d, J=6.6 Hz, 1H), 9.61 (s, 1H). $^{13}$C NMR (125 MHz, D$_2$O), δ ppm: 58.4, 67.3, 67.5, 67.6, 83.2, 83.3, 93.3, 93.4, 93.5, 93.6, 119.4, 121.7, 124.0, 128.6, 134.3, 141.4, 143.6, 146.9, 165.4. HRMS (ESI): calcd. for C$_{11}$H$_{12}$F$_2$N$_2$O$_4$: 274.0765. Found: 274.0771. α-isomer: $^1$H NMR (D$_2$O, 500 MHz), δ ppm: 3.78 (dd, J=4.5, 11.0 Hz, 1H), 3.91 (dd, J=1.5, 11 Hz, 1H), 4.59 (m, 1H), 6.75 (t, J=5.0 Hz, 1H), 8.24, (dd, J=5.0, 6.5 Hz, 1H), 8.98 (d, J=6.5 Hz, 1H), 9.11 (d, J=4.5 Hz, 1H), 9.34 (s, 1H).

EXAMPLE 26

2'-deoxy-2',2'-difluoro-ribo-nicotinamide mononucleotide (29). To a flame-dried round-bottom flask were added 28 (5 mg, 0.018 mmol), 6-methylnicotinamide (12.4 mg, 0.091 mmol) and 0.5 mL of trimethyl phosphate. At 0° C., 13.9 mg (0.091 mmol) of phosphorous oxychloride was added to the reaction mixture. This solution was stirred at 0° C. for another 2 hours. Ice was added to quenched the reaction, pH was adjusted to 7 by adding NaOH solution and phosphate buffer. Crude product was concentrated and purified by HPLC on a Waters RP-18 XBridge PrepShield 19×50 mm column (solvent was 20 mM ammonium acetate, compound was eluted at a flow rate of 2 mL/min) to afford 29 ($t_R$=6.2 min, 5 mg, 0.014 mmol, 78%). $^1$H NMR (D$_2$O, 500 MHz), δ ppm: 4.02 (dd, J=3.2, 13.4 Hz, 1H), 4.19 (dt, J=2.4, 13.4 Hz, 1H), 4.43 (d, J=8.4 Hz, 1H), 4.65 (stack, 2H), 6.75 (dd, J=2.3, 8.9 Hz, 1H), 8.38 (t, J=6.5 Hz, 1H), 9.10 (d, J=8.2 Hz, 1H), 9.36 (d, J=5.8 Hz, 1H), 9.78 (s, 1H). $^{13}$C NMR (125 MHz, D$_2$O), δ ppm: 59.7, 69.4, 69.5, 69.6, 69.8, 86.80, 86.84, 94.0, 94.2, 94.4, 94.5, 115.9, 118.4, 120.9, 123.4, 128.5, 134.1, 140.9, 143.2, 146.8, 165.4. HRMS (ESI): calcd. for $C_{11}H_{14}F_2N_2O_7P$: 355.0501. Found: 355.0503.

EXAMPLE 27

2'-deoxy-2',2'-difluoro-NAD$^+$ (30). A single reaction (50 μL) containing 6 mM of 29, 2 mM of ATP, 10 mM of MgCl$_2$, 1 μL of pyrophosphatase (1 unit), 5 μL of NMNAT-1 (13.5 μM) and 50 mM phosphate buffer (pH~7.4) was incubated at 37° C. for 1 hour. The reaction was terminated by addition of 3 μL of 10% TFA and purified by HPLC on a Waters RP-18 XBridge PrepShield 19×50 mm column (solvent was 20 mM ammonium acetate, compound was eluted at a flow rate of 2 mL/min, $t_R$=12.7 min, 90% versus ATP with recovery of unreacted 30). $^1$H NMR (500 MHz, D$_2$O), δ ppm: 4.28 (stack, 2H), 4.36 (m, 1H), 4.42 (s, 1H), 4.55 (stack, 3H), 4.73 (stack, 2H), 6.16 (d, J=5.6 Hz, 1H), 6.69 (d, J=9.3 Hz, 1H), 8.38 (dd, J=6.5, 7.9 Hz, 1H), 8.41 (s, 1H), 8.60 (s, 1H), 9.04 (d, J=8.2 Hz, 1H), 9.38 (d, J=6.3 Hz, 1H), 9.54 (s, 1H). $^{13}$C NMR (125 MHz, D$_2$O), δ ppm: 59.7, 65.18, 65.22, 69.3, 69.49, 69.55, 69.7, 70.3, 74.3, 83.9, 84.0, 86.76, 86.81, 94.0, 94.2, 94.3, 94.5, 118.4, 119.7, 121.8, 123.8, 128.4, 133.9, 140.2, 140.8, 143.1, 146.7, 148.9, 151.6, 154.7, 165.2. HRMS (ESI): calcd. for $C_{21}H_{26}F_2N_7O_{13}P_2$: 684.1026. Found: 684.1019.

EXAMPLE 28

2'-deoxy-2'-fluoro-arabino-nicotinamide mononucleotide (31). Compound 31 was obtained according to the phosphorylation procedure to synthesize 29, using 22 (7 mg, 0.027 mmol) as the starting material. Crude product was concentrated and purified by HPLC on a Waters RP-18 XBridge PrepShield 19×50 mm column (solvent was 20 mM ammonium acetate, compound was eluted at a flow rate of 2 mL/min) to afford 31 ($t_R$=5.4 min, 6 mg, 0.018 mmol, 67%). $^1$H NMR (D$_2$O, 400 MHz), δ ppm: 4.04 (m, 1H), 4.19 (m, 1H), 4.34 (m, 1H), 4.56 (dt, J=5.0, 17.8 Hz, 1H), 5.51 (dt, J=4.6, 51.4 Hz, 1H), 6.67 (dd, J=4.8, 8.8 Hz, 1H), 8.24 (t, J=7.1 Hz, 1H), 8.92 (d, J=7.9 Hz, 1H), 9.31 (d, J=6.1 Hz, 1H), 9.39 (s, 1H). $^{13}$C NMR (125 MHz, D$_2$O), δ ppm: 55.17, 55.20, 55.23, 60.60, 60.62, 72.6, 72.8, 90.17, 90.19, 98.5, 98.8, 99.2, 100.7, 128.3, 133.9, 140.3, 142.6, 145.8, 165.6. MS (M$^+$): calculated: 337.06. found: 337.45.

EXAMPLE 29

2'-deoxy-2'-fluoro-arabino-NAD$^+$ (32). A single reaction (50 μL) containing 6 mM of 31, 2 mM of ATP, 10 mM of MgCl$_2$, 1 μL of pyrophosphatase (1 unit), 5 μL of NMNAT-1 (13.5 μM) and 50 mM phosphate buffer (pH~7.4) was incubated at 37° C. for 1 hour. The reaction was terminated by addition of 3 μL of 10% TFA and purified by HPLC on a Waters RP-18 XBridge PrepShield 19×50 mm column (solvent was 20 mM ammonium acetate, compound was eluted at a flow rate of 2 mL/min, $t_R$=14.7 min, 95% versus ATP with recovery of unreacted 32). $^1$H NMR (D$_2$O, 600 MHz), δ ppm: 4.41 (m, 1H), 4.46 (stack, 2H), 4.57 (stack, 3H), 4.67 (dd, J=3.6, 5.4 Hz, 1H), 4.80 (dt, J=4.8, 17.4 Hz, 1H), 4.90 (t, J=6 Hz, 1H), 5.71 (dt, J=4.8, 51 Hz, 1H), 6.20 (d, J=6 Hz, 1H), 6.81, (dd, J=4.8, 9.6 Hz, 1H), 8.37, (s, 1H), 8.40 (dd, J=6.6, 7.8 Hz, 1H), 9.05, (d, J=7.8 Hz, 1H), 9.38 (d, J=6.6 Hz, 1H), 9.51 (s, 1H). $^{13}$C NMR (125 MHz, D$_2$O), δ ppm: 63.4, 65.4, 70.3, 70.8, 71.0, 74.1, 83.5, 83.8, 83.9, 86.8, 93.68, 93.73, 93.9, 95.3, 118.4, 128.3, 133.2, 140.0, 141.2, 143.4, 146.03, 148.9, 152.2, 165.1. MS (M$^+$): calculated: 666.11. found: 666.60.

EXAMPLE 30

2'-deoxy-2'-fluoro-ribo-nicotinamide mononucleotide (33). Compound 33 was obtained according to the phosphorylation procedure to synthesize 29, using 25 (3.5 mg, 0.014 mmol) as the starting material. Crude product was concentrated and purified by HPLC on a Waters RP-18 XBridge PrepShield 19×50 mm column (solvent was 20 mM ammonium acetate, compound was eluted at a flow rate of 2 mL/min) to afford 33 ($t_R$=5.9 min, 3.8 mg, 0.011 mmol, 83%). $^1$H NMR (D$_2$O, 600 MHz), δ ppm: 3.95 (d, J=12.6 Hz, 1H), 4.16 (d, J=13.2 Hz, 1H), 4.52 (stack, 2H), 5.40 (d, J=50.4 Hz, 1H), 6.67 (d, J=13.8 Hz, 1H), 8.31 (s, 1H), 9.00 (s, 1H), 9.35 (s, 1H), 9.74 (s, 1H). $^{13}$C NMR (150 MHz, D$_2$O), δ ppm: 55.16, 55.20, 60.1, 60.6, 69.3, 69.4, 86.97, 86.98, 90.0, 91.5, 94.6, 94.8, 127.8, 133.4, 141.0, 143.4, 145.9, 165.7. HRMS (ESI): calcd. for $C_{11}H_{15}FN_2O_7P$: 337.0595. Found: 337.0599.

EXAMPLE 31

2'-deoxy-2'-fluoro-ribo-NAD$^+$ (34). A single reaction (50 μl) containing 3.8 mM of 33, 10 mM of ATP, 10 mM of MgCl$_2$, 1 μL of pyrophosphatase (1 unit), 10 μL of NMNAT-1 (27 μM) and 50 mM phosphate buffer (pH~7.4) was incubated at 37° C. for 1 hour. The reaction was terminated by addition of 3 μL of 10% TFA and purified by HPLC on a Waters RP-18 XBridge PrepShield 19×50 mm column (solvent was 20 mM ammonium acetate, compound was eluted at a flow rate of 2 mL/min, $t_R$=18.6 min, 94% versus 33). $^1$H NMR (D$_2$O, 600 MHz), δ ppm: 3.44 (dd, J=7.2, 12 Hz, 1H), 3.54 (dd, J=4.2, 11.4 Hz, 1H), 4.10 (m, 1H), 4.15 (dd, J=4.8, 11.4 Hz, 2H), 4.27 (t, J=2.4 Hz, 1H), 4.37 (dd, J=1.8, 14.4 Hz, 1H), 4.40 (t, J=3.6 Hz, 1H), 4.49 (stack, 2H), 5.30, (dt, J=3.0, 51 Hz, 1H), 5.95, (d, J=6.0 Hz, 1H), 6.41 (dd, J=2.4, 13.8 Hz, 1H), 8.11, (s, 1H), 8.13 (dd, J=6.6, 7.8 Hz, 1H), 8.74 (d, J=8.4 Hz, 1H), 9.13 (d, J=6.6 Hz, 1H), 9.32 (s, 1H). $^{13}$C NMR (125 MHz, D$_2$O), δ ppm: 62.5, 63.45, 63.49, 65.36, 65.40, 67.7, 67.8, 70.4, 72.1, 73.9, 83.8, 83.9, 85.1, 85.2, 86.6, 94.1, 95.7, 97.2, 97.5, 102.4, 118.4, 128.7, 133.8, 139.2, 139.8, 140.3, 142.5, 145.99, 146.02, 149.0, 152.8, 155.4, 156.5, 165.0. HRMS (ESI): calcd. for $C_{21}H_{27}FN_7O_{13}P_2$: 666.1121. Found: 666.1132.

EXAMPLE 32

$^1$H and $^{13}$C NMR spectra for compounds referenced above $^1$H and $^{13}$C NMR spectra were obtained using either a 400 MHz, 500 MHz or a 600 MHz spectrometer. Melting points were uncorrected. 2-deoxy-1-methyl-3,5-di-O-(p-chlorobenzoyl)-D-ribofuranose was prepared by the method of Fox (Ref 47). Pyrophosphatase was purchased from New England Biolabs (MO296S). Yeast nicotinamide mononucleotide adenyltransferase was cloned from yeast genomic DNA and integrated into a pet28 bacterial expression vector and expressed in CodonPlus (Stratagene) cells. After induction with 1 mM IPTG for three hours, cells were pelleted and resuspended in 10 pellet volumes of 10 mM Tris buffer 500 mM NaCl pH 7.5 containing 10000 units of egg white lysozyme (Sigma, L6876) and broken by 3 freeze-thaw cycles. 50 units of DNase (Sigma, D4263) and $MgCl_2$ (final concentration 25 mM) were then added to destroy DNA and the lysate mixed until non-viscous. The lysate was pelleted again and the supernatant was incubated on nickel chelating resin (Gbiosciences 786-281) and purified by Ni-affinity chromatography using imidazole as an eluant. The purified protein was flash frozen in 20% glycerol and 2.5 mM DTT for later use. Results are provided in FIGS. 2-57.

EXAMPLE 33

Synthesis of Clofarabine

TIPS-protected 2-deoxy-ribonolactone 2 was obtained in 92% yield from 2-deoxy-ribonolactone (FIG. 9). 2 was treated with LiHMDS with the presence of NFSi at −78° C. to furnish only the arabino-isomer 3 in 72% isolated yield. Reduction of 3 with DIBAL-H provided lactol 4 in 91% yield. 4 was activated with methanesulfonylchloride and triethylamine, which formed only the α-chloro sugar 5 in quantitative yield. 5 was coupled with 2,6-dichloropurine by employing a previous reported method. This coupling gave a mixture of both the β and α isomers with a 3.5 to 1 ratio favoring the β-isomer. The mixture 6 was used in the next step without further purification. Amination of 6 with ammonia in isopropanol in a sealed tube at 105° C. afforded the desired 2-amino-6-chloropurine nucleoside 7, at this stage β-anomer was purified by column chromatography and the yield after coupling and amination steps is about 65%. Finally, deprotection of the silyl protecting groups gave clofarabine as an off-white solid, the NMR matches the reported data.

EXAMPLE 34

2-deoxy-3,5-di-O-(triisopropylsilyl)-D-ribonolactone (35). 2-Deoxy-D-ribonolactone (1.1 g, 8.3 mmol) was dissolved in 10 mL of anhydrous DMF, to this solution were added imidazole (3.4 g, 50 mmol) and triisopropylsilyl chloride (6.4 g, 33 mmol) were added. The resulting solution was stirred at room temperature for 24 h, and quenched by addition of water. Water layer was extracted by ethyl acetate (3×10 mL), organic layers were combined, washed with brine and dried over anhydrous $Na_2SO_4$. Crude product was concentrated in vacuo. Column chromatography (hexanes:ethyl acetate 25:1~20:1) provided 2 (3.4 g, 7.7 mmol, 92%) as colorless oil. $^1$H NMR ($CDCl_3$, 400 MHz), δ ppm: 1.05 (stack, 42H), 2.41 (dd, J=1.9, 17.6 Hz, 1H), 2.86 (dd, J=6.6, 17.6 Hz, 1H), 3.83 (dd, J=2.6, 9.4 Hz, 1H), 3.91 (dd, J=3.0, 11.4 Hz, 1H), 4.39 (s, 1H), 4.65 (d, J=6.5, 1H). $^{13}$C NMR (125 MHz, $CDCl_3$), δ ppm: 11.9, 12.1, 18.0, 39.7, 63.4, 70.1, 88.9, 176.1. HRMS (ESI): calcd. for $C_{23}H_{48}O_4Si_2$: 444.3091. Found: 444.3094.

EXAMPLE 35

2-deoxy-2-fluoro-3,5-di-O-(triisopropylsilyl)-D-ribonolactone (36). To a flame-dried 100 mL round-bottom flask were added 35 (2 g, 4.5 mmol) and NFSi (2.13 g, 6.77 mmol) in 40 mL of anhydrous THF. The solution was cooled to −78° C. and 5.9 mL (5.9 mmol) of a 1 M solution of LiHMDS in THF was added dropwise over a period of 10 mins. This was allowed to stir at −78° C. for an additional hour and was quenched by saturated $NH_4Cl$. The mixture was allowed to warm to room temperature, water layer was extracted by ethyl acetate (3×5 mL), organic layers were combined, washed with saturated $NaHCO_3$, water, brine, dried over anhydrous $Na_2SO_4$ and concentrated in vacuo. Column chromatography (hexanes:ethyl acetate 30:1) provided 36 (1.5 g, 3.25 mmol, 72%) as a white solid. mp=38–39° C. $^1$H NMR ($CDCl_3$, 400 MHz), δ ppm: 1.07 (stack, 42H), 3.91 (dd, J=2.4, 12.1 Hz, 1H), 4.08 (dt, J=2.1, 12.1 Hz, 1H), 4.16 (dt, J=2.1, 7.0 Hz, 1H), 4.92 (dt, J=7.2, 18.8 Hz, 1H), 5.10 (dd, J=7.4, 51.3 Hz, 1H). $^{13}$C NMR (100 MHz, $CDCl_3$), δ ppm: 11.9, 12.1, 17.7, 17.80, 17.84, 17.86, 60.3, 71.6, 71.8, 81.8, 81.9, 91.7, 93.7, 168.6, 168.8. HRMS (ESI): calcd. for $C_{23}H_{47}FO_4Si_2$: 462.2997. Found: 462.2993.

EXAMPLE 36

2-deoxy-2-fluoro-3,5-di-O-(triisopropylsilyl)-D-arabinofuranose (37). 36 (200 mg, 0.43 mmol) was dissolved in 1.5 mL of anhydrous toluene and cooled to −78° C. To this solution was added 3.02 mL of DIBAL-H in THF solution (3.02 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated $NaHCO_3$, water, brine, dried over anhydrous $Na_2SO_4$ and concentrated in vacuo. Column chromatography (hexanes:ethyl acetate 15:1) afforded 37 (181 mg, 0.39 mmol, 91%) as colorless oil. $^1$H NMR ($CDCl_3$, 400 MHz), δ ppm: 1.07 (stack, 54H), 3.46 (d, J=10.9 Hz, 1H), 3.60 (m, 1.27H), 3.78 (m, 1.57H), 3.95 (q, J=3.7 Hz, 0.28H), 4.32 (m, 1H), 4.49 (dd, J=0.9, 12.6 Hz, 1H), 4.63 (t, J=4.0 Hz, 0.14H), 4.67 (t, J=4.0 Hz, 0.14H), 4.81 (t, J=4.1 Hz, 0.28H), 4.83 (dd, J=0.8, 50.2 Hz, 1H), 5.31 (m, 0.3H), 5.35 (t, J=10.1 Hz, 1H). $^{13}$C NMR (125 MHz, $CDCl_3$), δ ppm: 12.0, 12.2, 18.0, 63.2, 75.4, 75.5, 75.6, 87.6, 87.7, 95.9, 97.5, 97.7, 98.8, 98.9, 100.8, 101.0. HRMS (ESI): calcd. for $C_{23}H_{49}FO_4Si_2$: 464.3153. Found: 464.3162.

EXAMPLE 37

1-chloro-2-deoxy-2-fluoro-3,5-di-O-(triisopropylsilyl)-D-arabinofuranose (38). 37 (40 mg, 0.086 mmol) was dissolved in 0.5 mL of $CH_2Cl_2$ and triethylamine (12.2 mg, 0.12 mmol). To this solution was added at 0° C. methanesulfonyl chloride (11.5 mg, 0.1 mmol). After 3 h of stirring under argon at room temperature, the mixture was evaporated in vacuo, and the residue was taken up in ethyl acetate. The solution was washed with saturated $NaHCO_3$, followed by 1 M HCl, water and brine. Solvent was concentrated under reduced pressure to afford 38 (40 mg, 0.086 mmol, almost quantitatively) as yellow liquid. $^1$H NMR ($CDCl_3$, 400 MHz), δ ppm: 1.08 (stack, 42H), 3.89 (dd, J=3.7, 11.7 Hz, 1H), 3.96 (dd, J=2.9, 11.7 Hz, 1H), 4.30 (dd, J=3.4, 8.3 Hz, 1H), 4.58 (dd, J=5.1, 14.8 Hz, 1H), 5.12 (d, J=51.7 Hz, 1H), 6.15 (d, J=12.5 Hz, 1H). $^{13}$C NMR (125 MHz, $CDCl_3$), δ ppm: 11.9, 12.0, 17.80, 17.84, 17.9, 61.4, 75.1, 75.4, 88.61, 88.64, 95.3, 95.6, 103.8, 105.3. HRMS (ESI): calcd. for $C_{23}H_{48}ClFO_3Si_2$: 482.2815. Found: 482.2822.

EXAMPLE 38

2,6-dichloro-9-(2'-deoxy-2'-fluoro-3',5'-di-O-(triisopropylsilyl)-D-arabinofuranosyl)-9H-purine (39). To a solution of 38 (36 mg, 0.075 mmol) in 1.1 mL of 1,2-dichloroethane were added 10 mg of 4 Å molecular sieves and 2,6-dichloropurine (21.5 mg, 0.113 mmol). The reaction mixture was refluxed at 100° C. overnight. Solvent was then removed in vacuo, the residue was redissolved in $CHCl_3$ and filtered, the filtrate was concentrated under reduced pressure. NMR of reaction mixture indicates the formation of both α and β isomers with a ratio of 1/3.5 (α/β). The crude product was used for the next step without further purification.

EXAMPLE 39

6-amino-2-chloro-9-(2'-deoxy-2'-fluoro-3',5'-di-O-(triisopropylsilyl)-β-D-arabinofuranosyl)-9H-purine (40). 38 (45 mg, 0.073 mmol) was dissolved in 3 mL of ammonia in isopropanol solution (2 M), the reaction was carried out in a sealed tube at 105° C. overnight. The reaction mixture was then cooled to room temperature and concentrated under reduced pressure. Column chromatography (hexanes:ethyl acetate 3:1~1:1) afforded 40 (30 mg, 0.049 mmol, 65%) as a colorless oil. $^1$H NMR ($CDCl_3$, 500 MHz), δ ppm: 1.09 (stack, 42H), 3.82 (m, 2H), 3.92 (q, J=4.5 Hz, 1H), 4.59 (dt, J=3.3, 18 Hz, 1H), 5.00 (dt, J=2.8, 52 Hz, 1H), 6.14 (s, broad, 2H), 6.41 (dd, J=3.8, 17.5 Hz, 1H), 8.03 (d, J=2.3 Hz, 1H).

EXAMPLE 40

6-amino-2-chloro-9-(2'-deoxy-2'-fluoro-β-D-arabinofuranosyl)-9H-purine (Clofarabine, 41). 40 (18.5 mg, 0.03 mmol) was dissolved in 1 mL of DMF, to this solution were added acetic acid (7.2 mg, 0.12 mmol) and tetramethylammonium fluoride (11 mg, 0.12 mmol). The reaction was allowed to stir at room temperature overnight. Solvent was removed in vacuo and column chromatography (ethyl acetate:methanol 20:1) afforded 41 (8.2 mg, 0.027 mmol, 90%) as a pale yellow foam. $^1$H NMR (DMSO, 500 MHz), δ ppm: 3.63 (m, 2H), 3.84 (q, J=4.9 Hz, 1H), 4.42 (dt, J=4.9, 19 Hz, 1H), 5.23 (dt, J=4.3, 53 Hz, 1H), 6.31 (dd, J=4.6, 13.7 Hz, 1H), 7.88 (s, broad, 2H), 8.27 (d, J=1.8 Hz, 1H).

EXAMPLE 45

2-deoxy-3,5-di-O-(triisopropylsilyl)-D-ribonolactone (35). 2-Deoxy-D-ribonolactone (1.1 g, 8.3 mmol) was dissolved in 10 mL of anhydrous DMF, to this solution were added imidazole (3.4 g, 50 mmol) and triisopropylsilyl chloride (6.4 g, 33 mmol) were added. The resulting solution was stirred at room temperature for 24 h, and quenched by addition of water. Water layer was extracted by ethyl acetate (3×10 mL), organic layers were combined, washed with brine and dried over anhydrous $Na_2SO_4$. Crude product was concentrated in vacuo. Column chromatography (hexanes:ethyl acetate 25:1~20:1) provided 35 (3.4 g, 7.7 mmol, 92%) as colorless oil. $^1$H NMR ($CDCl_3$, 400 MHz), δ ppm: 1.05 (stack, 42H), 2.41 (dd, J=1.9, 17.6 Hz, 1H), 2.86 (dd, J=6.6, 17.6 Hz, 1H), 3.83 (dd, J=2.6, 9.4 Hz, 1H), 3.91 (dd, J=3.0, 11.4 Hz, 1H), 4.39 (s, 1H), 4.65 (d, J=6.5 Hz, 1H). $^{13}$C NMR (125 MHz, $CDCl_3$), δ ppm: 11.9, 12.1, 18.0, 39.7, 63.4, 70.1, 88.9, 176.1. HRMS (ESI): calcd. for $C_{23}H_{48}O_4Si_2$: 444.3091. Found: 444.3094.

EXAMPLE 46

2-deoxy-2-fluoro-3,5-di-O-(triisopropylsilyl)-D-ribonolactone (36). To a flame-dried 100 mL round-bottom flask were added 35 (2 g, 4.5 mmol) and NFSi (2.13 g, 6.77 mmol) in 40 mL of anhydrous THF. The solution was cooled to −78° C. and 5.9 mL (5.9 mmol) of a 1 M solution of LiHMDS in THF was added dropwise over a period of 10 mins. This was allowed to stir at −78° C. for an additional hour and was quenched by saturated $NH_4Cl$. The mixture was allowed to warm to room temperature, water layer was extracted by ethyl acetate (3×5 mL), organic layers were combined, washed with saturated $NaHCO_3$, water, brine, dried over anhydrous $Na_2SO_4$ and concentrated in vacuo. Column chromatography (hexanes:ethyl acetate 30:1) provided 36 (1.5 g, 3.25 mmol, 72%) as a white solid. mp=38~39° C. $^1$H NMR ($CDCl_3$, 400 MHz), δ ppm: 1.07 (stack, 42H), 3.91 (dd, 2.4, 12.1 Hz, 1H), 4.08 (dt, J=2.1, 12.1 Hz, 1H), 4.16 (dt, J=2.1, 7.0 Hz, 1H), 4.92 (dt, 7.2, 18.8 Hz, 1H), 5.10 (dd, J=7.4, 51.3 Hz, 1H). $^{13}$C NMR (100 MHz, $CDCl_3$), δ ppm: 11.9, 12.1, 17.7, 17.80, 17.84, 17.86, 60.3, 71.6, 71.8, 81.8, 81.9, 91.7, 93.7, 168.6, 168.8. HRMS (ESI): calcd. for $C_{23}H_{47}FO_4Si_2$: 462.2997. Found: 462.2993.

EXAMPLE 47

2-deoxy-2,2-difluoro-3,5-di-O-(triisopropylsilyl)-D-ribonolactone (42). To a flame-dried 100 mL round-bottom flask were added 36 (92 mg, 0.2 mmol) and NFSi (95 mg, 0.3 mmol) in 2 mL of anhydrous THF. The solution was cooled to −78° C. and 0.26 mL (0.26 mmol) of a 1 M solution of LiHMDS in THF was added dropwise. This was allowed to stir at −78° C. for an additional hour and was quenched by saturated $NH_4Cl$. The mixture was allowed to warm to room temperature, water layer was extracted by ethyl acetate (3×5 mL), organic layers were combined, washed with saturated $NaHCO_3$, water, brine, dried over anhydrous $Na_2SO_4$ and concentrated in vacuo. Column chromatograph (hexanes:ethyl acetate 40:1) provided 42 (68 mg, 0.14 mmol, 71%) as pale yellow oil. $^1$H NMR ($CDCl_3$, 400 MHz), δ ppm: 1.08 (stack, 42H), 3.96 (dd, J=2.4, 12.0 Hz, 1H), 4.08 (dt, J=2.6, 12.1 Hz, 1H), 4.31 (m, 1H), 4.76 (dt, J=6.0, 11.2 Hz, 1H). $^{13}$C NMR (100 MHz, $CDCl_3$), δ ppm: 11.4, 11.45, 11.8, 12.1, 17.2, 17.3, 17.36, 17.43, 59.6, 68.3, 68.5, 68.6, 68.7, 82.5, 82.6, 109.9, 112.4, 115.0, 163.3, 163.6, 164.0. HRMS (ESI): calcd. for $C_{23}H_{46}F_2O_4Si_2$: 480.2903. Found: 480.2901.

EXAMPLE 48

1-deoxy-2,2-difluoro-3,5-di-O-(triisopropylsilyl)-D-ribofuranose (43). 42 (160 mg, 0.33 mmol) was dissolved in 1.5 mL of anhydrous toluene and cooled to −78° C. To this solution was added 2.32 mL of DIBAL-H in THF solution (2.32 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated $NaHCO_3$, water, brine, dried over anhydrous $Na_2SO_4$ and concentrated in vacuo. Column chromatography (hexanes:ethyl acetate 10:1) provided 43 (146 mg, 0.3 mmol, 91%) as colorless oil. $^1$H NMR ($CDCl_3$, 400 MHz), δ ppm: 1.04 (stack, 78H), 3.48 (d, J=11.3 Hz, 1H), 3.67 (m, 1.8H), 3.81 (m, 1.8H), 3.88 (dt, J=2.1, 11.2 Hz, 1H), 4.02 (m, 0.8H), 4.24 (m, 1H), 4.39 (dt, J=2.0, 10.7 Hz, 1H), 4.67 (m, 0.8H), 5.02 (dd, J=5.1, 9.8 Hz, 0.8H), 5.11 (dd, J=6.1, 11.3 Hz, 1H). $^{13}$C NMR (125 MHz, $CDCl_3$), δ ppm: 11.87, 11.90, 12.1, 12.3, 17.72, 17.73, 17.78, 17.83, 17.86, 17.89, 62.2, 62.34, 62.36, 69.6, 69.7, 69.8, 70.0, 71.9, 72.0, 72.1, 72.3, 83.95, 84.02, 85.3, 95.3, 95.5, 95.6, 95.8, 96.0, 96.2, 96.3, 96.5, 119.5, 120.1, 121.5, 121.6, 122.1, 123.6, 124.2. HRMS (ESI): calcd. for $C_{23}H_{48}F_2O_4Si_2$: 482.3059. Found: 482.3054.

EXAMPLE 49

1-methylsulfonyl-2-deoxy-2,2-difluoro-3,5-di-O-(triisopropylsilyl)-D-ribofuranose (44). 43 (146 mg, 0.3 mmol) was dissolved in 1.1 mL of $CH_2Cl_2$ and triethylamine (42 mg, 0.42 mmol). To this solution was added at 0° C. methanesulfonyl chloride (41 mg, 0.35 mmol). After 3 h of stirring under argon at room temperature, the mixture was evaporated in vacuo, and the residue was taken up in ethyl acetate. The solution was washed with saturated $NaHCO_3$, followed by 1 M HCl, water and brine. Solvent was concentrated under reduced pressure to afford 44 (165 mg, 0.3 mmol, almost quantitatively) as yellow liquid. $^1$H NMR ($CDCl_3$, 400 MHz), δ ppm: 1.07 (stack, 74H), 3.07 (s, 1.9H), 3.08 (s, 3H), 3.83 (dd, J=3.8, 11.4 Hz, 0.64H), 3.89 (m, 2H), 4.00 (m, 1.6H), 4.26 (dd, J=4.0, 8.1 Hz, 1H), 4.47 (dd, J=4.7, 16.5 Hz, 1H), 4.59 (m, 0.64H), 5.83 (d, J=7.0 Hz, 0.64H), 5.92 (d, J=6.8 Hz, 1H). $^{13}$C NMR (125 MHz, $CDCl_3$), δ ppm: 11.84, 11.85, 12.1, 12.2, 17.67, 17.73, 17.76, 17.79, 17.81, 17.87, 17.91, 40.0, 40.2, 46.3, 61.5, 61.8, 69.0, 69.2, 69.4, 70.98, 71.12, 71.2, 71.4, 84.7, 84.8, 88.0, 99.4, 99.6, 99.9, 100.1, 100.3, 100.5. HRMS (ESI): calcd. for $C_{24}H_{50}F_2O_6SSi_2$: 560.2835. Found: 560.284.

EXAMPLE 50

2'-deoxy-2',2'-difluoro-3',5'-di-O-(triisopropylsilyl)cytidine (45). Freshly prepared bis(trimethylsilyl)cytosine (75 mg, 0.03 mmol) was dissolved in 1 mL of 1,2-dichloroethane, to this solution was added TMSOTf (6.7 mg, 0.03 mmol). The mixture was stirred at room temperature for 30 mins before 44 (10 mg, 0.018 mmol) was added, and the reaction was refluxed overnight. The reaction mixture was cooled to room temperature and solvent was removed under reduced pressure. NMR spectrum of reaction mixture indicates the formation of both α and β isomers with a ratio of 1/1. The crude product 45 was used for the next step without further purification.

EXAMPLE 51

2'-deoxy-2',2'-difluorocytidine (Gemcitabine, 46). To a solution of 45 (10 mg, 0.017 mmol) in 1 mL of DMF were added acetic acid (5.2 mg, 0.087 mmol) and tetramethylammonnium fluoride (8 mg, 0.087 mmol). The reaction was stirred at room temperature overnight, then was concentrated and purified by HPLC (solvent was 20 mM ammonium acetate, compounds were eluted at a flow rate of 2 mL/min) to afford 46 (β-isomer, $t_R$=16.4 min, 1.7 mg, 0.006 mmol, 36%) and α-isomer ($t_R$=13.2 min, 1.9 mg, 0.007 mmol, 42%). $^1$H NMR ($D_2O$, 500 MHz), δ ppm: 3.86 (dd, J=5.0, 12.9 Hz, 1H), 4.01 (dd, J=1.6, 12.9 Hz, 1H), 4.13 (m, 1H), 4.40 (m, 1H), 6.25 (t, J=8.8 Hz, 1H), 6.30 (d, J=8.0 Hz, 1H), 8.03 (d, J=8.0 Hz, 1H).

EXAMPLE 52

Effects of 2'-Deoxy-2'-fluoro-nucleosides and Nucleotides on Enzyme Activity

SirT1 Activity Assay:

Reactions containing 200 μM $NAD^+$, 100 μM JB12 peptide, and 100 mM phosphate buffer at pH 7.5, with varying concentrations of 2'-deoxy-2'-fluoro-nucleosides or nucleotides were initiated by addition of SirT1 enzyme to a concentration of 12.9 μM. Reactions were incubated for 30 mins at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

SirT2 Activity Assay:

Reactions containing 800 μM $NAD^+$, 500 μM H3 peptide, and 100 mM phosphate buffer at pH 7.5, with varying concentrations of 2'-deoxy-2'-fluoro-nucleosides or nucleotides were initiated by addition of SirT2 enzyme to a concentration of 16.6 μM. Reactions were incubated for 45 mins at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

SirT3 Activity Assay:

Reactions containing 800 μM $NAD^+$, 500 μM H3 peptide, and 100 mM phosphate buffer at pH 7.5, with varying concentrations of 2'-deoxy-2'-fluoro-nucleosides or nucleotides were initiated by addition of SirT3 enzyme to a concentration of 13.9 μM. Reactions were incubated for 2 hours at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

CD38 Activity Assay:

CD38 (500 nM) in 100 mM phosphate buffer at pH 7.5 was incubated with various concentrations of 2'-deoxy-2'-fluoro-nucleosides and nucleotides for 30 mins at room temperature. 35 μL of the enzyme inhibitor solution was added to a cuvette containing 1 mL of 100 mM phosphate buffer at pH 7.5, containing 200 μM $NGD^+$. Reaction progress upon initiation by enzyme addition was monitored by 295 nm absorbance.

TABLE 2

Figure 16:
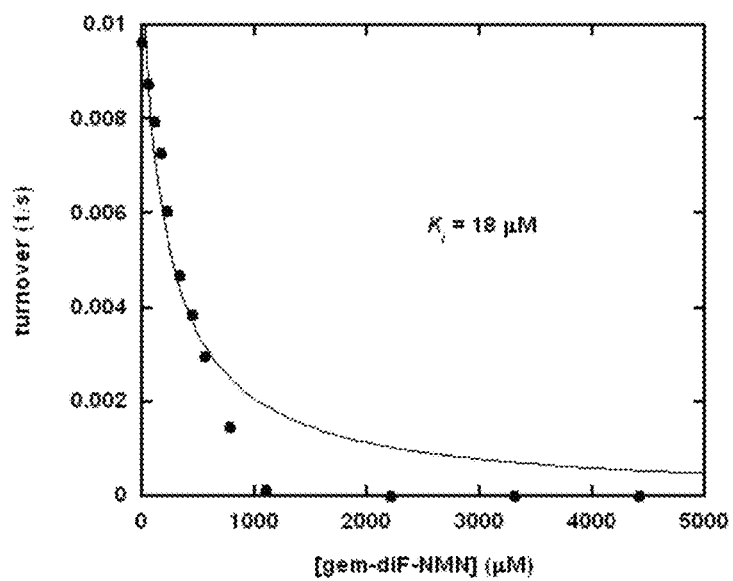
FIG. 16 illustrates inhibition of SirT1 activity by gem-diF-NMM.

Summary of results in tabular form - see FIGS. 16, 20, and 21 for further results and results in graphical form

| Structure | Name | SirT1 | SirT2 | SirT3 | CD38 |
|---|---|---|---|---|---|
| 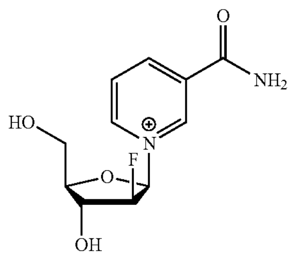 | ara-F-NR | $K_i$ = high mM | $K_i$ = 2.3 mM | $K_i$ = 623 µM | |
| 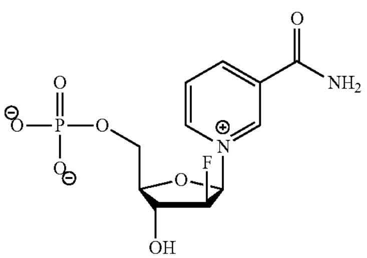 | ara-F-NMN | | no inhibition | | |
| 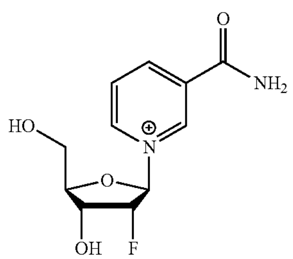 | ribo-F-NR | $K_i$ = 200 µM | $K_i$ = 1.73 mM | $K_i$ = 250 µM | |
| 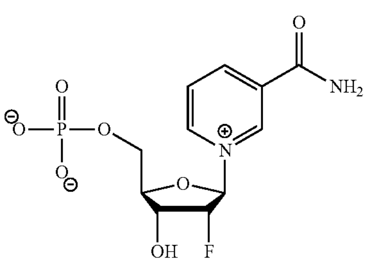 | ribo-F-NMN | no inhibition | $K_i$ = 450 µM | $K_i$ = 106 µM | |
| 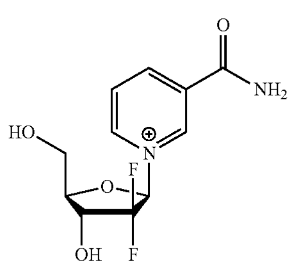 | gem-diF-NR | no inhibition | $K_i$ = high mM | $K_i$ = high mM | |
| 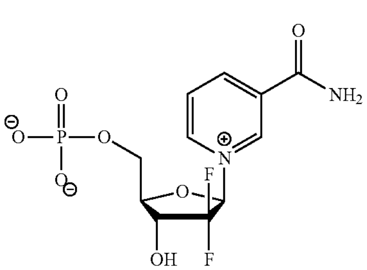 | gem-diF-NMN | $K_i$ = 18 µM | $K_i$ = 162 µM | $K_i$ = 128 µM | inhibited at 300 µM |

TABLE 2-continued

Summary of results in tabular form - see FIGS. 16, 20, and 21 for further results and results in graphical form

| Structure | Name | SirT1 | SirT2 | SirT3 | CD38 |
|---|---|---|---|---|---|
| 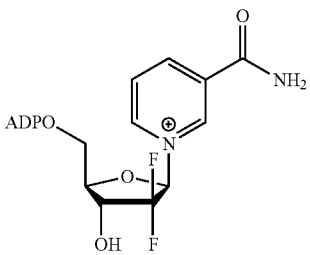 | gem-diF-NAD | $K_i = 60$ μM | | | |

The dose-response and kinetics gem-diF-NMN and gem-diF-NAD inhibition of SirT1 was explored in further detail following the protocol described above. Results are shown in FIG. 17 and FIG. 18.

EXAMPLE 53

Toxicity of 2'-Deoxy-2'-fluoro-nucleosides and Nucleotides on HEK293 Cells

Toxicity to HEK293 Cells:

1. HEK293 cells were seeded in 96-well plate at a density of 25,000 cells/well the day before the experiment starts;
2. After the cells reach 50~60% confluency, media was taken out, and 100 μL of fresh media was added to each well;
3. F-derivatives were plated at 100 and 500 μM (in duplicates) concentrations;
4. After 12 hours' incubation at 37° C., the media was taken out, 100 μL of fresh media was added to each well along with 20 μL of 5 mg/mL of MTT solution (in PBS);
5. After 1.5 hours' incubation at 37° C., media was taken out and 100 μL of DMSO was added to each well, the plate was mixed on shaker for 5 mins;

Absorbance was measured at 570 nm.

TABLE 3

Toxicity of 2'-Deoxy-2'-fluoro-nucleosides and nucleotides on HEK293 cells: Results in tabular form (see FIG. 18 for results in graphical form)

| | 100 μM absorbance | 500 μM absorbance | 100 μM relative viability | 500 μM relative viability |
|---|---|---|---|---|
| ara-F-NR | 1.5325 | 1.25 | 0.674145 | 0.549874 |
| ara-F-NMN | 1.267 | 0 | 0.557352 | 0 |
| ara-F-NAD | 1.52275 | 1.30225 | 0.669856 | 0.572858 |
| ribo-F-NR | 0.019 | 0.0015 | 0.008358 | 0.00066 |
| ribo-F-NMN | 1.2275 | 0.9845 | 0.539976 | 0.43308 |
| ribo-F-NAD | 1.4985 | 1.38375 | 0.659188 | 0.60871 |
| gem-diF-NR | 1.679 | 1.42975 | 0.73859 | 0.628945 |
| gem-diF-NMN | 1.559 | 0 | 0.685802 | 0 |
| gem-diF-NAD | 1.797 | 1.55575 | 0.790498 | 0.684373 |
| control | 2.27325 | 2.27325 | 1 | 1 |

EXAMPLE 54

Toxicity of 2'-Deoxy-2'-fluoro-nucleosides and Nucleotides to Neuro2A Cells

6. Neuro2A cells were seeded in 96-well plate at a density of 25,000 cells/well the day before the experiment starts;
7. After the cells reach 50~60% confluency, media was taken out, and 100 μL of fresh media was added to each well;
8. F-derivatives were plated at 100 and 500 μM (in duplicates) concentrations;
9. After 12 hours' incubation at 37° C., the media was taken out, 100 μL of fresh media was added to each well along with 20 μL of 5 mg/mL of MTT solution (in PBS);
10. After 1.5 hours' incubation at 37° C., media was taken out and 100 μL of DMSO was added to each well, the plate was mixed on shaker for 5 mins;

Absorbance was measured at 570 nm.

TABLE 4

Toxicity of 2'-Deoxy-2'-fluoro-nucleosides and nucleotides on Neuro2A cells: Results in graphical form (see FIG. 19 for results in graphical form)

| | 100 μM absorbance | 500 μM absorbance | 100 μM relative viability | 500 μM relative viability |
|---|---|---|---|---|
| ara-F-NR | 2.0227 | 2.0666 | 0.831 | 0.849 |
| ara-F-NMN | 2.126 | 0.0143 | 0.874 | 0.006 |
| ara-F-NAD | 2.2482 | 1.7012 | 0.924 | 0.699 |
| ribo-F-NR | 1.8769 | 0.8391 | 0.771 | 0.345 |
| ribo-F-NMN | 2.2023 | 1.7872 | 0.905 | 0.735 |
| ribo-F-NAD | 1.6122 | 0.6455 | 0.663 | 0.265 |
| gem-diF-NR | 0.8234 | 0.5374 | 0.338 | 0.221 |
| gem-diF-NMN | 1.0774 | 0.0217 | 0.443 | 0.009 |
| gem-diF-NAD | 1.5765 | 1.1916 | 0.648 | 0.49 |
| control | 2.433 | 2.433 | 1 | 1 |

EXAMPLE 55

Combined Results: Toxicity of 2'-deoxy-2'-fluoro-nucleosides and Nucleotides

TABLE 5

Combined results: Toxicity of 2'-deoxy-2'-fluoro-nucleosides and nucleotides

| Structure | Name | EC$_{50}$ (µM) HEK293 | EC$_{50}$ (µM) Neuro2A |
|---|---|---|---|
| 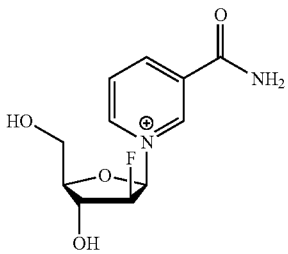 | ara-F-NR | 550 | 3840 |
| 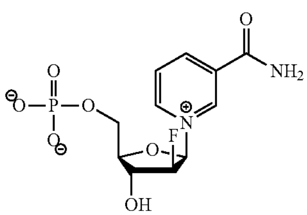 | ara-F-NMN | 88 | 164 |
| 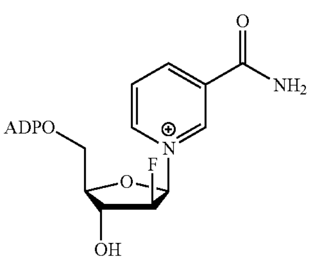 | ara-F-NAD | 1000 | 1500 |
| 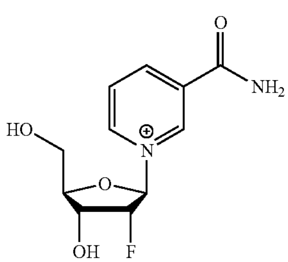 | ribo-F-NR | 17 | 281 |
| 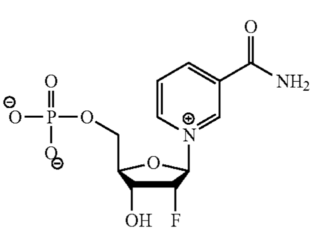 | ribo-F-NMN | 241 | 1400 |
| 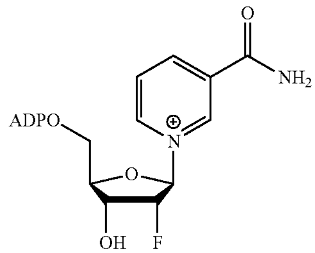 | ribo-F-NAD | 1020 | 350 |
| 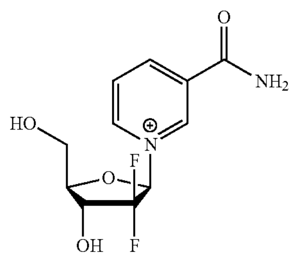 | gem-diF-NR | 846 | 61 |
| 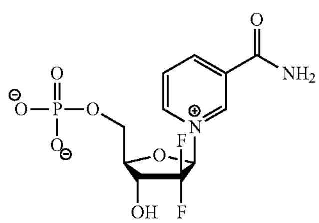 | gem-diF-NMN | 118 | 64 |
| 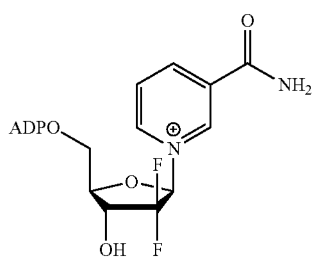 | gem-diF-NAD | 1130 | 400 |

EXAMPLE 56

Ribo-F-NR Dose Response in HEK293 Cells

Assay:

1. HEK293 cells were seeded in 96-well plate at a density of 10,000 cells/well the day before the experiment starts;
2. After the cells reach 50~60% confluency, media was taken out, and 100 µL of fresh media was added to each well;
3. Ribo-F-NR (stock concentration=5.53 mM) were plated at 11, 22, 27, 44, 55, 83 and 111 µM (in triplicates) concentrations;
4. After 12 hours' incubation at 37° C., the media was taken out, 100 µL of fresh media was added to each well along with 20 µL of 5 mg/mL of MTT solution (in PBS);

5. After 1.5 hours' incubation at 37° C., media was taken out and 100 µL of DMSO was added to each well, the plate was mixed on shaker for 5 mins;

6. Absorbance was measured at 570 nm.

TABLE 6

Ribo-F-NR Dose Response in HEK293 cells in tabular form (see FIG. 20 for results in graphical form)

| [ribo-F-NR] (µM) | absorbance | relative viability |
|---|---|---|
| 0 | 0.129 | 1 |
| 11 µM | 0.104067 | 0.806718 |
| 22 µM | 0.084111 | 0.652024 |
| 27 µM | 0.062 | 0.48062 |
| 44 µM | 0.03275 | 0.253876 |
| 55.3 µM | 0.015 | 0.116279 |
| 83 µM | 0.006 | 0.046512 |
| 111 µM | 0.001078 | 0.008358 |

EXAMPLE 57

2-deoxy-2-chloro-3,5-di-O-(t-butyldimethylsilyl)-D-ribonolactone (48). To a solution of 47 (100 mg, 0.28 mmol) and triethylamine (170 mg, 1.68 mmol) in 2 mL of anhydrous $CH_2Cl_2$ was added TMSOTf (187 mg, 0.84 mmo) at 0° C. The mixture was allowed to stir at 0° C. for another 30 mins before a solution of NCS (56 mg, 0.42 mmol) in 2 mL of $CH_2Cl_2$ was added. After stirring at 0° C. for another 1 h, the reaction was quenched with addition of saturated $NH_4Cl$ solution, aqueous phase was extracted with $CH_2Cl_2$ (3×5 mL). Combined organic layer was washed with brine, dried over anhydrous $Na_2SO_4$ and concentrated in vacuo. Flash chromatography (hexanes:ethyl acetate 25:1) afforded 2 (44 mg, 0.11 mmol, 40%) as colorless oil. $^1$H NMR ($CDCl_3$, 500 MHz), δ ppm: 0.05 (s, 3H), 0.06 (s, 3H), 0.12 (s, 3H), 0.16 (s, 3H), 0.87 (s, 9H), 0.88 (s, 9H), 3.76 (dd, J=2.7, 12.3 Hz, 1H), 3.94 (dd, J=2.4, 12.3 Hz, 1H), 4.15 (m, 1H), 4.38 (d, J=7.9 Hz, 1H), 4.58 (t, J=7.4 Hz, 1H). $^{13}$C NMR (125 MHz, $CDCl_3$), δ ppm: −5.5, −5.4, −5.1, −4.3, 17.8, 18.2, 25.5, 25.7, 59.0, 59.7, 74.9, 83.7, 169.5.

2-deoxy-2-chloro-3,5-di-O-(t-butyldimethylsilyl)-D-arabino-furanose (49). 48 (48 mg, 0.122 mmol) was dissolved in 1 mL of anhydrous toluene and cooled to −78° C. To this solution was added 0.85 mL of DIBAL-H in THF solution (0.85 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated $NaHCO_3$, water, brine, dried over anhydrous $Na_2SO_4$ and concentrated in vacuo. Column chromatography (hexanes:ethyl acetate 20:1) afforded 49 (45 mg, 0.113 mmol, 94%) as colorless oil. $^1$H NMR ($CDCl_3$, 500 MHz), δ ppm: 0.05 (s, 6.3H), 0.12 (s, 4.1H), 0.14 (s, 3.6H), 0.87 (s, 2.9H), 0.88 (s, 9H), 0.90 (s, 9H), 0.92 (s, 1.6H), 3.62 (dd, J=1.7, 9.7 Hz, 1H), 3.66 (dd, J=2.5, 11.1 Hz, 0.2H), 3.75 (m, 2.3H), 3.83 (d, J=10.4 Hz, 0.15H), 3.93 (m, 0.15H), 3.98 (s, 1H), 4.01 (dd, J=4.1, 6.7 Hz, 0.16H), 4.17 (m, 1H), 4.33 (t, J=2.5 Hz, 1H), 4.41 (dd, J=5.1, 6.5 Hz, 0.13H), 5.22 (dd, J=4.1, 10.3 Hz, 0.14H), 5.33 (d, J=9.7 Hz, 1H). $^{13}$C NMR (125 MHz, $CDCl_3$), δ ppm: −5.6, −5.5, −5.4, −4.9, −4.84, −4.78, −4.2, 17.80, 17.84, 18.32, 18.39, 25.6, 25.8, 25.9, 62.6, 63.3, 64.6, 65.8, 78.7, 84.9, 86.9, 96.7, 103.5.

1-chloro-2-deoxy-2-chloro-3,5-di-O-(t-butyldimethylsilyl)-D-arabinofuranose (50). 49 (45 mg, 0.113 mmol) was dissolved in 2 mL of $CH_2Cl_2$ and triethylamine (16 mg, 0.157 mmol). To this solution was added at 0° C. methanesulfonyl chloride (15 mg, 0.128 mmol). After 3 h of stirring under argon at room temperature, the mixture was evaporated in vacuo, and the residue was taken up in ethyl acetate. The solution was washed with saturated $NaHCO_3$, followed by 1 M HCl, water and brine. Solvent was concentrated under reduced pressure to afford 50 (46 mg, 0.111 mmol, almost quantitatively) as yellow liquid. $^1$H NMR ($CDCl_3$, 500 MHz), δ ppm: 0.10 (stack, 12H), 0.85 (stack, 18H), 3.78 (dd, J=4.2, 11.8 Hz, 1H), 3.84 (dd, J=3.5, 11.8 Hz, 1H), 4.26 (m, 1H), 4.35 (m, 1H), 4.39 (dd, J=2.4, 5.4 Hz, 1H), 6.11 (s, 1H).

1-(2'-deoxy-2'-chloro-3',5'-di-O-(t-butyldimethylsilyl) arabinofuranosyl)-nicotinamide (51). 50 (50 mg, 0.12 mmol) and nicotinamide (36 mg, 0.30 mmol) were dissolved in 1.5 mL of $CH_2Cl_2$. To this solution at 0° C. was added a ice-cold solution of nicotinamide (36 mg, 0.30 mmol) and $AgSbF_6$ (83 mg, 0.24 mmol) in 1.5 mL of acetonitrile. Reaction mixture was kept at room temperature overnight. Solvent was evaporated under reduce pressure and the residue was redissolved in methanol and pass through a short pad of celite. Concentrated crude product was examined by NMR and used for the next step without further purification.

1-(2'-deoxy-2'-chloro-arabinofuranosyl)-nicotinamide (52). To a solution of 51 (60 mg, 0.12 mmol) in 1.5 mL of DMF were added acetic acid (36 mg, 0.6 mmol) and tetramethylammonnium fluoride (56 mg, 0.6 mmol). The reaction was stirred at room temperature overnight, then was concentrated and purified by HPLC (solvent was 20 mM ammonium acetate, compounds were eluted at a flow rate of 2 mL/min) to afford 52 (β-isomer, $t_R$=7.6 min, 22 mg, 0.081 mmol, 68%) and α-isomer ($t_R$=8.1 min, 4.9 mg, 0.018 mmol, 15%). β-isomer $^1$H NMR ($D_2O$, 500 MHz), δ ppm: 3.93 (dd, J=5.7, 12.8 Hz, 1H), 4.02 (dd, J=3.4, 12.8 Hz, 1H), 4.58 (t, J=5.9 Hz, 1H), 4.70 (m, 1H), 4.76 (dd, J=3.8, 8.5 Hz, 1H), 6.67 (d, J=4.5 Hz, 1H), 8.32 (dd, J=6.5, 7.9 Hz, 1H), 9.03 (d, J=8.1 Hz, 1H), 9.28 (d, J=6.4 Hz, 1H), 9.52 (s, 1H).

2-deoxy-2-chloro-3,5-di-O-(t-butyldimethylsilyl)-D-ribonolactone (54). To a flame-dried 50 mL round-bottom flask were added 53 (25 mg, 0.058 mmol) and NCS (12 mg, 0.087 mmol) in 1 mL of anhydrous THF. The solution was cooled to −78° C. and 75 µL (0.075 mmol) of a 1 M solution of NaHMDS in THF was added dropwise over a period of 10 mins. This was allowed to stir at −78° C. for an additional hour and was quenched by saturated $NH_4Cl$. The mixture was allowed to warm to room temperature, water layer was extracted by ethyl acetate (3×10 mL), organic layers were combined, washed with saturated $NaHCO_3$, water, brine, dried over anhydrous $Na_2SO_4$ and concentrated in vacuo. Crude product was purified by flash chromatography (hexanes:ethyl acetate 35:1) to afford both 54 (6.5 g, 0.0165 mmol, 28%) and 48 (11.5 mg, 0.029 mmol, 50%) as colorless oil. 54 $^1$H NMR ($CDCl_3$, 500 MHz), δ ppm: 0.05 (s, 3H), 0.06 (s, 3H), 0.11 (s, 3H), 0.13 (s, 3H), 0.87 (s, 9H), 0.89 (s, 9H), 3.78 (dd, J=1.9, 12.1 Hz, 1H), 3.90 (dd, J=2.7, 12.1 Hz, 1H), 4.36, (m, 1H), 4.47 (dd, J=2.7, 5.5 Hz, 1H), 4.57 (d, J=5.5 Hz, 1H). $^{13}$C NMR (125 MHz, $CDCl_3$), δ ppm: −5.6, −5.5, −5.1, −4.9, 18.2, 18.3, 25.6, 25.8, 55.7, 61.4, 70.4, 85.8, 171.2.

2-deoxy-2-chloro-3,5-di-O-(t-butyldimethylsilyl)-D-ribofuranose (55). 54 (50 mg, 0.127 mmol) was dissolved in 1 mL of anhydrous toluene and cooled to −78° C. To this solution was added 0.9 mL of DIBAL-H in THF solution (0.90 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated NaHCO$_3$, water, brine, dried over anhydrous Na$_2$SO$_4$ and concentrated in vacuo. Column chromatography (hexanes:ethyl acetate 15:1) afforded 55 (46 mg, 0.117 mmol, 92%) as colorless oil. $^1$H NMR (CDCl$_3$, 500 MHz), δ ppm: 0.04 (stack, 7H), 0.06 (s, 8H), 0.10 (s, 22H), 0.12 (s, 3H), 0.15 (3H), 0.87 (s, 9H), 0.90 (stack, 58H), 3.50 (d, J=7.4 Hz, 2.5H), 3.54 (dd, J=5.1, 11.2 Hz, 1H), 3.63 (dd, J=1.1, 11.1 Hz, 2.5H), 3.66 (dd, J=3, 11.2 Hz, 1H), 3.80 (dd, J=2.3, 11.1 Hz, 2.5H), 4.04 (stack, 5.5H), 4.15 (t, J=4.3 Hz, 1H), 4.19 (m, 1H), 4.26 (d, J=4.2 Hz, 1H), 4.68 (dd, J=5.3, 6.4 Hz, 2.5H), 5.23 (dd, J=4.1, 12.4 Hz, 1H), 5.26 (d, J=7.4 Hz, 2.5H). $^{13}$C NMR (125 MHz, CDCl$_3$), δ ppm: −5.6, −5.5, −5.4, −5.03, −4.96, −4.93, −4.8, 18.1, 18.3, 25.7, 25.8, 25.9, 59.3, 61.1, 63.0, 65.4, 69.8, 73.9, 83.4, 85.8, 98.1, 102.3.

1-chloro-2-deoxy-2-chloro-3,5-di-O-(t-butyldimethylsilyl)-D-ribofuranose (56). 55 (50 mg, 0.126 mmol) was dissolved in 2 mL of CH$_2$Cl$_2$ and triethylamine (18 mg, 0.178 mmol). To this solution was added at 0° C. methanesulfonyl chloride (16.5 mg, 0.143 mmol). After 3 h of stirring under argon at room temperature, the mixture was evaporated in vacuo, and the residue was taken up in ethyl acetate. The solution was washed with saturated NaHCO$_3$, followed by 1 M HCl, water and brine. Solvent was concentrated under reduced pressure to afford 56 (52 mg, 0.125 mmol, almost quantitatively) as yellow liquid. $^1$H NMR (CDCl$_3$, 500 MHz), δ ppm: 0.05 (stack, 48H), 0.89 (stack, 72H), 3.71 (stack, 4H), 3.86 (dd, J=2.3, 12 Hz, 2H), 4.09 (m, 2H), 4.22 (dd, J=4.5 Hz, 1H), 4.25 (dd, J=2.1, 5.9 Hz, 1H), 4.39 (m, 1H), 4.90 (dd, J=4.6, 8.0 Hz, 2H), 6.11 (s, 2H), 6.20 (d, J=4.5 Hz, 1H). $^{13}$C NMR (125 MHz, CDCl$_3$), δ ppm: −5.6, −5.5, −5.4, −5.3, −5.0, −4.9, −4.8, −4.7, 18.0, 18.3, 18.4, 25.61, 25.62, 25.8, 25.9, 60.9, 61.2, 62.2, 67.6, 69.0, 70.8, 85.5, 89.4, 96.2, 97.2.

1-(2'-deoxy-2'-chloro-3',5'-di-O-(t-butyldimethylsilyl)-D-ribofuranosyl)-nicotinamide (57). 56 (17 mg, 0.041 mmol) and nicotinamide (12 mg, 0.098 mmol) were dissolved in 1.5 mL of CH$_2$Cl$_2$. To this solution at 0° C. was added a ice-cold solution of nicotinamide (13 mg, 0.107 mmol) and AgSbF$_6$ (28 mg, 0.082 mmol) in 1.5 mL of acetonitrile. Reaction mixture was kept at room temperature overnight. Solvent was evaporated under reduce pressure and the residue was redissolved in methanol and pass through a short pad of celite. Concentrated crude product was examined by NMR and used for the next step without further purification.

1-(2-deoxy-2-chloro-D-ribofuranosyl)-nicotinamide (58). To a solution of 57 (21 mg, 0.042 mmol) in 1.5 mL of DMF were added acetic acid (12.6 mg, 0.21 mmol) and tetramethylammonnium fluoride (19.5 mg, 0.21 mmol). The reaction was stirred at room temperature overnight, then was concentrated and purified by HPLC (solvent was 20 mM ammonium acetate, compounds were eluted at a flow rate of 2 mL/min) to afford 58 (β-isomer, t$_R$=5.9 min, 5.1 mg, 0.019 mmol, 45%) and α-isomer (t$_R$=7.6 min, 3 mg, 0.011 mmol, 28%). β-isomer $^1$H NMR (D$_2$O, 500 MHz), δ ppm: 3.85 (dd, J=2.3, 13.0 Hz, 1H), 4.02 (d, J=11.1 Hz, 1H), 4.47 (m, 1H), 4.50 (m, 1H), 4.78 (m 1H), 6.45 (d, J=4.5 Hz, 1H), 8.19 (t, J=7.2 Hz, 1H), 8.91 (d, J=8.0 Hz, 1H), 9.27 (d, J=6.1 Hz, 1H), 9.65 (s, 1H).

2-deoxy-2,2-dichloro-3,5-di-O-(t-butyldimethylsilyl)-D-ribonolactone (59). To a flame-dried 50 mL round-bottom flask were added 47 (100 mg, 0.278 mmol) and NCS (75 mg, 0.56 mmol) in 2 mL of anhydrous THF. The solution was cooled to −78° C. and 0.56 mL (0.56 mmol) of a 1 M solution of LiHMDS in THF was added dropwise over a period of 10 mins. This was allowed to stir at −78° C. for an additional hour and was quenched by saturated NH$_4$Cl. The mixture was allowed to warm to room temperature, water layer was extracted by ethyl acetate (3×10 mL), organic layers were combined, washed with saturated NaHCO$_3$, water, brine, dried over anhydrous Na$_2$SO$_4$ and concentrated in vacuo. Crude product was purified by flash chromatography (hexanes:ethyl acetate 35:1) to afford 59 (81 mg, 0.189 mmol, 68%) as colorless oil. $^1$H NMR (CDCl$_3$, 500 MHz), δ ppm: 0.03 (s, 3H), 0.06 (s, 3H), 0.15 (s, 3H), 0.22 (s, 3H), 0.86 (s, 9H), 0.93 (s, 9H), 3.77 (dd, J=2.1, 12.7 Hz, 1H), 4.00 (dd, J=1.7, 12.7 Hz, 1H), 4.14 (dt, J=1.9, 7.9 Hz, 1H), 4.72 (d, J=7.9 Hz, 1H). $^{13}$C NMR (125 MHz, CDCl$_3$), δ ppm: −5.5, −5.4, −5.1, −4.2, 18.0, 18.2, 25.5, 25.7, 58.5, 76.5, 81.1, 82.3, 166.2.

2-deoxy-2,2-dichloro-3,5-di-O-(t-butyldimethylsilyl)-D-ribofuranose (60). 59 (70 mg, 0.163 mmol) was dissolved in 1 mL of anhydrous toluene and cooled to −78° C. To this solution was added 1.14 mL of DIBAL-H in THF solution (1.14 mmol). The reaction mixture was held at −78° C. at all time. Two hours later, the mixture was quenched by methanol at −20° C. and additional cold methanol was added. The mixture was then allowed to warm slowly to room temperature and was washed with 0.1 M HCl. Aqueous later was extracted with ether, the combined organic layer was washed with saturated NaHCO$_3$, water, brine, dried over anhydrous Na$_2$SO$_4$ and concentrated in vacuo. Column chromatography (hexanes:ethyl acetate 20:1) afforded 60 (65 mg, 0.151 mmol, 93%) as colorless oil. $^1$H NMR (CDCl$_3$, 500 MHz), δ ppm: 0.06 (stack, 3.6H), 0.11 (stack, 11H), 0.21 (s, 4.9H), 0.88 (s, 5.8H), 0.91 (s, 25H), 3.47 (d, J=12.6 Hz, 0.6H), 3.60 (dd, J=1.5, 11.3 Hz, 1H), 3.64 (dd, J=2.6, 11.5 Hz, 0.6H), 3.77 (dd, J=2.4, 11.4 Hz, 1H), 3.80 (dd, J=3.4, 12.7 Hz, 0.6H), 3.90 (m, 0.6H), 3.96 (stack, 2H), 4.61 (stack, 1.6H), 5.19 (d, J=8.9 Hz, 1H), 5.27 (t, J=5.2 Hz, 0.6H). $^{13}$C NMR (125 MHz, CDCl$_3$), δ ppm: −5.6, −5.54, −5.50, −5.4, −4.9, −4.8, −4.3, −4.0, 17.99, 18.00, 18.2, 18.3, 25.6, 25.78, 25.82, 61.0, 61.4, 77.5, 82.6, 83.3, 92.2, 92.3, 101.4, 102.0.

1-methylsulfonyl-2-deoxy-2,2-dichloro-3,5-di-O-(t-butyldimethylsilyl)-D-ribofuranose (61). 60 (57 mg, 0.132 mmol) was dissolved in 1.1 mL of CH$_2$Cl$_2$ and triethylamine (18.7 mg, 0.185 mmol). To this solution was added at 0° C. methanesulfonyl chloride (17.3 mg, 0.151 mmol). After 3 h of stirring under argon at room temperature, the mixture was evaporated in vacuo, and the residue was taken up in ethyl acetate. The solution was washed with saturated NaHCO$_3$, followed by 1 M HCl, water and brine. Solvent was concentrated under reduced pressure to afford 61 (67 mg, 0.132 mmol, almost quantitatively) as yellow liquid. $^1$H NMR (CDCl$_3$, 500 MHz), δ ppm: 0.04 (stack, 9H), 0.11 (s, 4H), 0.17 (s, 3H), 0.20 (s, 1.2H), 0.89 (stack, 26H), 3.66 (dd, J=3.3, 12.1 Hz, 0.4H), 3.74 (dd, J=3.7, 11.6 Hz, 1H), 3.82 (stack, 1.4H), 3.94 (d, J=7.5 Hz, 0.4H), 4.11 (m, 1H), 4.46 (d, J=5.4 Hz, 1H), 4.55 (d, J=7.9 Hz, 0.4H), 5.99 (s, 0.4H), 6.02 (s, 1H). $^{13}$C NMR (125 MHz, CDCl$_3$), δ ppm: −5.6, −5.50, −5.47, −5.4, −4.9, −4.8, −4.5, −4.1, 18.0, 18.3, 25.5, 25.77, 25.85, 40.0, 40.1, 45.9, 60.8, 61.4, 76.0, 78.1, 84.5, 86.7, 89.2, 89.3, 105.42, 105.45.

1-(2'-deoxy-2',2'-dichloro-3',5'-di-O-(t-butyldimethylsilyl)-ribofuranosyl)-nicotinamide (62). 61 (60 mg, 0.118 mmol) and nicotinamide (72 mg, 0.59 mmol) were dissolved in 6 mL of CH$_3$CN/CH$_2$Cl$_2$ (1:1). To this solution was added TMSOTf (39.3 mg, 0.177 mmol) under argon, the reaction mixture was kept refluxing overnight. Solvent was evaporated in vacuo, concentrated crude product was examined by NMR and used for the next step without further purification.

1-(2'-deoxy-2',2'-dichloro-ribofuranosyl)-nicotinamide (63). To a solution of 62 (63 mg, 0.118 mmol) in 1.5 mL of DMF were added acetic acid (34 mg, 0.56 mmol) and tetramethylammonnium fluoride (52 mg, 0.56 mmol). The reaction was stirred at room temperature overnight, then was concentrated and purified by HPLC (solvent was 20 mM ammonium acetate, compounds were eluted at a flow rate of 2 mL/min) to afford 63 (β-isomer, $t_R$=10.7 min, 7.2 mg, 0.023 mmol, 20%) and α-isomer ($t_R$=11.2 min, 23.8 mg, 0.078 mmol, 66%). β-isomer $^1$H NMR (D$_2$O, 500 MHz), δ ppm: 4.04 (dd, J=3.0, 13.3 Hz, 1H), 4.23 (dd, J=2.5, 13.4 Hz, 1H), 4.42 (m, 1H), 6.97 (s, 1H), 8.38 (dd, J=6.6, 7.7 Hz, 1H), 9.10 (d, J=8.1 Hz, 1H), 9.50 (d, J=6.4 Hz, 1H), 9.96 (s, 1H).

EXAMPLE 58

Effects of 2'-Deoxy-2'-chloro-nucleosides on Enzyme Activity

SirT1 Activity Assay: Reactions containing 200 µM NAD$^+$, 100 µM JB12 peptide, and 100 mM phosphate buffer at pH 7.5, with varying concentrations of 2'-deoxy-2'-chloro-nucleosides were initiated by addition of SirT1 enzyme to a concentration of 12.9 µM. Reactions were incubated for 30 mins at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

SirT2 Activity Assay: Reactions containing 800 µM NAD$^+$, 500 µM H3 peptide, and 100 mM phosphate buffer at pH 7.5, with varying concentrations of 2'-deoxy-2'-chloro-nucleosides were initiated by addition of SirT2 enzyme to a concentration of 16.6 µM. Reactions were incubated for 45 mins at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

SirT3 Activity Assay: Reactions containing 800 µM NAD$^+$, 500 µM H3 peptide, and 100 mM phosphate buffer at pH 7.5, with varying concentrations of 2'-deoxy-2'-chloro-nucleosides were initiated by addition of SirT3 enzyme to a concentration of 13.9 µM. Reactions were incubated for 2 hours at 37° C. and quenched by addition of trifluoroacetic acid to pH 2. After centrifugation to remove precipitates, reactions were injected on HPLC for activity analysis. Production of 2'- and 3'-AADPR were analyzed at 260 nm.

CD38 Activity Assay: CD38 (500 nM) in 100 mM phosphate buffer at pH 7.5 was incubated with various concentrations of 2'-deoxy-2'-chloro-nucleosides were for 30 mins at room temperature. 35 µL of the enzyme inhibitor solution was added to a cuvette containing 1 mL of 100 mM phosphate buffer at pH 7.5, containing 200 µM NGD$^+$. Reaction progress upon initiation by enzyme addition was monitored by 295 nm absorbance.

TABLE 7

Effects of 2'-Deoxy-2'-chloro-nucleosides on Enzyme Activity (see FIGS. 21 and 22 for results in graphical form)

| Structure | Name | SirT1 | SirT2 | SirT3 | CD38 |
|---|---|---|---|---|---|
| 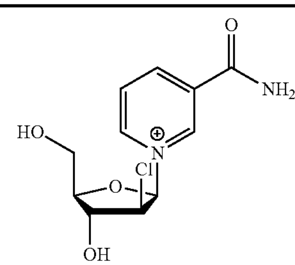 | β-ara-Cl-NR | $K_i$ = high mM | $K_i$ = 3.2 mM | $K_i$ = 546 µM |  |
| 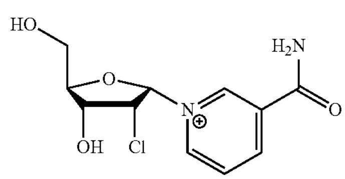 | α-ribo-Cl-NR |  | 50% inhibited at 1 mM | 86% inhibited at 1 mM |  |
| 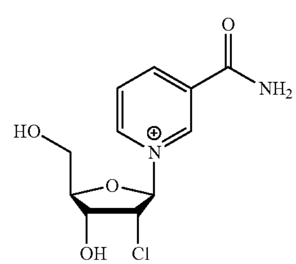 | β-ribo-Cl-NR |  | 43% inhibited at 1 mM | $K_i$ = 82 µM |  |

TABLE 7-continued

Effects of 2'-Deoxy-2'-chloro-nucleosides on Enzyme Activity (see FIGS. 21 and 22 for results in graphical form)

| Structure | Name | SirT1 | SirT2 | SirT3 | CD38 |
|---|---|---|---|---|---|
| 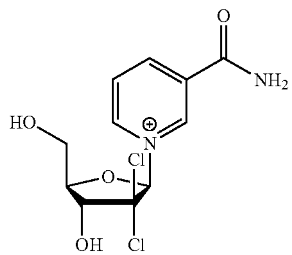 | β-gem-diCl-NR | $K_i = 780$ μM | $K_i = 403$ μM | $K_i = 123$ μM | 50% inhibited at 500 μM |

EXAMPLE 59

Toxicity of 2'-deoxy-2'-chloro-nucleosides

Assay for Determining Toxicity to HEK293 and Neuro2A Cells

1. HEK293 and Neuro2A cells were seeded in 96-well plate at a density of 25,000 cells/well the day before the experiment starts;
2. After the cells reach 50~60% confluency, media was taken out, and 100 μL of fresh media was added to each well;
3. Cl-derivatives were plated at 100 and 500 μM (in duplicates) concentrations;
4. After 12 hours' incubation at 37° C., the media was taken out, 100 μL of fresh media was added to each well along with 20 μL of 5 mg/mL of MTT solution (in PBS);
5. After 2 hours' incubation at 37° C., media was taken out and 100 μL of DMSO was added to each well, the plate was mixed on shaker for 5 mins;
6. Absorbance was measured at 570 nm.

TABLE 8

Toxicity of 2'-deoxy-2'-chloro-nucleosides to Neuro2A cells (results shown in graphical form in FIG. 23)

|  | 100 μM absorbance | 500 μM absorbance | 100 μM relative viability | 500 μM relative viability |
|---|---|---|---|---|
| β-ara-Cl-NR | 0 | 0 | 0 | 0 |
| α-ara-Cl-NR | 2.575 | 2.34 | 1.088795 | 0.989429 |
| gem-diCl-NR | 2.615 | 2.63 | 1.105708 | 1.112051 |
| control | 2.365 | 2.365 | 1 | 1 |

TABLE 9

Toxicity of 2'-deoxy-2'-chloro-nucleosides to HEK293 cells (results shown in graphical form in FIG. 24)

|  | 100 μM absorbance | 500 μM absorbance | 100 μM relative viability | 500 μM relative viability |
|---|---|---|---|---|
| β-ara-Cl-NR | 0 | 0 | 0 | 0 |
| α-ara-Cl-NR | 2.09 | 1.77 | 0.860082 | 0.728395 |
| gem-diCl-NR | 2.05 | 1.63 | 0.843621 | 0.670782 |
| control | 2.43 | 2.43 | 1 | 1 |

TABLE 10

Summary table of toxicity of 2'-deoxy-2'-chloro-nucleosides

| Structure | Name | EC$_{50}$ (μM) HEK293 | Neuro2A |
|---|---|---|---|
|  | α-ara-Cl-NR | kills 30% at 500 μM | not toxic at 500 μM |
|  | β-ara-Cl-NR | 5 | 9 |
|  | β-gem-diCl-NR | kills 30% at 500 μM | not toxic at 500 μM |

EXAMPLE 60

β-ara-Cl-NR Toxicity to HEK293 and Neuro2A Cells

The toxicity of β-ara-Cl-NR was further explored according to the following protocol:
1. HEK293 and Neuro2A cells were seeded in 96-well plate at a density of 25,000 cells/well the day before the experiment starts;
2. After the cells reach 50~60% confluency, media was taken out, and 100 μL of fresh media was added to each well;
3. β-ara-Cl-NR was plated according to the following Table 11:

TABLE 11 plating of β-ara-Cl-NR with HEK293 cells and with Neuro2A cells:

|   | 1 | 2 | 3 | 4 | 7 | 8 | 9 | 10 |
|---|---|---|---|---|---|---|---|---|
| A | 0 | 0 | 50 μM | 50 μM | 0 | 0 | 50 μM | 50 μM |
| B | 1 μM | 1 μM | 70 μM | 70 μM | 1 μM | 1 μM | 70 μM | 70 μM |
| C | 2 μM | 2 μM | 100 μM | 100 μM | 2 μM | 2 μM | 100 μM | 100 μM |
| D | 5 μM | 5 μM | | | 5 μM | 5 μM | | |
| E | 7.5 μM | 7.5 μM | | | 7.5 μM | 7.5 μM | | |
| F | 10 μM | 10 μM | | | 10 μM | 10 μM | | |
| G | 20 μM | 20 μM | | | 20 μM | 20 μM | | |
| H | 40 μM | 40 μM | | (HEK) | 40 μM | 40 μM | | (N2A) |

4. After 12 hours' incubation at 37° C., the media was taken out, 100 μL of fresh media was added to each well along with 20 μL of 5 mg/mL of MTT solution (in PBS);
5. After 2 hours' incubation at 37° C., media was taken out and 100 μL of DMSO was added to each well, the plate was mixed on shaker for 5 mins;
6. Absorbance was measured at 570 nm.
Results are shown in FIG. 30 and FIG. 31.

EXAMPLE 61

Immucillin-H Effects on β-ara-Cl-NR Toxicity to HEK293 and Neuro2A Cells

We speculated that like NR, the chloro derivatives might degrade in cells by action of an enzyme that converts it to ribose-1-phosphate. This enzyme is called purine nucleoside phosphorylase (PNP). Immucillin-H (gift of Schramm lab) is a potent inhibitor of PNP. We determined that PNP inhibition was largely incapable of preventing this toxicity. This suggests that decomposition of the nucleoside is unlikely to be associated with its mechanism of toxicity. This result suggests a novel mechanism of toxicity.
Assay:
1. HEK293 and Neuro2A cells were seeded in 96-well plate at a density of 25,000 cells/well the day before the experiment starts;
2. After the cells reach 50~60% confluency, media was taken out, and 100 μL of fresh media was added to each well;
3. β-ara-Cl-NR (black) and ImmH (bold) were plated according to the following Table 12:

TABLE 12

Plating of β-ara-Cl-NR (black) and ImmH (bold) in HEK293 cellks and Neuro2A cells

|   | 3 | 4 | 5 | 6 | 9 | 10 | 11 | 12 |
|---|---|---|---|---|---|---|---|---|
| A | 0 | 0 | 0 + 10 μM | 0 + 10 μM | 0 | 0 | 0 + 10 μM | 0 + 10 μM |
| B | 5 μM | 5 μM | 5 μM + 10 μM | 5 μM + 10 μM | 5 μM | 5 μM | 5 μM + 10 μM | 5 μM + 10 μM |
| C | 10 μM | 10 μM | 10 μM + 10 μM | 10 μM + 10 μM | 10 μM | 10 μM | 10 μM + 10 μM | 10 μM + 10 μM |
| D | 20 μM | 20 μM | 20 μM + 10 μM | 20 μM + 10 μM | 20 μM | 20 μM | 20 μM + 10 μM | 20 μM + 10 μM |
| E | 50 μM | 50 μM | 50 μM + 10 μM | 50 μM + 10 μM | 50 μM | 50 μM | 50 μM + 10 μM | 50 μM + 10 μM |
| F | 100 μM | 100 μM | 100 μM + 10 μM | 100 μM + 10 μM (N2A) | 100 μM | 100 μM | 100 μM + 10 μM | 100 μM + 10 μM (HEK) |

4. After 12 hours' incubation at 37° C., the media was taken out, 100 μL of fresh media was added to each well along with 20 μL of 5 mg/mL of MTT solution (in PBS);
5. After 2 hours' incubation at 37° C., media was taken out and 100 μL of DMSO was added to each well, the plate was mixed on shaker for 5 mins;
6. Absorbance was measured at 570 nm.
Results are shown in FIGS. 27-30.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Ma, J. A.; Cahard, D. Chem. Rev. 2008, 108, PR1-PR43.
2. Hagmann, W. K. J. Med. Chem. 2008, 51, 4359-4369.
3. Kirk, K. L. Org. Process Res. Dev. 2008, 12, 305-321.
4. O'Hagan, D. Chem. Soc. Rev. 2008, 37, (2), 308-319.
5. Nicolaou, K. C.; Mitchell, H. J. Angew. Chem. Int. Ed. 2001, 40, 1576-1624.
6. Williams, S. J.; Withers, S. G. Carbohydr. Res. 2000, 327, 27-46.
7. Vocadlo, D. J.; Withers, S. G. Carbohydr. Res. 2005, 340, 379-388.
8. Vocadlo, D. J.; Davies, G. J.; Laine, R.; Withers, S. G. Nature 2001, 412, 835-838.
9. Zechel, D. L.; Withers, S. G. Curr. Opin. Chem. Biol. 2001, 5, 643-649.
10. Sauve, A. A.; Deng, H. T.; Angeletti, R. H.; Schramm, V. L. J. Am. Chem. Soc. 2000, 122, 7855-7859.
11. Jackson, M. D.; Schmidt, M. T.; Oppenheimer, N. J.; Denu, J. M. J. Biol. Chem. 2003, 278, 50985-50998.
12. Liu, Q.; Kriksunov, I. A.; Jiang, H.; Graeff, R.; Lin, H.; Lee, H. C.; Hao, Q. Chem. Biol. 2008, 15, 1068-1078.
13. Porter, D. J.; Merrill, B. M.; Short, S. A. J. Biol. Chem. 1995, 270, 15551-15556.
14. Clark, J. L.; Hollecker, L.; Mason, J. C.; Stuyver, L. J.; Tharnish, P. M.; Lostia, S.; McBrayer, T. R.; Schinazi, R. F.; Watanabe, K. A.; Otto, M. J.; Furman, P. A.; Stec, W. J.; Patterson, S. E.; Pankiewicz, K. W. J. Med. Chem. 2005, 48, 5504-5508.
15. Ferrandina, G.; Ludovisi, M.; Lorusso, D.; Pignata, S.; Breda, E.; Savarese, A.; Del Medico, P.; Scaltriti, L.; Katsaros, D.; Priolo, D.; Scambia, G. J. Clin. Oncol. 2008, 26, 890-896.
16. Vulfovich, M.; Rocha-Lima, C. Expert Rev. Anticancer Ther. 2008, 8, 993-1002.
17. Silvestris, N.; Cinieri, S.; La Tone, I.; Pezzella, G.; Numico, G.; Orlando, L.; Lorusso, V. Breast 2008, 17, 220-226.
18. Eli Lilly, Eli Lilly 2007 Annual Report, 2007.
19. Bonate, P. L.; Arthaud, L.; Cantrell, W. R., Jr.; Stephenson, K.; Secrist, J. A., III; Weitman, S, Nat. Rev. Drug Discov. 2006, 5, 855-863.
20. Genzyme, Genzyme 2007 Annual Report 2007.
21. Sauve, A. A.; Wolberger, C.; Schramm, V. L.; Boeke, J. D. Annu. Rev. Biochem. 2006, 75, 435-465.
22. Hakme, A.; Wong, H. K.; Dantzer, F.; Schreiber, V. EMBO Rep. 2008, 9 1094-1100.
23. Smith, B. C.; Hallows, W. C.; Denu, J. M. Chem. Biol. 2008, 15, 1002-1013.
24. Haigis, M. C.; Mostoslaysky, R.; Haigis, K. M.; Fahie, K.; Christodoulou, D. C.; Murphy, A. J.; Valenzuela, D. M.; Yancopoulos, G. D.; Karow, M.; Blander, G.; Wolberger, C.; Prolla, T. A.; Weindruch, R.; Alt, F. W.; Guarente, L. Cell 2006, 126, 941-954.
25. Sleath, P. R.; Handlon, A. L.; Oppenheimer, N. J. J. Org. Chem. 1991, 56, 3608-3613.
26. Dax, K.; Albert, M.; Ortner, J.; Paul, B. J. Carbohydr. Res. 2000, 327, 47-86.
27. Reichman, U.; Watanabe, K. A.; Fox, J. J. Carbohydr. Res. 1975, 42, 233-240.
28. Tewson, T. J.; Welch, M. J. J. Org. Chem. 1978, 43, 1090-1092.
29. Watts, J. K.; Damha, M. J. Can. J. Chem. 2008, 86, 641-656.
30. Pankiewicz, K. W. Carbohydr. Res. 2000, 327, 87-105.
31. Larsen, C. H.; Ridgway, B. H.; Shaw, J. T.; Smith, D. M.; Woerpel, K. A. J. Am. Chem. Soc. 2005, 127, 10879-10884.
32. Mikhailopulo, I. A.; Poopeiko, N. E.; Sivets, G. G.; Khripach, N. B. Nucleosides Nucleotides 1995, 14, 383-384.
33. Wright, J. A.; Taylor, N. F.; Fox, J. J. J. Org. Chem. 1969, 34, 2632-2636.
34. Anderson, C. D.; Goodman, L.; Baker, B. R. J. Am. Chem. Soc. 1958, 80, 5247-5252.
35. Chou, T. S.; Heath, P. C.; Patterson, L. E.; Poteet, L. M.; Lakin, R. E.; Hunt, A. H. Synthesis 1992, 6, 565-570.
36. Fernandez, R.; Matheu, M. I.; Echarri, R.; Castillon, S. Tetrahedron, 1998, 54, 3523-3532.
37. McAtee, J. J.; Schinazi, R. F.; Liotta, D. C. J. Org. Chem. 1998, 63, 2161-2167.
38. Dehoux, C.; Gorrichon, L.; Baltas, M. Eur. J. Org. Chem. 2001, 6, 1105-1113.
39. Tripp, C. P.; Hair, M. L. Langmuir 1995, 11, 149-155.
40. Damrauer, R.; Simon, R.; Krempp, M. J. Am. Chem. Soc. 1991, 113, 4431-4435.
41. Ge, P.; Kirk, K. L. J. Org. Chem. 1997, 62, 3340-3343.
42. Enders, D.; Potthoff, M.; Raabe, G.; Runsink, J. Angew. Chem. Int. Ed. 1997, 36, 2362-2364.
43. Enders, D.; Faure, S.; Potthoff, M.; Runsink, J. Synthesis 2001, 15, 2307-2319.
44. Welch, J. T.; Plummer, J. S.; Chou, T. S. J. Org. Chem. 1991, 56, 353-359.
45. Handlon, A. L.; Xu, C.; Mullersteffner, H. M.; Schuber, F.; Oppenheimer, N. J. J. Am. Chem. Soc. 1994, 116, 12087-12088.
46. Natalini, P.; Ruggieri, S.; Raffaelli, N.; Magni, G. Biochemistry 1986, 25, 3725-3729.
47. Fox, J. J.; Hoffer, M.; Wempen, I.; Yung, N. C. J. Am. Chem. Soc. 1961, 83, 4066-4070.
48. Bauta, W. E.; Schulmeir, B. E.; Burke, B.; Puente, J. F.; Cantrell, Jr, W. R.; Lovette, D.; Goebel, J.; Andersen, B.; Ionescu, D.; Gui, R. Org. Proc R&D 2004, 8, 889-896.
49. Van Moorsel, C. J.; Peters, G. J.; Pinedo, H. M. Oncologist 1997, 2, 127.
50. a) Harris, G.; Ator, M.; Stubbe, J. Biochemistry, 1984, 23, 5214-5225. b) Harris, G.; Ashley, G. W.; Robins, M. J.; Tolman, R. L.; Stubbe, J. Biochemistry, 1987, 26, 1895-1902. c) Ashley, G. W.; Harris, G.; Stubbe, J. Biochemistry, 1988, 27, 7841-7845.
51. Gruen, M.; Becker, C.; Beste, A.; Reinstein, J.; Scheidig, A. J.; Goody, R. S. Protein Sci. 1999, 8, 2524-2528.
52. Codington, J. F.; Doerr, I. L.; Fox, J. J. J. Org. Chem. 1964, 29, 558-564.
53. Rague, B.; Chapleur, Y.; Castro, B. J. Chem. Soc. Perkin Trans. 11982, 2063-2066.
54. Jiang, X., Li, J., Zhang, R., Zhu, Y., Shen, J. Org. Process Res. Dev., 2008 12 (5), pp 888-891
55. Montgomery, J A, et al. J. Med. Chem. 1992, 35, 397-401

The invention claimed is:

1. A compound of formula (I):

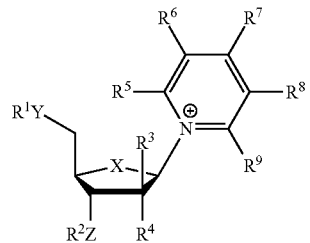

wherein R$^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

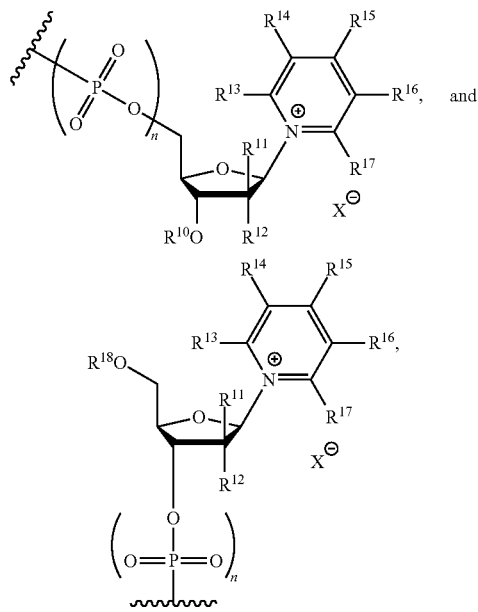

R$^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

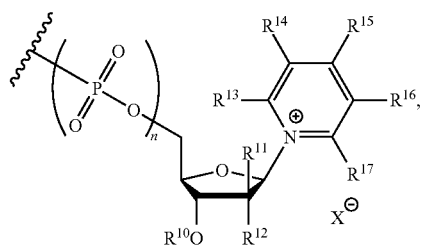

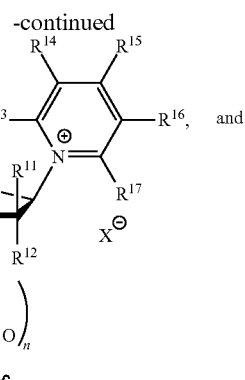

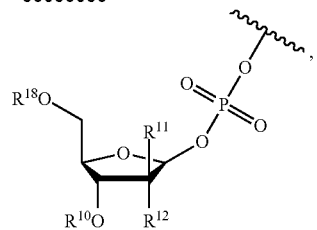

X, Y, and Z are O,
R$^3$ and R$^4$ are both F or Cl,
n is 1 or 2,
R$^8$ and R$^{16}$ are selected from the group consisting of hydrogen, COR$^{19}$, B(OR$^{20}$)$_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, CF$_3$, optionally substituted alkoxy, NO$_2$, optionally substituted alkylthio, optionally substituted amino, optionally substituted acylthio, hydroxy, mercapto, and optionally substituted thioamido,
R$^{19}$ is selected from the group consisting of hydrogen, amino, alkylamino, dialkylamino, hydroxy, alkoxy, and aryloxy,
R$^{20}$ is hydrogen or C$_1$-C$_6$ alkyl,
each of R$^5$, R$^6$, R$^7$, R$^9$, R$^{13}$, R$^{14}$, R$^{15}$, and R$^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, CF$_3$, optionally substituted alkoxy, optionally substituted aryl, NO$_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of R$^5$ and R$^6$ taken together, R$^6$ and R$^7$ taken together, R$^{13}$ and R$^{14}$ taken together, or R$^{14}$ and R$^{15}$ taken together, form a 5- or 6-membered saturated or unsaturated ring,
R$^{10}$ and R$^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate,
R$^{11}$ and R$^{12}$ are independently selected from the group consisting of hydrogen, F, Cl, Br, and I, $R^{23}$ is selected from the group consisting of hydrogen, alkyl, alkoxy, alkenyl, alkenyloxy, alkynyl, alkynyloxy, aryl, heteroaryl, cycloalkyl, and heterocycloalkyl, and X⁻ is an anion, or a pharmaceutically acceptable salt thereof.

2. The compound or salt of claim 1, wherein $R^8$ is $CONH_2$ and wherein $R^5$, $R^6$, $R^7$, and $R^9$ are hydrogen.

3. The compound or salt of claim 1, wherein $R^1$ and $R^2$ are independently selected from the group consisting of hydrogen, phosphate, diphosphate, and triphosphate.

4. The compound or salt of claim 1, wherein $R^1$ and $R^2$ are independently selected from the group consisting of hydrogen, phosphate, diphosphate, and triphosphate, $R^3$ is Cl, and $R^4$ is hydrogen.

5. A pharmaceutical composition comprising (a) a compound of claim 1 or a pharmaceutically acceptable salt thereof, and (b) a pharmaceutically acceptable carrier.

6. A compound of formula (I):

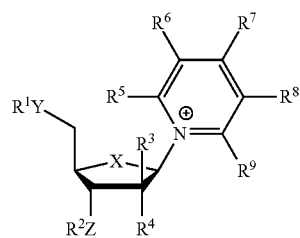

(I)

wherein (a) $R^1$ is hydrogen and $R^2$ is selected from the group consisting of

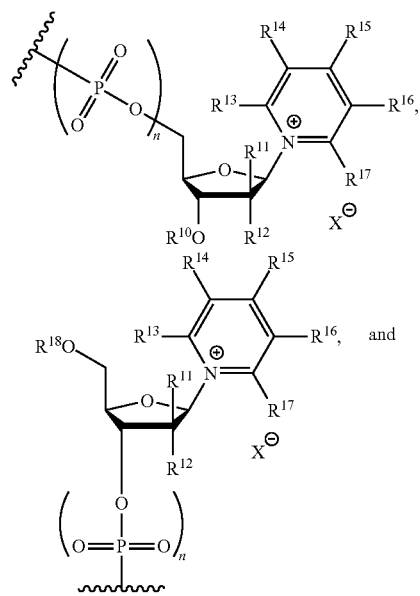

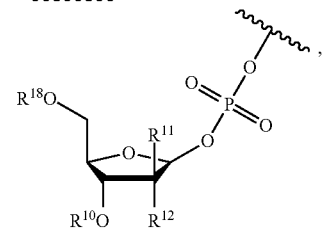

or (b) wherein $R^1$ is selected from the group consisting of

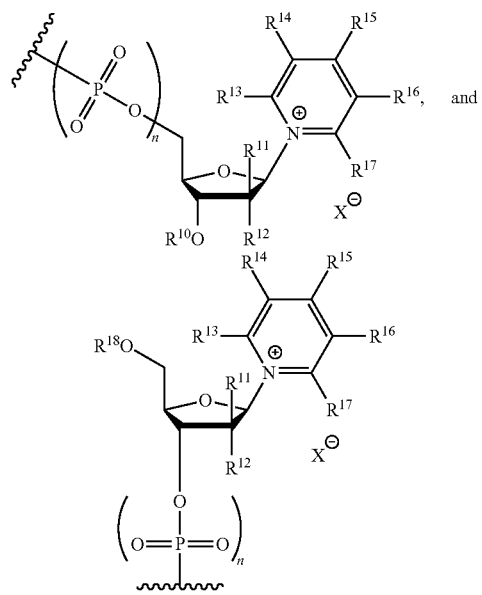

and $R^2$ is hydrogen,

X, Y, and Z are O, $R^3$ and $R^4$ are independently selected from the group consisting of hydrogen, F, Cl, Br, and I, with the proviso that $R^3$ and $R^4$ are not both hydrogen, n is 1 or 2, $R^8$ is selected from the group consisting of hydrogen, $COR^{19}$, $B(OR^2)_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, each of $R^5$, $R^6$, $R^7$, $R^9$, $R^{13}$, $R^{14}$, $R^{15}$, and $R^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, F, Cl, Br, and I, $R^{23}$ is selected from the group consisting of hydrogen, alkyl, alkoxy, alkenyl, alkenyloxy, alkynyl, alkynyloxy, aryl, heteroaryl, cycloalkyl, and heterocycloalkyl, and X⁻ is an anion, or a pharmaceutically acceptable salt thereof.

7. A pharmaceutical composition comprising the compound of claim 6 or a pharmaceutically acceptable salt thereof and a pharmaceutically acceptable carrier.

8. A polymer comprising as a monomeric unit a compound of formula (I):

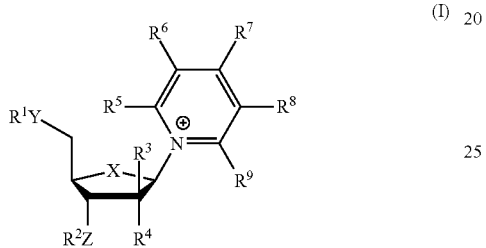
(I)

wherein $R^1$ is selected from the group consisting of hydrogen, optionally substituted acyl, optionally substituted acyloxy, trialkylsilyl, optionally substituted alkyl, optionally substituted alkylaryl, phosphate, diphosphate, triphosphate,

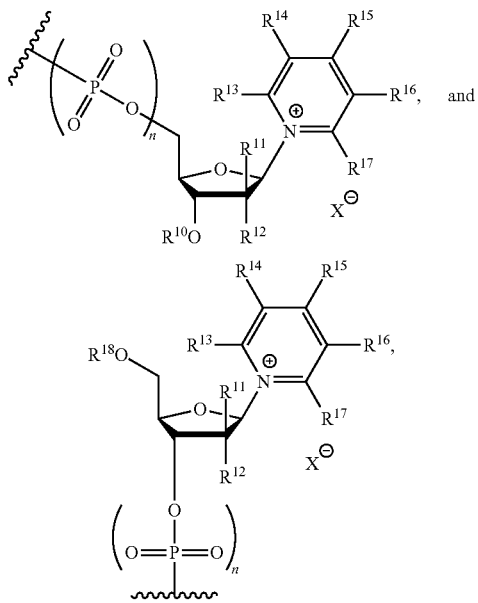

$R^2$ is selected from the group consisting of hydrogen, optionally substituted acyl, optionally substituted acyloxy, trialkylsilyl, optionally substituted alkyl, and optionally substituted alkylaryl, phosphate, diphosphate, triphosphate,

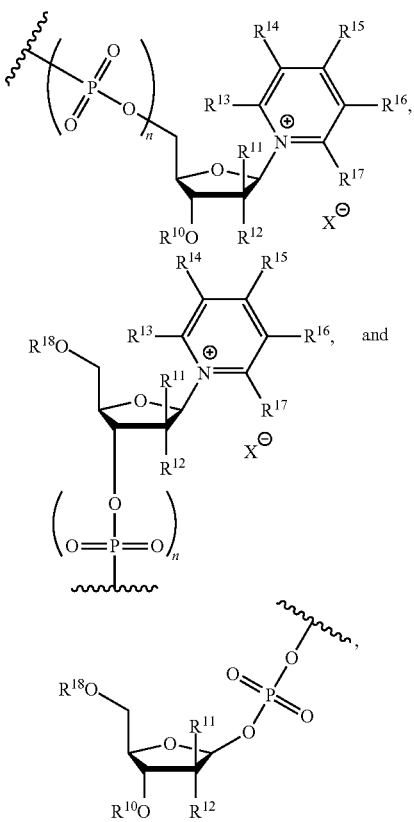

X, Y, and Z are O, $R^3$ and $R^4$ are both F or Cl, n is 1 or 2, $R^8$ is selected from the group consisting of hydrogen, $COR^{19}$, $B(OR^2)_2$, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, $NO_2$, optionally substituted alkylthio, optionally substituted amino, optionally substituted acylthio, hydroxy, mercapto, and optionally substituted thioamido, $R^{19}$ is selected from the group consisting of hydrogen, amino, alkylamino, dialkylamino, hydroxy, alkoxy, and aryloxy, $R^{20}$ is hydrogen or $C_1$-$C_6$ alkyl, each of $R^5$, $R^6$, $R^7$, $R^9$, $R^{13}$, $R^{14}$, $R^{15}$, and $R^{17}$ is independently selected from the group consisting of hydrogen, optionally substituted alkyl, optionally substituted alkenyl, optionally substituted alkynyl, optionally substituted cycloalkyl, optionally substituted cycloalkylalkyl, optionally substituted aryl, optionally substituted arylalkyl, F, Cl, Br, I, $CF_3$, optionally substituted alkoxy, optionally substituted aryl, $NO_2$, optionally substituted alkylthio, optionally substituted amino, optionally substituted acylamino, optionally substituted arylamino, optionally substituted acylthio, optionally substituted acyl, optionally substituted acyloxy, hydroxy, mercapto, and optionally substituted thioamido, or any of $R^5$ and $R^6$ taken together, $R^6$ and $R^7$ taken together, $R^{13}$ and $R^{14}$ taken together, or $R^{14}$ and $R^{15}$ taken together, form a 5- or 6-membered saturated or unsaturated ring, $R^{10}$ and $R^{18}$ are independently selected from the group consisting of hydrogen, optionally substituted acyl, optionally substituted acyloxy, trialkylsilyl, optionally substituted alkyl, optionally substituted alkylaryl, phosphate, diphosphate, and triphosphate, $R^{11}$ and $R^{12}$ are independently selected from the group consisting of hydrogen, F, Cl, Br, and I, $R^{23}$ is selected from the group consisting of hydrogen, alkyl, alkoxy, alkenyl, alkenyloxy, alkynyl, alkynyloxy, aryl, heteroaryl, cycloalkyl, and heterocycloalkyl, and $X^-$ is an anion, or a pharmaceutically acceptable salt thereof.

9. A pharmaceutical composition comprising (a) the polymer of claim 8 or a pharmaceutically acceptable salt thereof and (b) a pharmaceutically acceptable carrier.

* * * * *